United States Patent
Kashiki et al.

(10) Patent No.: US 10,239,886 B2
(45) Date of Patent: Mar. 26, 2019

(54) POLYMER COMPOUND AND ORGANIC SEMICONDUCTOR DEVICE USING THE SAME

(71) Applicant: SUMITOMO CHEMICAL COMPANY, LIMITED, Tokyo (JP)

(72) Inventors: Tomoya Kashiki, Osaka (JP); Eiji Yoshikawa, Tsukuba (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 249 days.

(21) Appl. No.: 15/325,542

(22) PCT Filed: Jul. 15, 2015

(86) PCT No.: PCT/JP2015/070235
§ 371 (c)(1),
(2) Date: Jan. 11, 2017

(87) PCT Pub. No.: WO2016/013460
PCT Pub. Date: Jan. 28, 2016

(65) Prior Publication Data
US 2017/0145030 A1 May 25, 2017

(30) Foreign Application Priority Data
Jul. 23, 2014 (JP) .................. 2014-149520

(51) Int. Cl.
*H01L 51/54* (2006.01)
*C07D 495/14* (2006.01)
(Continued)

(52) U.S. Cl.
CPC ......... *C07D 495/14* (2013.01); *C07D 495/02* (2013.01); *C07D 495/22* (2013.01);
(Continued)

(58) Field of Classification Search
CPC .... C08G 61/123; C08G 61/126; C08G 61/12; C08G 2261/00; C08G 2261/124;
(Continued)

(56) References Cited

U.S. PATENT DOCUMENTS

2009/0171048 A1  7/2009  Chan et al.
2011/0040069 A1  2/2011  Miura et al.
(Continued)

FOREIGN PATENT DOCUMENTS

CN  102532491 A  7/2012
JP  2013-079302 A  5/2013
(Continued)

OTHER PUBLICATIONS

International Search Report for application No. PCT/JP2015/070235 dated Oct. 6, 2015.
(Continued)

*Primary Examiner* — Andrew K Bohaty
(74) *Attorney, Agent, or Firm* — Sughrue Mion, PLLC

(57) ABSTRACT

A polymer compound comprising a structural unit represented by the formula (1):

(Continued)

wherein a ring A and a ring B represent a heterocyclic ring. A ring C represents a condensed aromatic heterocyclic ring not having a line-symmetric axis and a rotational axis. $Z^1$ and $Z^2$ represent a group represented by the formula (Z-1), a group represented by the formula (Z-2), a group represented by the formula (Z-3), a group represented by the formula (Z-4), a group represented by the formula (Z-5), a group represented by the formula (Z-6) or a group represented by the formula (Z-7).

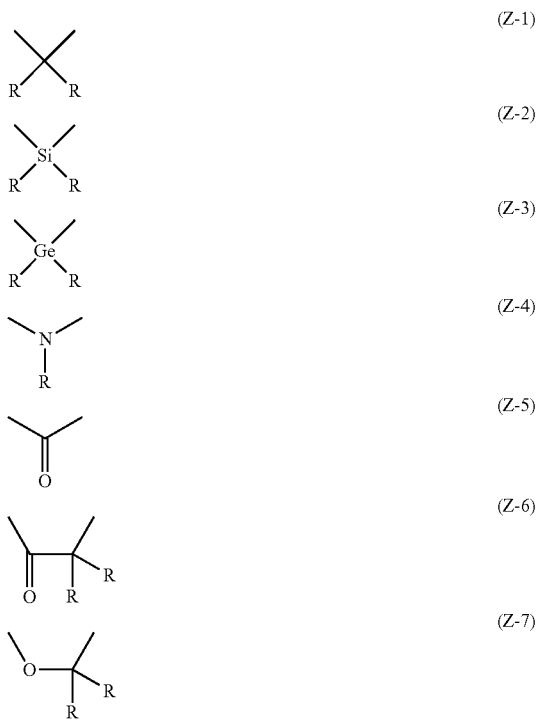

R represents an alkyl group, a cycloalkyl group, an alkoxy group, a cycloalkoxy group, an alkylthio group, a cycloalkylthio group, an aryl group or a monovalent heterocyclic group.].

15 Claims, 5 Drawing Sheets

(51) Int. Cl.

| C07D 495/02 | (2006.01) |
| --- | --- |
| C08G 61/12 | (2006.01) |
| H01L 29/786 | (2006.01) |
| H01L 51/50 | (2006.01) |
| H01L 51/00 | (2006.01) |
| C07D 495/22 | (2006.01) |
| C07F 5/02 | (2006.01) |
| C07F 7/22 | (2006.01) |
| H01L 51/05 | (2006.01) |
| H01L 51/42 | (2006.01) |

(52) U.S. Cl.
CPC ............ C07F 5/025 (2013.01); C07F 7/2208 (2013.01); C08G 61/12 (2013.01); C08G 61/123 (2013.01); C08G 61/126 (2013.01); H01L 29/786 (2013.01); H01L 51/0036 (2013.01); H01L 51/0043 (2013.01); H01L 51/0074 (2013.01); H01L 51/50 (2013.01); C08G 2261/124 (2013.01); C08G 2261/314 (2013.01); C08G 2261/3243 (2013.01); C08G 2261/3246 (2013.01); C08G 2261/411 (2013.01); C08G 2261/51 (2013.01); C08G 2261/92 (2013.01); H01L 51/0508 (2013.01); H01L 51/0541 (2013.01); H01L 51/0545 (2013.01); H01L 51/42 (2013.01)

(58) Field of Classification Search
CPC ...... C08G 2261/314; C08G 2261/3243; C08G 2261/3246; C08G 2261/411; C08G 2261/51; C08G 2261/92; C07F 5/025; C07F 7/2208; C07D 495/00; C07D 495/02; C07D 495/14; C07D 495/22; H01L 29/786; H01L 51/0032; H01L 51/0036; H01L 51/0043; H01L 51/0074; H01L 51/0541; H01L 51/0545; H01L 51/50; H01L 51/42
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| 2013/0237676 | A1 | 9/2013 | Hsu et al. |
| --- | --- | --- | --- |
| 2013/0324685 | A1 | 12/2013 | Aso et al. |
| 2015/0048279 | A1 | 2/2015 | Mitchell et al. |
| 2015/0144847 | A1 | 5/2015 | D'Lavari et al. |
| 2016/0159973 | A1 | 6/2016 | Kashiki et al. |
| 2017/0025613 | A1 | 1/2017 | Kanesaka et al. |

FOREIGN PATENT DOCUMENTS

| JP | 2013-235944 A | 11/2013 |
| --- | --- | --- |
| JP | 2015-093944 A | 5/2015 |
| WO | 2009/102031 A1 | 8/2009 |
| WO | 2010/020329 A1 | 2/2010 |
| WO | 2012/058209 A1 | 5/2012 |
| WO | 2012/105511 A1 | 8/2012 |
| WO | 2013/010614 A2 | 1/2013 |
| WO | 2013/120575 A1 | 8/2013 |
| WO | 2013/159862 A1 | 10/2013 |
| WO | 2013/159863 A1 | 10/2013 |
| WO | 2014/086457 A1 | 6/2014 |
| WO | 2015/163207 A1 | 10/2015 |

OTHER PUBLICATIONS

Communication dated Nov. 14, 2017, from the European Patent Office in counterpart European Application No. 15825379.9.
Zhang, et al., "Indacenodithiophene Semiconducting Polymers for High-Performance, Air-Stable Transistors", Journal of American Chemical Society, 2010, vol. 132, No. 33, pp. 11437-11439 (3 pages).
Machine Translation of JP 2013-235944 A, published Nov. 21, 2013.
Machine Translation of JP 2013-079302 A, published May 2, 2013.
Cheng, et al., "Carbazole-Based Ladder-Type Heptacylic Arene with Aliphatic Side Chains Leading to Enhanced Efficiency of Organic Photovoltaics", Chemistry of Materials, 2011, vol. 23, pp. 2361-2369 (9 pages).
Ma, et al., "Ladder-Type Dithienonaphthalene-Based Donor-Acceptor Copolymers for Organic Solar Cells", Macromolecules, 2013, vol. 46, pp. 4813-4821 (9 pages).

[Fig. 1]
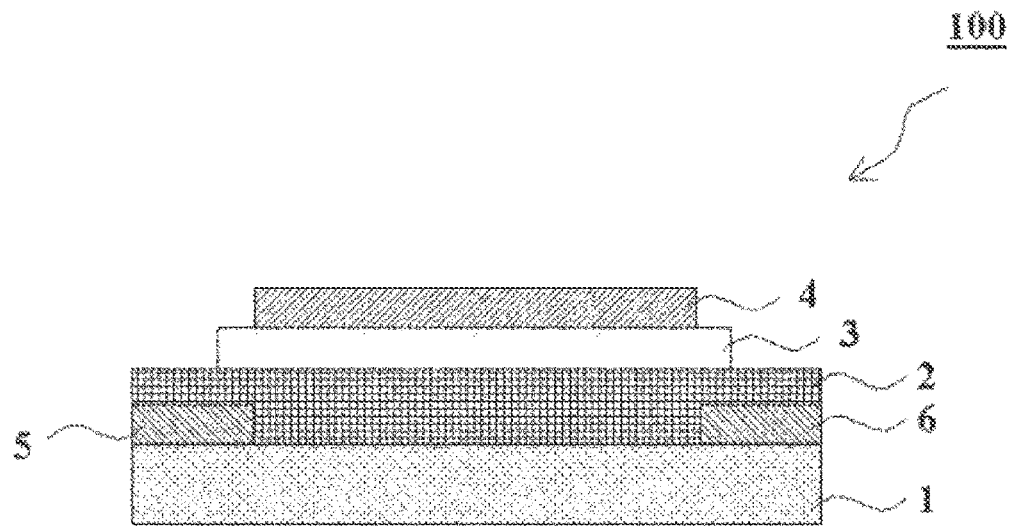
[Fig. 2]
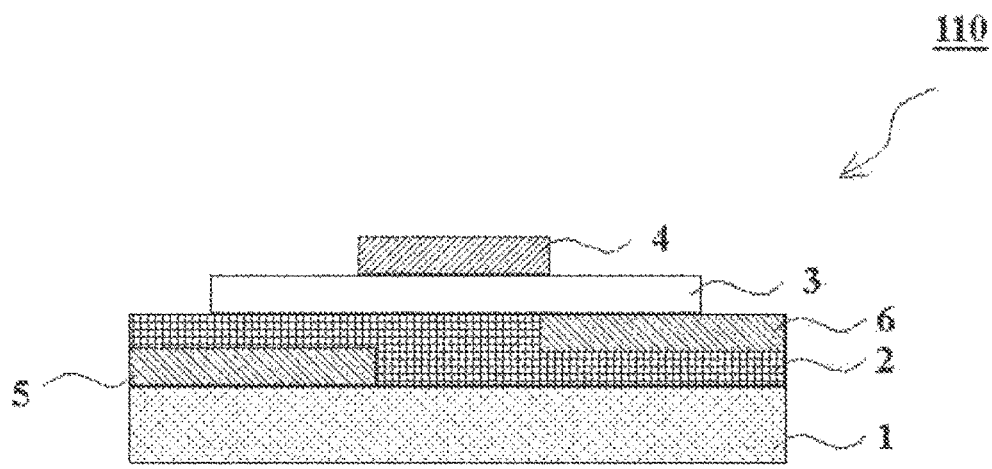

[Fig. 3]
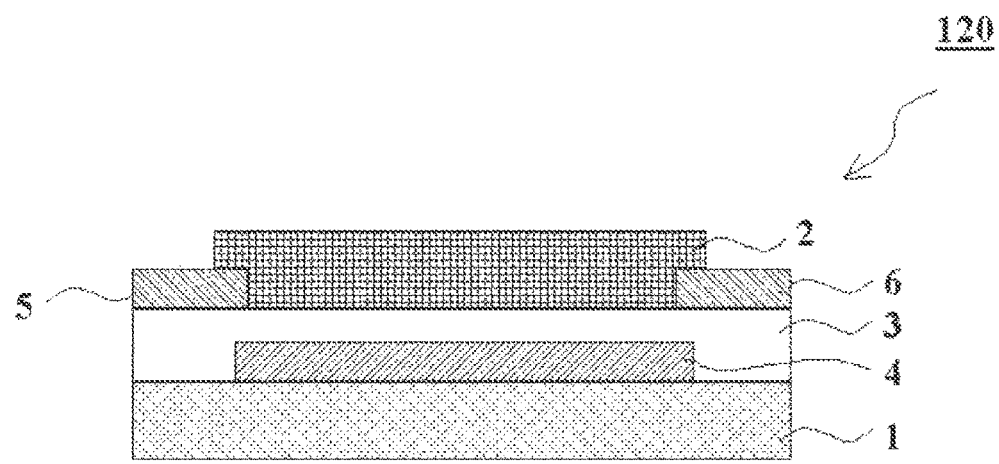
[Fig. 4]
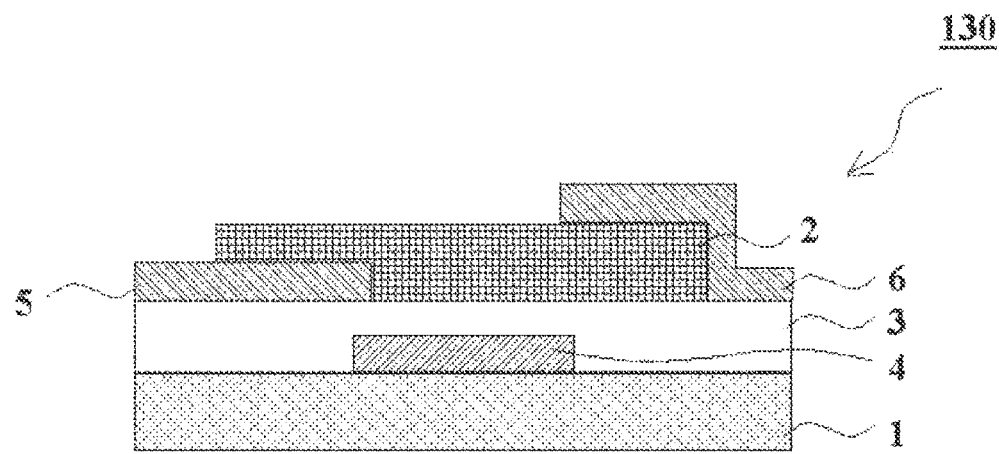

[Fig. 5]
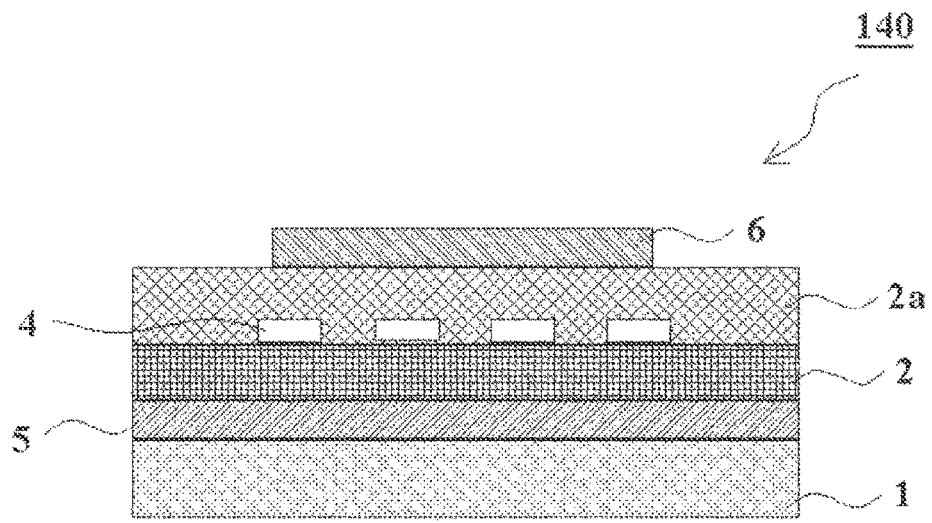
[Fig. 6]
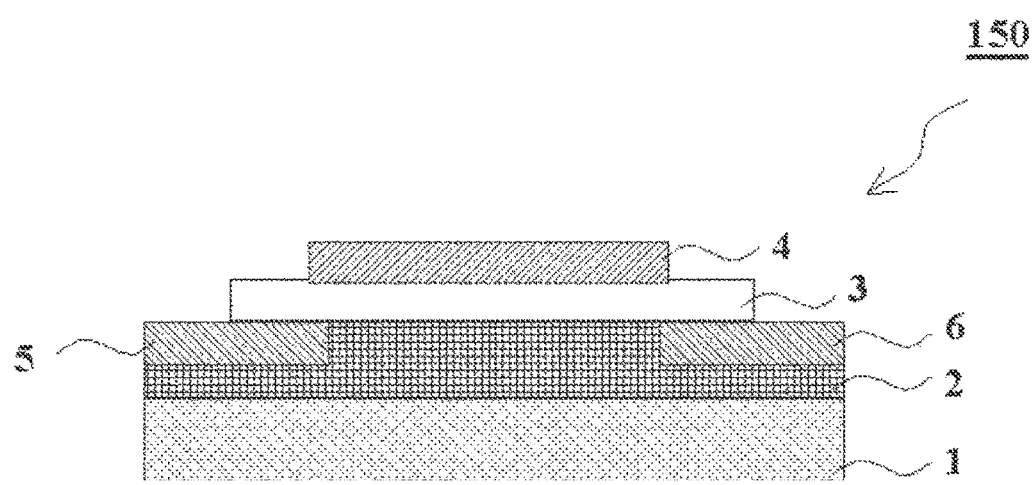

[Fig. 7]
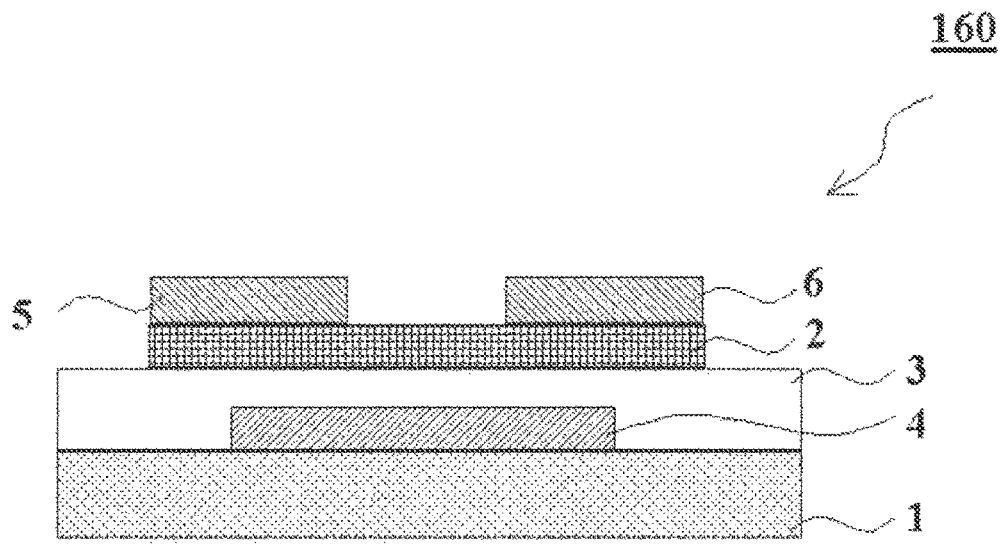
[Fig. 8]
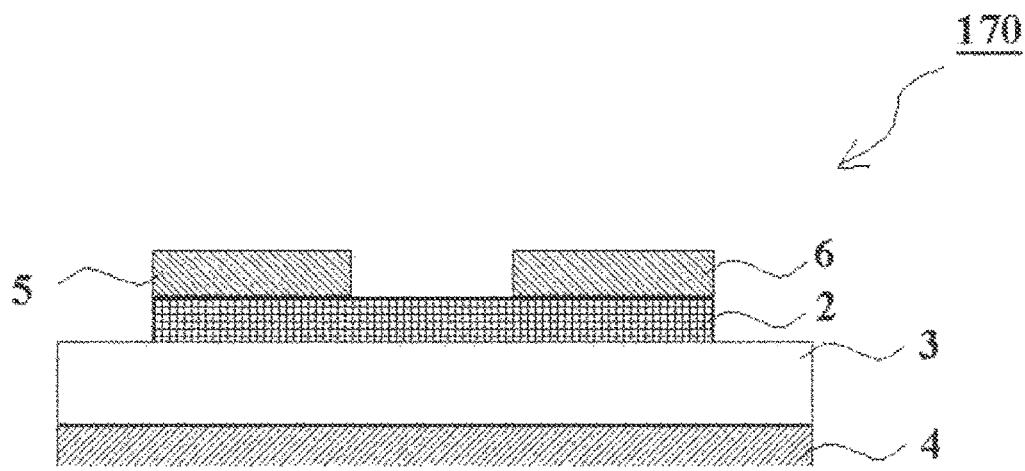

[Fig. 9]
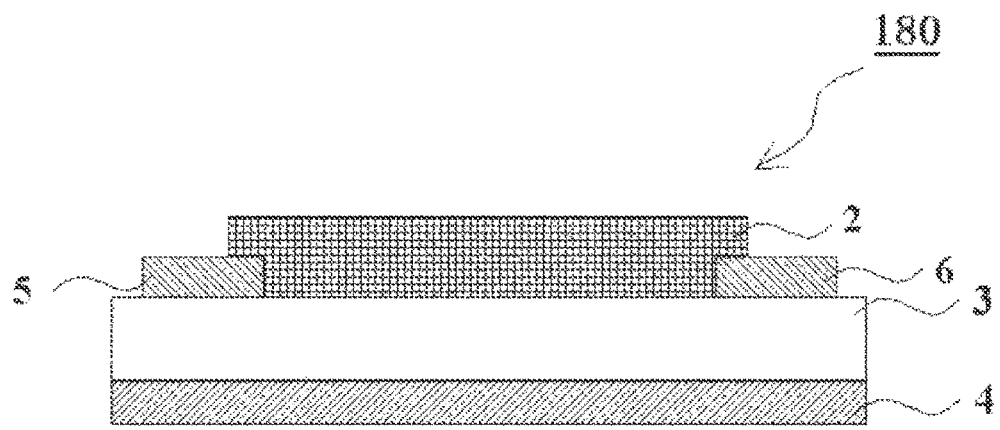

POLYMER COMPOUND AND ORGANIC SEMICONDUCTOR DEVICE USING THE SAME

CROSS REFERENCE TO RELATED APPLICATIONS

This is a National Stage of International Application No. PCT/JP2015/070235 filed Jul. 15, 2015, claiming priority based on Japanese Patent Application No. 2014-149520 filed Jul. 23, 2014, the contents of all of which are incorporated herein by reference in their entirety.

TECHNICAL FIELD

The present invention relates to a polymer compound and an organic semiconductor device using the same.

BACKGROUND ART

An organic transistor utilizing an organic semiconductor material as a polymer compound can be produced at lower temperature as compared with a conventional transistor utilizing an inorganic semiconductor material and an active layer of the organic transistor can be formed by a coating method, thus, the organic transistor has a merit that it can be produced by a simple process.

As the organic semiconductor material, for example, a polymer compound represented by the following formula is suggested (Non-patent document 1).

[Chemical Formula 1]

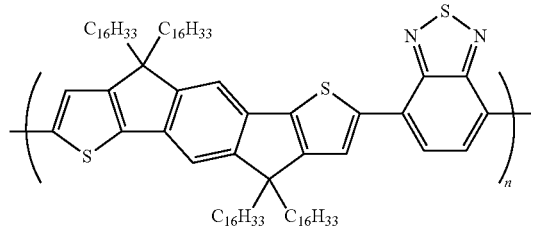

PRIOR ART DOCUMENT

Non-Patent Document

Non-patent document 1: Journal of American Chemical Society, 2010, vol. 132, p. 11437

SUMMARY OF THE INVENTION

With a top gate-bottom contact (hereinafter, referred to as "TGBC") device structure which is one of typical device structures of organic transistors, relatively high carrier mobility is obtained, however, a production process considering damages on an active layer is necessary since a gate insulating film is formed on the active layer. In contrast, with a bottom gate-bottom contact (hereinafter, referred to as "BGBC") device structure which is one of other typical device structures, the device production process is easy since an active layer is formed on a gate insulating film.

When the above-described polymer compound is used as a constitutional material of an active layer of an organic transistor, carrier mobility is not sufficient in the case of the BGBC device structure and higher carrier mobility is desired also in the TGBC device structure.

The present invention has an object of providing a polymer compound which can manifest excellent carrier mobility in any of the BGBC device structure and the TGBC device structure when used as a constitutional material of an active layer of an organic transistor.

The present invention is as described below.

[1] A polymer compound comprising a structural unit represented by the formula (1):

[Chemical Formula 2]

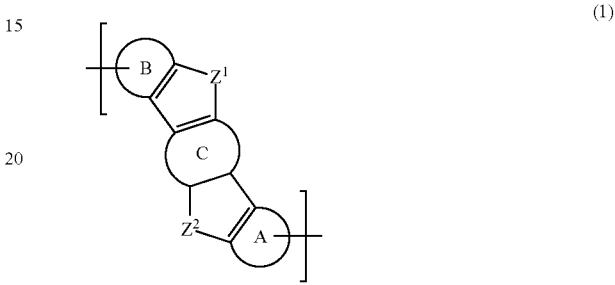

[wherein
a ring A and a ring B each independently represent a heterocyclic ring, and the heterocyclic ring optionally has a substituent.

a ring C represents a condensed aromatic heterocyclic ring not having a line-symmetric axis and a rotational axis, and the aromatic heterocyclic ring optionally has a substituent.

$Z^1$ and $Z^2$ each independently represent a group represented by the formula (Z-1), a group represented by the formula (Z-2), a group represented by the formula (Z-3), a group represented by the formula (Z-4), a group represented by the formula (Z-5), a group represented by the formula (Z-6) or a group represented by the formula (Z-7).]

[Chemical Formula 3]

   (Z-1)

   (Z-2)

   (Z-3)

   (Z-4)

   (Z-5)

   (Z-6)

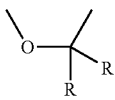

[wherein

R represents an alkyl group, a cycloalkyl group, an alkoxy group, a cycloalkoxy group, an alkylthio group, a cycloalkylthio group, an aryl group or a monovalent heterocyclic group, and these groups optionally have a substituent. When a plurality of R are present, they may be the same or different.].

[2] The polymer compound according to [1], wherein the structural unit represented by the formula (1) is a structural unit represented by the formula (2):

[Chemical Formula 4]

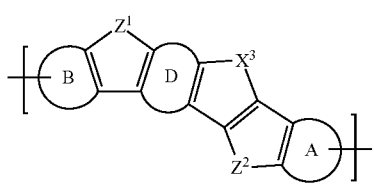

[wherein a ring A, a ring B, $Z^1$ and $Z^2$ represent the same meaning as described above.

$X^3$ represents an oxygen atom, a sulfur atom or a selenium atom.

a ring D represents an aromatic hydrocarbon ring selected from the group consisting of a benzene ring and a condensed ring obtained by condensation of 2 to 4 benzene rings, and the aromatic hydrocarbon ring optionally has a substituent.].

[3] The polymer compound according to [2], wherein the structural unit represented by the formula (2) is a structural unit represented by the formula (3):

[Chemical Formula 5]

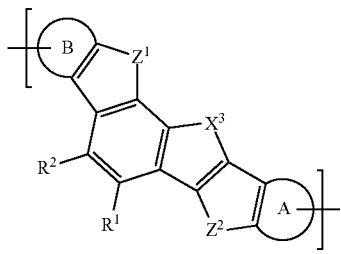

[wherein a ring A, a ring B, $X^3$, $Z^1$ and $Z^2$ represent the same meaning as described above.

$R^1$ and $R^2$ each independently represent a hydrogen atom, an alkyl group, a cycloalkyl group, an alkoxy group, a cycloalkoxy group, an alkylthio group, a cycloalkylthio group, an aryl group, a monovalent heterocyclic group, a halogen atom, a silyl group, an amino group, an alkenyl group, a cycloalkenyl group, an alkynyl group, a hydroxyl group, a nitro group, a cyano group, a carboxyl group, an alkylcarbonyl group, a cycloalkylcarbonyl group, an alkoxycarbonyl group or a cycloalkoxycarbonyl group, and of these groups, an alkyl group, a cycloalkyl group, an alkoxy group, a cycloalkoxy group, an alkylthio group, a cycloalkylthio group, an aryl group, a monovalent heterocyclic group, a silyl group, an amino group, an alkenyl group, an alkynyl group, an alkylcarbonyl group, a cycloalkylcarbonyl group, a cycloalkoxycarbonyl group and a cycloalkoxycarbonyl group each optionally have a substituent.].

[4] The polymer compound according to [3], wherein the structural unit represented by the formula (3) is a structural unit represented by the formula (4):

[Chemical Formula 6]

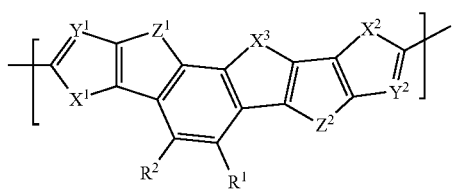

[wherein $R^1$, $R^2$, $X^3$, $Z^1$ and $Z^2$ represent the same meaning as described above.

$X^1$ and $X^2$ each independently represent an oxygen atom, a sulfur atom or a selenium atom.

$Y^1$ represents a nitrogen atom or a group represented by —$CR^5$=, and $Y^2$ represents a nitrogen atom or a group represented by —$CR^6$=. $R^5$ and $R^6$ each independently represent a hydrogen atom, an alkyl group, a cycloalkyl group, an alkoxy group, a cycloalkoxy group, an alkylthio group, a cycloalkylthio group, an aryl group, a monovalent heterocyclic group or a halogen atom, and of these groups, an alkyl group, a cycloalkyl group, an alkoxy group, a cycloalkoxy group, an alkylthio group, a cycloalkylthio group, an aryl group and a monovalent heterocyclic group each optionally have a substituent.].

[5] The polymer compound according to [4], wherein $X^1$, $X^2$ and the $X^3$ each represent a sulfur atom.

[6] The polymer compound according to [4] or [5], wherein $Y^1$ and $Y^2$ represent a group represented by —CH=.

[7] The polymer compound according to any one of [1] to [6], wherein $Z^1$ and $Z^2$ represent a group represented by the above-described formula (Z-1).

[8] The polymer compound according to any one of [1] to [7], further comprising a structural unit represented by the formula (5):

[Chemical Formula 7]

$$-\!\!\!-\!\text{Ar}\!\!-\!\!\!-\tag{5}$$

[wherein

Ar represents an arylene group or a divalent heterocyclic group, and these groups optionally have a substituent.].

[9] The polymer compound according to [8], wherein the polymer compound is an alternate copolymer of the structural unit represented by the formula (1) and the structural unit represented by the formula (5).

[10] A compound represented by the formula (6):

[Chemical Formula 8]

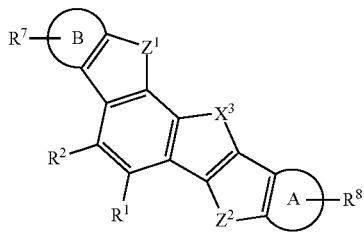
(6)

[wherein
a ring A and a ring B each independently represent a heterocyclic ring, and the heterocyclic ring optionally has a substituent other than $R^7$ and $R^8$.

$X^3$ represents an oxygen atom, a sulfur atom or a selenium atom.

$Z^1$ and $Z^2$ each independently represent a group represented by the formula (Z-1), a group represented by the formula (Z-2), a group represented by the formula (Z-3), a group represented by the formula (Z-4), a group represented by the formula (Z-5), a group represented by the formula (Z-6) or a group represented by the formula (Z-7).

$R^1$ and $R^2$ each independently represent a hydrogen atom, an alkyl group, a cycloalkyl group, an alkoxy group, a cycloalkoxy group, an alkylthio group, a cycloalkylthio group, an aryl group, a monovalent heterocyclic group, a halogen atom, a silyl group, an amino group, an alkenyl group, a cycloalkenyl group, an alkynyl group, a hydroxyl group, a nitro group, a cyano group, a carboxyl group, an alkylcarbonyl group, a cycloalkylcarbonyl group, an alkoxycarbonyl group or a cycloalkoxycarbonyl group, and of these groups, an alkyl group, a cycloalkyl group, an alkoxy group, a cycloalkoxy group, an alkylthio group, a cycloalkylthio group, an aryl group, a monovalent heterocyclic group, a silyl group, an amino group, an alkenyl group, a cycloalkenyl group, an alkynyl group, an alkylcarbonyl group and an alkoxycarbonyl group each optionally have a substituent. $R^7$ and $R^8$ each independently represent a hydrogen atom, a halogen atom, a silyl group, a hydroxyl group, a carboxyl group, a borate residue, a boric acid residue or an organotin residue, and of these groups, a silyl group optionally has a substituent.]

[Chemical Formula 9]

(Z-1)

(Z-2)

(Z-3)

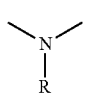
(Z-4)

(Z-5)

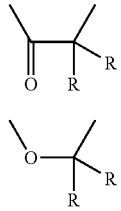
(Z-6)

(Z-7)

[wherein
R represents an alkyl group, a cycloalkyl group, an alkoxy group, a cycloalkoxy group, an alkylthio group, a cycloalkylthio group, an aryl group or a monovalent heterocyclic group, and these groups optionally have a substituent. When a plurality of R are present, they may be the same or different.].

[11] The compound according to [10], wherein the compound represented by the formula (6) is a compound represented by the formula (7):

[Chemical Formula 10]

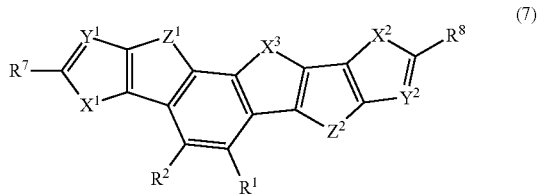
(7)

[wherein
$R^1$, $R^2$, $R^7$, $R^8$, $X^3$, $Z^1$ and $Z^2$ represent the same meaning as described above.

$X^1$ and $X^2$ each independently represent an oxygen atom, a sulfur atom or a selenium atom.

$Y^1$ represents a nitrogen atom or a group represented by —$CR^5$=, and $Y^2$ represents a nitrogen atom or a group represented by —$CR^6$=. $R^5$ and $R^6$ each independently represent a hydrogen atom, an alkyl group, a cycloalkyl group, an alkoxy group, a cycloalkoxy group, an alkylthio group, a cycloalkylthio group, an aryl group, a monovalent heterocyclic group or a halogen atom, and of these groups, an alkyl group, a cycloalkyl group, an alkoxy group, a cycloalkoxy group, an alkylthio group, a cycloalkylthio group, an aryl group and a monovalent heterocyclic group each optionally have a substituent.].

[12] An organic semiconductor composition comprising the polymer compound according to any one of [1] to [9].

[13] An organic semiconductor device having a first electrode, a second electrode and an organic semiconductor layer, wherein the organic semiconductor layer contains the polymer compound according to any one of [1] to [9].

[14] The organic semiconductor device according to [13], wherein the device is any of an organic transistor, a photoelectric conversion device, an organic electroluminescent device, an organic field effect type transistor sensor and an organic conductivity modulation type sensor.

[15] The organic semiconductor device according to [14], wherein the device is an organic transistor.

BRIEF EXPLANATION OF DRAWINGS

FIG. 1 is a schematic cross-sectional view showing one example of the organic transistor of the present invention.

FIG. 2 is a schematic cross-sectional view showing another example of the organic transistor of the present invention.

FIG. 3 is a schematic cross-sectional view showing another example of the organic transistor of the present invention.

FIG. 4 is a schematic cross-sectional view showing another example of the organic transistor of the present invention.

FIG. 5 is a schematic cross-sectional view showing another example of the organic transistor of the present invention.

FIG. 6 is a schematic cross-sectional view showing another example of the organic transistor of the present invention.

FIG. 7 is a schematic cross-sectional view showing another example of the organic transistor of the present invention.

FIG. 8 is a schematic cross-sectional view showing another example of the organic transistor of the present invention.

FIG. 9 is a schematic cross-sectional view showing another example of the organic transistor of the present invention.

MODES FOR CARRYING OUT THE INVENTION

Suitable embodiments of the present invention will be illustrated in detail below, if necessary referring to drawings. In explanation of the drawings, the same element is endowed with the same sign, and duplicated explanations are omitted.

<Polymer Compound>
(First Structural Unit)

The polymer compound of the present invention is a polymer compound comprising a structural unit represented by the formula (1) (hereinafter, referred to as "first structural unit" in some cases). The first structural units may be contained each singly or two or more of them may be contained in the polymer compound. The polymer compound of the present invention is preferably a conjugated polymer compound.

[Chemical Formula 11]

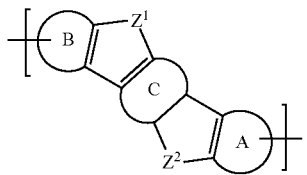

(1)

In the formula (1), a ring A and a ring Beach independently represent a heterocyclic ring, and the heterocyclic ring optionally has a substituent. The heterocyclic ring represented by a ring A and a ring B denotes an organic compound having a cyclic structure in which the element constituting the ring includes not only a carbon atom but also a hetero atom such as oxygen, sulfur, nitrogen, phosphorus, boron, silicon and the like contained in the ring. The heterocyclic ring has a number of carbon atoms of preferably 2 to 30, more preferably 2 to 14, further preferably 3 to 8. The number of carbon atoms does not include the number of carbon atoms of the substituent which the heterocyclic ring described later optionally has.

The heterocyclic ring is preferably an aromatic heterocyclic ring. Examples thereof include a furan ring, a thiophene ring, a selenophene ring, a pyrrole ring, an oxazole ring, a thiazole ring, an imidazole ring, a pyridine ring, a benzofuran ring, a benzothiophene ring, a thienothiophene ring and a 2,1,3-benzothiadiazole ring.

The substituent which the heterocyclic ring optionally has includes, for example, an alkyl group, a cycloalkyl group, an alkoxy group, a cycloalkoxy group, an alkylthio group, a cycloalkylthio group, an aryl group, a monovalent heterocyclic group, a halogen atom, a silyl group, an amino group, an alkenyl group, a cycloalkenyl group, an alkynyl group, a hydroxyl group, a nitro group, a cyano group, a carboxyl group, an alkylcarbonyl group, a cycloalkylcarbonyl group, an alkoxycarbonyl group and a cycloalkoxycarbonyl group.

The alkyl group as the substituent which the heterocyclic ring represented by a ring A and a ring B optionally has may be any of a linear alkyl group and a branched alkyl group. The alkyl group has a number of carbon atoms of usually 1 to 30 (in the case of a branched alkyl group, usually 3 to 30), preferably 1 to 20 (in the case of a branched alkyl group, 3 to 20). The number of carbon atoms does not include the number of carbon atoms of the substituent which the alkyl group described later optionally has.

The alkyl group includes, for example, linear alkyl groups such as a methyl group, an ethyl group, a n-propyl group, a n-butyl group, a n-hexyl group, a n-octyl group, a n-dodecyl group, a n-hexadecyl group and the like, and branched alkyl groups such as an isopropyl group, an isobutyl group, a sec-butyl group, a tert-butyl group, a 2-ethylhexyl group, a 3,7-dimethyloctyl group and the like.

The alkyl group optionally has a substituent, and the substituent includes, for example, an alkoxy group, a cycloalkoxy group, an aryl group and a halogen atom. The alkyl group having a substituent includes, for example, a methoxyethyl group, a benzyl group, a trifluoromethyl group and a perfluorohexyl group.

The cycloalkyl group as the substituent which the heterocyclic ring represented by a ring A and a ring B optionally has a number of carbon atoms of usually 3 to 30, preferably 3 to 20. The number of carbon atoms does not include the number of carbon atoms of the substituent which the cycloalkyl group described later optionally has.

The cycloalkyl group includes, for example, a cyclopentyl group and a cyclohexyl group.

The cycloalkyl group optionally has a substituent, and the substituent includes, for example, an alkoxy group, a cycloalkoxy group, an aryl group and a halogen atom.

The alkoxy group as the substituent which the heterocyclic ring represented by a ring A and a ring B optionally has may be any of a linear alkoxy group and a branched alkoxy group. The alkoxy group has a number of carbon atoms of usually 1 to 30 (in the case of a branched alkoxy group, usually 3 to 30), preferably 1 to 20 (in the case of a branched alkoxy group, 3 to 20). The number of carbon atoms does not include the number of carbon atoms of the substituent which the alkoxy group described later optionally has.

The alkoxy group includes, for example, linear alkoxy groups such as a methoxy group, an ethoxy group, a n-propyloxy group, a n-butyloxy group, a n-hexyloxy group, a n-octyloxy group, a n-dodecyloxy group, a n-hexadecyloxy group and the like, and branched alkoxy groups such as an isopropyloxy group, an isobutyloxy group, a sec-butyloxy group, a tert-butyloxy group, a 2-ethylhexyloxy group, a 3,7-dimethyloctyloxy group and the like.

The alkoxy group optionally has a substituent, and the substituent includes, for example, an alkoxy group, a cycloalkoxy group, an aryl group and a halogen atom.

The cycloalkoxy group as the substituent which the heterocyclic ring represented by a ring A and a ring B optionally has a number of carbon atoms of usually 3 to 30, preferably 3 to 20. The number of carbon atoms does not include the number of carbon atoms of the substituent which the cycloalkoxy group described later optionally has.

The cycloalkoxy group includes, for example, a cyclopentyloxy group and a cyclohexyloxy group.

The cycloalkoxy group optionally has a substituent, and the substituent includes, for example, an alkoxy group, a cycloalkoxy group, an aryl group and a halogen atom.

The alkylthio group as the substituent which the heterocyclic ring represented by a ring A and a ring B optionally has may be any of a linear alkylthio group and a branched alkylthio group. The alkylthio group has a number of carbon atoms of usually 1 to 30 (in the case of a branched alkylthio group, usually 3 to 30), preferably 1 to 20 (in the case of a branched alkylthio group, 3 to 20). The number of carbon atoms does not include the number of carbon atoms of the substituent which the alkylthio group described later optionally has.

The alkylthio group includes, for example, linear alkylthio groups such as a methylthio group, an ethylthio group, a n-propylthio group, a n-butylthio group, a n-hexylthio group, a n-octylthio group, a n-dodecylthio group, a n-hexadecylthio group and the like, and branched alkylthio groups such as an isopropylthio group, an isobutylthio group, a sec-butylthio group, a tert-butylthio group, a 2-ethylhexylthio group, a 3,7-dimethyloctylthio group and the like.

The alkylthio group optionally has a substituent, and the substituent includes, for example, an alkoxy group, a cycloalkoxy group, an aryl group and a halogen atom.

The cycloalkylthio group as the substituent which the heterocyclic ring represented by a ring A and a ring B optionally has a number of carbon atoms of usually 3 to 30, preferably 3 to 20. The number of carbon atoms does not include the number of carbon atoms of the substituent which the cycloalkylthio group described later optionally has.

The cycloalkylthio group includes, for example, a cyclopentylthio group and a cyclohexylthio group.

The cycloalkylthio group optionally has a substituent, and the substituent includes, for example, an alkoxy group, a cycloalkoxy group, an aryl group and a halogen atom.

The aryl group as the substituent which the heterocyclic ring represented by a ring A and a ring B optionally has is an atomic group remaining after removing from an aromatic hydrocarbon one hydrogen atom bonding directly to a carbon atom constituting the ring, and includes a group having a condensed ring and a group obtained by directly bonding two or more groups selected from the group consisting of an independent benzene ring and a condensed ring. The aryl group has a number of carbon atoms of usually 6 to 30, preferably 6 to 20. The number of carbon atoms does not include the number of carbon atoms of the substituent which the aryl group described later optionally has.

The aryl group includes, for example, a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group and a 4-phenylphenyl group.

The aryl group optionally has a substituent, and the substituent includes, for example, an alkyl group, a cycloalkyl group, an alkoxy group, a cycloalkoxy group, an alkylthio group, a cycloalkylthio group, a monovalent heterocyclic group and a halogen atom. The aryl group having a substituent includes, for example, a 4-hexadecylphenyl group, a 3,5-dimethoxyphenyl group and a pentafluorophenyl group. When the aryl group has a substituent, the substituent is preferably an alkyl group or a cycloalkyl group.

The monovalent heterocyclic group as the substituent which the heterocyclic ring represented by a ring A and a ring B optionally has is an atomic group remaining after removing from a heterocyclic compound one hydrogen atom bonding directly to a carbon atom or a hetero atom constituting the ring, and includes a group having a condensed ring and a group obtained by directly bonding two or more groups selected from the group consisting of an independent heterocyclic group and a condensed ring. The monovalent heterocyclic group has a number of carbon atoms of usually 2 to 30, preferably 3 to 20. The number of carbon atoms does not include the number of carbon atoms of the substituent which the monovalent heterocyclic group described later optionally has.

The monovalent heterocyclic group includes, for example, a 2-furyl group, a 3-furyl group, a 2-thienyl group, a 3-thienyl group, a 2-pyrrolyl group, a 3-pyrrolyl group, a 2-oxazolyl group, a 2-thiazolyl group, a 2-imidazolyl group, a 2-pyridyl group, a 3-pyridyl group, a 4-pyridyl group, a 2-benzofuryl group, a 2-benzothienyl group, a 2-thienothienyl group and a 4-(2,1,3-benzothiadiazolyl) group.

The monovalent heterocyclic group optionally has a substituent, and the substituent includes, for example, an alkyl group, a cycloalkyl group, an alkoxy group, a cycloalkoxy group, an alkylthio group, a cycloalkylthio group, an aryl group and a halogen atom. The monovalent heterocyclic group having a substituent includes, for example, a 5-octyl-2-thienyl group and a 5-phenyl-2-furyl group. When the monovalent heterocyclic group has a substituent, the substituent is preferably an alkyl group or a cycloalkyl group.

The halogen atom as the substituent which the heterocyclic ring represented by a ring A and a ring B optionally has includes, for example, a fluorine atom, a chlorine atom, a bromine atom and an iodine atom.

The silyl group as the substituent which the heterocyclic ring represented by a ring A and a ring B optionally has optionally has a substituent. The substituent which a silyl group optionally has includes, for example, an alkyl group, a cycloalkyl group and an aryl group. The silyl group having a substituent includes, for example, a trimethylsilyl group, a triethylsilyl group, a triisopropylsilyl group, a tert-butyldimethylsilyl group, a tert-butyldiphenylsilyl group and a triphenylsilyl group.

The silyl group has a number of carbon atoms of usually 0 to 90, preferably 3 to 90.

The amino group as the substituent which the heterocyclic ring represented by a ring A and a ring B optionally has optionally has a substituent. The substituent which an amino group optionally has includes, for example, an alkyl group, a cycloalkyl group and an aryl group. The amino group having a substituent includes, for example, a dimethylamino group, a diethylamino group, a diisopropylamino group and a diphenylamino group. The amino group has a number of carbon atoms of usually 0 to 90, preferably 2 to 90.

The alkenyl group as the substituent which the heterocyclic ring represented by a ring A and a ring B optionally has may be any of a linear alkenyl group and a branched alkenyl group. The alkenyl group has a number of carbon atoms of usually 2 to 30 (in the case of a branched alkenyl group, usually 3 to 30), preferably 2 to 20 (in the case of a branched alkenyl group, 3 to 20). The number of carbon atoms does not include the number of carbon atoms of the substituent which the alkenyl group described later optionally has.

The alkenyl group includes, for example, a vinyl group, a 1-propenyl group, a 2-propenyl group, a 1-hexenyl group, a 1-dodecenyl group and a 1-hexadecenyl group.

The alkenyl group optionally has a substituent, and the substituent includes, for example, an aryl group, a halogen atom and a silyl group.

The cycloalkenyl group as the substituent which the heterocyclic ring represented by a ring A and a ring B optionally has a number of carbon atoms of usually 3 to 30, preferably 3 to 20. The number of carbon atoms does not include the number of carbon atoms of the substituent which the cycloalkenyl group described later optionally has.

The cycloalkenyl group includes, for example, a 1-cyclohexenyl group.

The cycloalkenyl group optionally has a substituent, and the substituent includes, for example, an aryl group, a halogen atom and a silyl group.

The alkynyl group as the substituent which the heterocyclic ring represented by a ring A and a ring B optionally has may be any of a linear alkynyl group and a branched alkynyl group. The alkynyl group has a number of carbon atoms of usually 2 to 30 (in the case of a branched alkynyl group, usually 4 to 30), preferably 2 to 20 (in the case of a branched alkynyl group, 4 to 20). The number of carbon atoms does not include the number of carbon atoms of the substituent which the alkynyl group described later optionally has.

The alkynyl group includes, for example, an ethynyl group, a 1-propynyl group, a 1-hexynyl group, a 1-dodecynyl group and a 1-hexadecynyl group.

The alkynyl group optionally has a substituent, and the substituent includes, for example, an aryl group, a halogen atom and a silyl group.

The alkylcarbonyl group as the substituent which the heterocyclic ring represented by a ring A and a ring B optionally has includes, for example, a group obtained by bonding of the above-described alkyl group and a carbonyl group.

The alkylcarbonyl group includes, for example, linear alkylcarbonyl groups such as an acetyl group, a n-propanoyl group, a n-butanoyl group, a n-hexanoyl group, a n-octanoyl group, a n-dodecanoyl group, a n-hexadecanoyl group and the like, and branched alkylcarbonyl groups such as an isobutanoyl group, a sec-butanoyl group, a tert-butanoyl group, a 2-ethylhexanoyl group and the like.

The cycloalkylcarbonyl group as the substituent which the heterocyclic ring represented by a ring A and a ring B optionally has includes, for example, a group obtained by bonding of the above-described cycloalkyl group and a carbonyl group.

The cycloalkylcarbonyl group includes, for example, a cyclopentylcarbonyl group and a cyclohexylcarbonyl group.

The alkoxycarbonyl group as the substituent which the heterocyclic ring represented by a ring A and a ring B optionally has includes, for example, a group obtained by bonding of the above-described alkoxy group and a carbonyl group.

The alkoxycarbonyl group includes, for example, linear alkoxycarbonyl groups such as a methoxycarbonyl group, an ethoxycarbonyl group, a n-propyloxycarbonyl group, a n-butoxycarbonyl group, a n-hexyloxycarbonyl group, a n-octyloxycarbonyl group, a n-dodecyloxycarbonyl group, a n-hexadecyloxycarbonyl group and the like, and branched alkoxycarbonyl groups such as an isopropyloxycarbonyl group, an isobutyloxycarbonyl group, a sec-butyloxycarbonyl group, a tert-butyloxycarbonyl group, a 2-ethylhexyloxycarbonyl group and the like.

The cycloalkoxycarbonyl group as the substituent which the heterocyclic ring represented by a ring A and a ring B optionally has includes, for example, a group obtained by bonding of the above-described cycloalkoxy group and a carbonyl group.

The cycloalkoxycarbonyl group includes, for example, a cyclopentyloxycarbonyl group and a cyclohexyloxycarbonyl group.

It is preferable that a ring A and a ring B are the same heterocyclic ring, since synthesis of the polymer compound of the present invention is easy.

The heterocyclic ring represented by a ring A and a ring B has no substituent, alternatively when the ring has a substituent, the substituent is preferably an alkyl group, a cycloalkyl group, an alkoxy group or a cycloalkoxy group, more preferably an alkyl group or an alkoxy group.

A ring A and a ring B are preferably constituted of a 5-membered and/or 6-membered aromatic heterocyclic ring, more preferably constituted only of a 5-membered aromatic heterocyclic ring, and a monocyclic 5-membered aromatic heterocyclic ring is further preferable, since an organic transistor produced by using the polymer compound of the present invention is more excellent in carrier mobility.

In the formula (1), a ring C represents a condensed aromatic heterocyclic ring not having a line-symmetric axis and a rotational axis, and the aromatic heterocyclic ring optionally has a substituent. The condensed aromatic heterocyclic ring not having a line-symmetric axis and a rotational axis means that a ring structure composed solely of atoms forming the ring does not have a line-symmetric axis and a rotational axis.

The condensed aromatic heterocyclic ring not having a line-symmetric axis and a rotational axis has a number of carbon atoms of usually 6 to 20, and examples thereof include, for example, condensed rings obtained by condensation of an aromatic heterocyclic ring with an aromatic hydrocarbon ring such as a benzofuran ring, a benzothiophene ring, a benzoselenophene ring, a benzopyrrole ring, a naphthofuran ring, a naphthothiophene ring, a naphthoselenophene ring, an anthrafuran ring, an anthrathiophene ring, an anthraselenophene ring, a tetracenothiophene ring, a tetracenofuran ring, an indenothiophene ring, a quinoline ring and the like; and condensed rings obtained by condensation of an aromatic heterocyclic ring with an aromatic heterocyclic ring such as a thianofuran ring, a thienoselenophene ring, a selenofuran ring and the like.

The substituent which the aromatic heterocyclic ring represented by a ring C optionally has includes an alkyl group, a cycloalkyl group, an alkoxy group, a cycloalkoxy group, an alkylthio group, a cycloalkylthio group, an aryl group, a monovalent heterocyclic group, a halogen atom, a silyl group, an amino group, an alkenyl group, a cycloalkenyl group, an alkynyl group, a hydroxyl group, a nitro group, a cyano group, a carboxyl group, an alkylcarbonyl group, a cycloalkylcarbonyl group, an alkoxycarbonyl group or a cycloalkoxycarbonyl group. The definition and specific examples of the alkyl group, the cycloalkyl group, the alkoxy group, the cycloalkoxy group, the alkylthio group, the cycloalkylthio group, an aryl group, a monovalent heterocyclic group, a halogen atom, a silyl group, an amino group, an alkenyl group, a cycloalkenyl group, an alkynyl group, an alkylcarbonyl group, the cycloalkylcarbonyl group, the alkoxycarbonyl group or the cycloalkoxycarbonyl group as the substituent which the aromatic heterocyclic ring represented by a ring C optionally has are the same as the definition and specific examples of the alkyl group, the cycloalkyl group, the alkoxy group, the cycloalkoxy group, the alkylthio group, the cycloalkylthio group, the aryl group, the monovalent heterocyclic group, the halogen atom, the silyl group, the amino group, the alkenyl group, the cycloalkenyl group, the alkynyl group, the alkylcarbonyl group, the cycloalkylcarbonyl group, the alkoxycarbonyl group or the cycloalkoxycarbonyl group as the substituent which the heterocyclic ring represented by a ring A and a ring B optionally has. The aromatic heterocyclic ring represented by a ring C has no substituent, alternatively when the ring has a substituent, the substituent is preferably an alkyl group, a cycloalkyl group, an alkoxy group or a cycloalkoxy group, more preferably an alkyl group or an alkoxy group.

In the formula (1), $Z^1$ and $Z^2$ each independently represent a group represented by the formula (Z-1), a group represented by the formula (Z-2), a group represented by the formula (Z-3), a group represented by the formula (Z-4), a group represented by the formula (Z-5), a group represented by the formula (Z-6) or a group represented by the formula (Z-7).

[Chemical Formula 12]

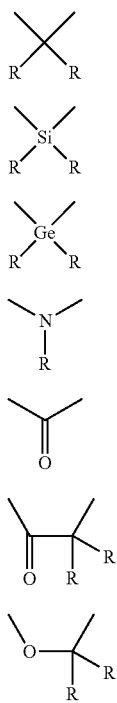

(Z-1)

(Z-2)

(Z-3)

(Z-4)

(Z-5)

(Z-6)

(Z-7)

It is preferable that $Z^1$ and $Z^2$ represent the same group, since synthesis of the polymer compound of the present invention is easy.

$Z^1$ and $Z^2$ represent preferably a group represented by the formula (Z-1), the formula (Z-2) or the formula (Z-3), more preferably a group represented by the formula (Z-1) or the formula (Z-2), further preferably a group represented by the formula (Z-1), since an organic transistor produced by using the polymer compound of the present invention is more excellent in carrier mobility.

In the formulae (Z-1) to (Z-7), R represents an alkyl group, a cycloalkyl group, an alkoxy group, a cycloalkoxy group, an alkylthio group, a cycloalkylthio group, an aryl group or a monovalent heterocyclic group, and these groups optionally have a substituent. When a plurality of R are present, they may be the same or different.

The definition and specific examples of the alkyl group, the cycloalkyl group, the alkoxy group, the cycloalkoxy group, the alkylthio group, the cycloalkylthio group, the aryl group and the monovalent heterocyclic group represented by R are the same as the definition and specific examples of the alkyl group, the cycloalkyl group, the alkoxy group, the cycloalkylthio group, the alkylthio group, the cycloalkylthio group, the aryl group and the monovalent heterocyclic group as the substituent which the heterocyclic ring represented by a ring A and a ring B optionally has.

R is preferably an alkyl group, a cycloalkyl group or an aryl group, more preferably an alkyl group, further preferably a linear alkyl group, since an organic transistor produced by using the polymer compound of the present invention is more excellent in carrier mobility.

In the formulae (Z-1) to (Z-3) and the formulae (Z-6) and (Z-7), it is preferable that two groups R are the same group, since synthesis of the polymer compound of the present invention is easy.

The structural unit represented by the formula (1) is preferably a structural unit represented by the formula (2), since synthesis of the polymer compound of the present invention is easy.

[Chemical Formula 13]

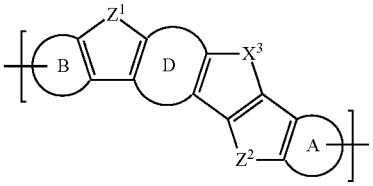

(2)

In the formula (2), a ring A, a ring B, $Z^1$ and $Z^2$ represent the same meaning as described above. $X^3$ represents an oxygen atom, a sulfur atom or a selenium atom.

In the formula (2), a ring D represents an aromatic hydrocarbon ring selected from the group consisting of a benzene ring and a condensed ring obtained by condensation of 2 to 4 benzene rings (namely, an aromatic hydrocarbon ring constituted of 1 to 4 benzene rings), and the aromatic hydrocarbon ring optionally has a substituent.

The aromatic hydrocarbon ring selected from the group consisting of a benzene ring and a condensed ring obtained by condensation of 2 to 4 benzene rings has a number of carbon atoms of 6 to 18, and examples thereof include, for example, a benzene ring; and condensed rings obtained by condensation of 2 to 4 benzene rings such as a naphthalene ring, an anthracene ring, a phenanthrene ring, a chrysene ring, a pyrene ring and the like.

The substituent which the aromatic hydrocarbon ring represented by a ring D optionally has includes a hydrogen atom, an alkyl group, a cycloalkyl group, an alkoxy group, a cycloalkoxy group, an alkylthio group, a cycloalkylthio group, an aryl group, a monovalent heterocyclic group, a halogen atom, a silyl group, an amino group, an alkenyl group, a cycloalkenyl group, an alkynyl group, a hydroxyl group, a nitro group, a cyano group, a carboxyl group, an alkylcarbonyl group, a cycloalkylcarbonyl group, an alkoxycarbonyl group or a cycloalkoxycarbonyl group. The definition and specific examples of the alkyl group, the cycloalkyl group, the alkoxy group, the cycloalkoxy group, the alkylthio group, the cycloalkylthio group, the aryl group, the monovalent heterocyclic group, the halogen atom, the silyl group, the amino group, the alkenyl group, the cycloalkenyl group, the alkynyl group, the alkylcarbonyl group, the cycloalkylcarbonyl group, the alkoxycarbonyl group or the cycloalkoxycarbonyl group as the substituent which the aromatic hydrocarbon ring represented by a ring D optionally has are the same as the definition and specific examples of the alkyl group, the cycloalkyl group, the alkoxy group, the cycloalkoxy group, the alkylthio group, the cycloalkylthio group, the aryl group, the monovalent heterocyclic group, the halogen atom, the silyl group, the amino group, the alkenyl group, the cycloalkenyl group, the alkynyl group, the alkylcarbonyl group, the cycloalkylcarbonyl group, the alkoxycarbonyl group or the cycloalkoxycarbonyl group as the substituent which the heterocyclic ring represented by a ring A and a ring B optionally. The aromatic hydrocarbon ring represented by a ring D has no substituent, alternatively when the ring has a substituent, the substituent is preferably an alkyl group, a cycloalkyl group, an alkoxy group or a cycloalkoxy group, more preferably an alkyl group or an alkoxy group.

$X^3$ is preferably a sulfur atom or an oxygen atom, more preferably a sulfur atom, since an organic transistor produced by using the polymer compound of the present invention is more excellent in carrier mobility.

The structural unit represented by the formula (2) is preferably a structural unit represented by the formula (2-1), since synthesis of the polymer compound of the present invention is easy.

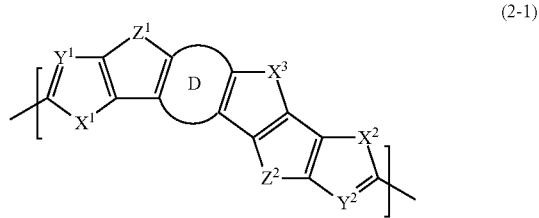

(2-1)

In the formula (2-1), $X^3$, $Z^1$, $Z^2$ represent the same meaning as described above.

$X^1$ and $X^2$ each independently represent an oxygen atom, a sulfur atom or a selenium atom. $Y^1$ represents a nitrogen atom or a group represented by $-CR^5=$, and $Y^2$ represents a nitrogen atom or a group represented by $-CR^6=$. $R^5$ and $R^6$ each independently represent a hydrogen atom, an alkyl group, a cycloalkyl group, an alkoxy group, a cycloalkoxy group, an alkylthio group, a cycloalkylthio group, an aryl group, a monovalent heterocyclic group or a halogen atom.

The definition and specific examples of the alkyl group, the cycloalkyl group, the alkoxy group, the cycloalkylthio group, the alkylthio group, the cycloalkylthio group, the aryl group, the monovalent heterocyclic group and the halogen atom represented by $R^5$ and $R^6$ are the same as the definition and specific examples of the alkyl group, the cycloalkyl group, the alkoxy group, the cycloalkylthio group, the alkylthio group, the cycloalkylthio group, the aryl group, the monovalent heterocyclic group and the halogen atom as the substituent which the heterocyclic ring represented by a ring A and a ring B optionally has.

$X^1$ and $X^2$ represent preferably a sulfur atom or an oxygen atom, more preferably a sulfur atom, since an organic transistor produced by using the polymer compound of the present invention is more excellent in carrier mobility. It is preferable that $Y^1$ and $Y^2$ represent $-CR^5=$ and $-CR^6=$, it is more preferable that both of them represent $-CH=$.

The structural unit represented by the formula (2) is preferably a structural unit represented by the formula (3), since synthesis of the polymer compound of the present invention is easy.

[Chemical Formula 14]

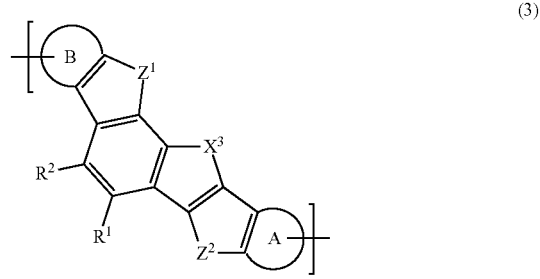

(3)

In the formula (3), a ring A, a ring B, $X^3$, $Z^1$ and $Z^2$ represent the same meaning as described above.

$R^1$ and $R^2$ each independently represent a hydrogen atom, an alkyl group, a cycloalkyl group, an alkoxy group, a cycloalkoxy group, an alkylthio group, a cycloalkylthio group, an aryl group, a monovalent heterocyclic group, a halogen atom, a silyl group, an amino group, an alkenyl group, a cycloalkenyl group, an alkynyl group, a hydroxyl group, a nitro group, a cyano group, a carboxyl group, an alkylcarbonyl group, a cycloalkylcarbonyl group, an alkoxycarbonyl group or a cycloalkoxycarbonyl group, and of these groups, an alkyl group, a cycloalkyl group, an alkoxy group, a cycloalkoxy group, an alkylthio group, a cycloalkylthio group, an aryl group, a monovalent heterocyclic group, a silyl group, an amino group, an alkenyl group, a cycloalkenyl group, an alkynyl group, an alkylcarbonyl group, a cycloalkylcarbonyl group, an alkoxycarbonyl group and a cycloalkoxycarbonyl group each optionally have a substituent.

The definition and specific examples of the alkyl group, the cycloalkyl group, the alkoxy group, the cycloalkoxy group, the alkylthio group, the cycloalkylthio group, the aryl group, the monovalent heterocyclic group, the halogen atom, the silyl group, the amino group, the alkenyl group, the cycloalkenyl group, the alkynyl group, the alkylcarbonyl group, the cycloalkylcarbonyl group, the alkoxycarbonyl group or the cycloalkoxycarbonyl group represented by $R^1$ and $R^2$ are the same as the definition and specific examples of the alkyl group, the cycloalkyl group, the alkoxy group, the cycloalkoxy group, the alkylthio group, the cycloalkylthio group, the aryl group, the monovalent heterocyclic group, the halogen atom, the silyl group, the amino group, the alkenyl group, the cycloalkenyl group, the alkynyl group, the alkylcarbonyl group, the cycloalkylcarbonyl group, the alkoxycarbonyl group or the cycloalkoxycarbonyl group which the heterocyclic ring represented by a ring A and a ring B optionally has.

$R^1$ and $R^2$ represent preferably a hydrogen atom, an alkyl group, a cycloalkyl group, an alkoxy group or a cycloalkoxy group, further preferably an alkyl group or an alkoxy group, since an organic transistor produced by using the polymer compound of the present invention is more excellent in carrier mobility.

The structural unit represented by the formula (3) is preferably a structural unit represented by the formula (4), since synthesis of the polymer compound of the present invention is easy.

[Chemical Formula 15]

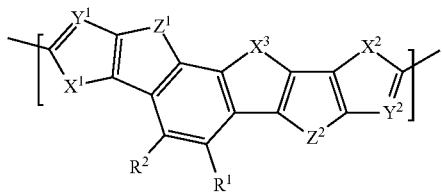

(4)

In the formula (4), $X^1$, $X^2$, $X^3$, $Z^1$, $Z^2$, $R^1$ and $R^2$ represent the same meaning as described above.

$Y^1$ represents a nitrogen atom or a group represented by —$CR^5$=, and $Y^2$ represents a nitrogen atom or a group represented by —$CR^6$=. $R^5$ and $R^6$ each independently represent a hydrogen atom, an alkyl group, a cycloalkyl group, an alkoxy group, a cycloalkoxy group, an alkylthio group, a cycloalkylthio group, an aryl group, a monovalent heterocyclic group or a halogen atom. The definition and specific examples of the alkyl group, the cycloalkyl group, the alkoxy group, the cycloalkoxy group, the alkylthio group, the cycloalkylthio group, the aryl group, the monovalent heterocyclic group and the halogen atom represented by $R^5$ and $R^6$ are the same as the definition and specific examples of the alkyl group, the cycloalkyl group, the alkoxy group, the cycloalkoxy group, the alkylthio group, the cycloalkylthio group, the aryl group, the monovalent heterocyclic group and the halogen atom as the substituent which the heterocyclic ring represented by a ring A and a ring B optionally has.

The structural unit represented by the formula (1) includes, for example, structural units represented by the formula (1-1) to the formula (1-35).

The structural unit represented by the formula (1) is preferably a structural unit represented by the formula (1-1) to the formula (1-23), more preferably a structural unit represented by the formula (1-1) to the formula (1-13), further preferably a structural unit represented by the formula (1-1) to the formula (1-8), since an organic transistor produced by using the polymer compound of the present invention is more excellent in carrier mobility.

[Chemical Formula 16]

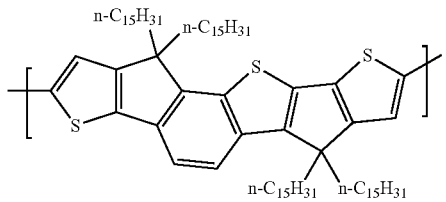

(1-2)

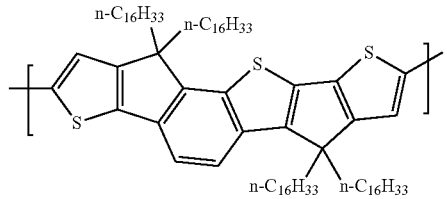

(1-3)

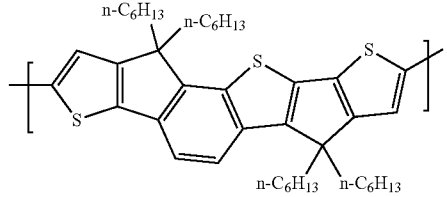

(1-4)

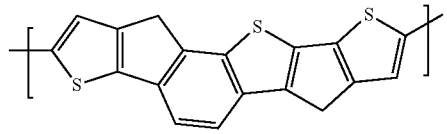

(1-5)

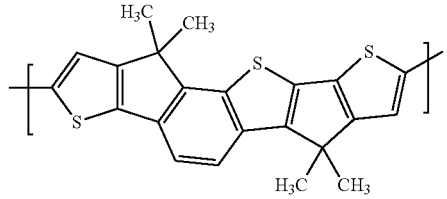

(1-6)

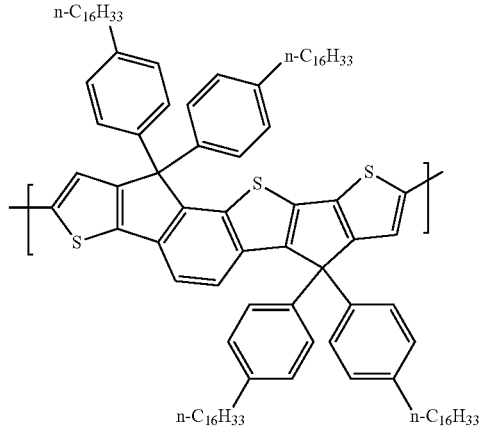

(1-7)

-continued
[Chemical Formula 17]
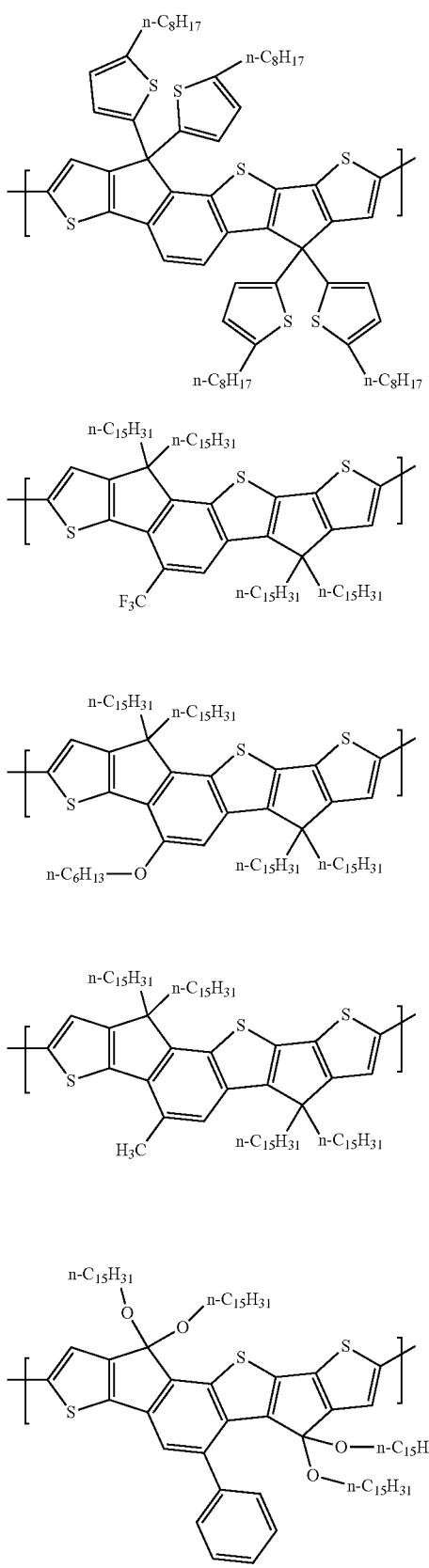
(1-8)
(1-9)
(1-10)
(1-11)
(1-12)
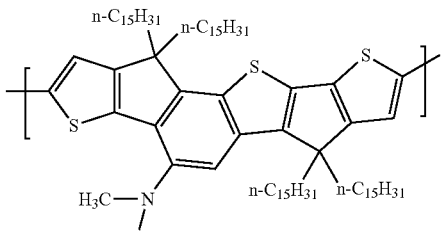
(1-13)
[Chemical Formula 18]
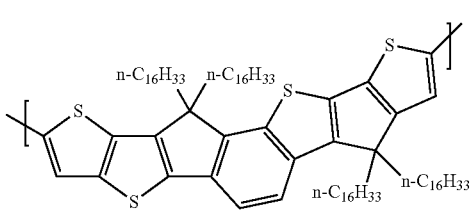
(1-14)
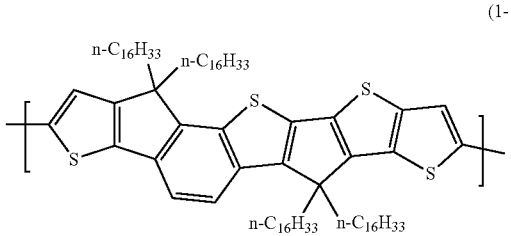
(1-15)
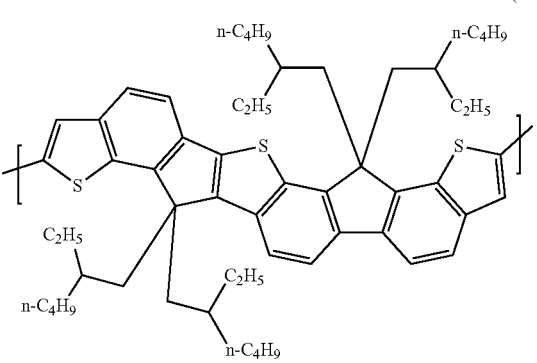
(1-16)
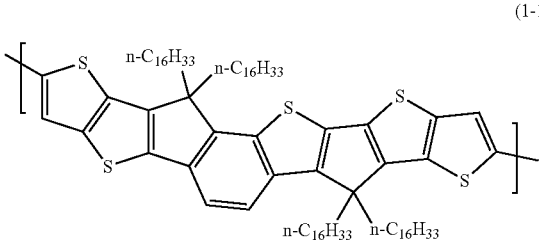
(1-17)
[Chemical Formula 19]
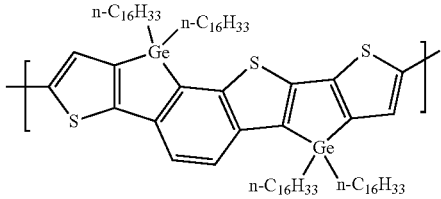
(1-18)

(1-19) 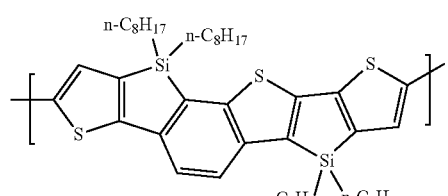
(1-20) 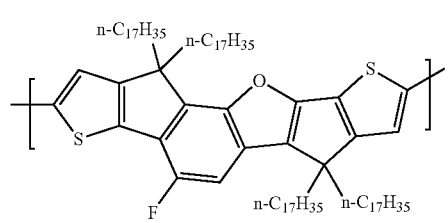
(1-21) 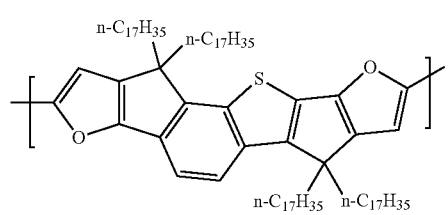
(1-22) 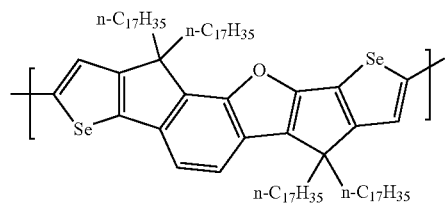
(1-23) 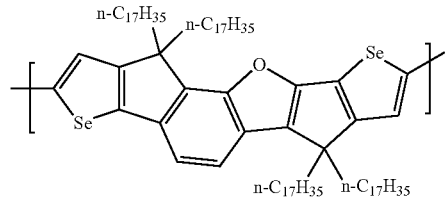
[Chemical Formula 20]
(1-24) 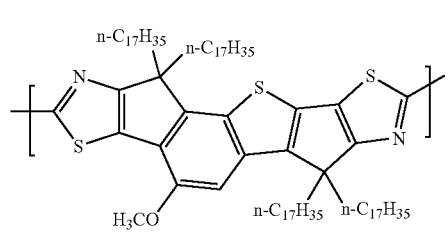
(1-25) 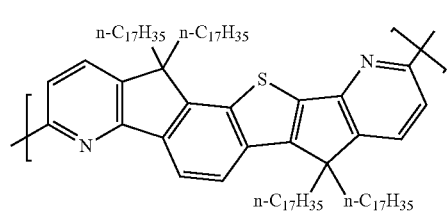
(1-26) 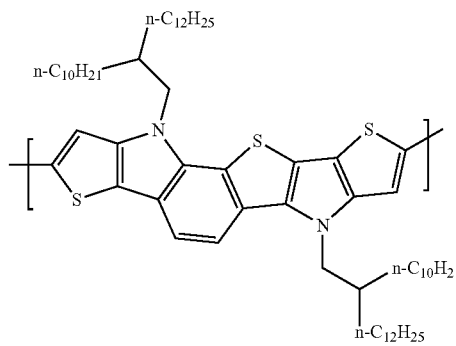
(1-27) 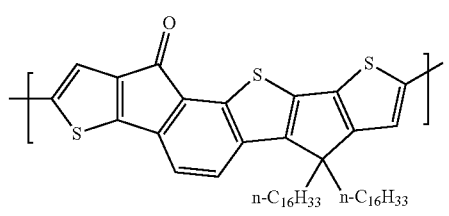
(1-28) 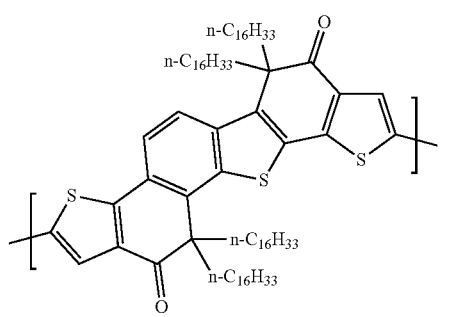
(1-29) 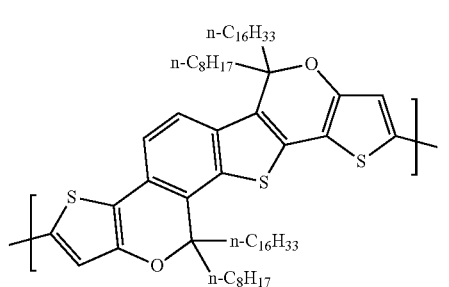
[Chemical Formula 21]
(1-30) 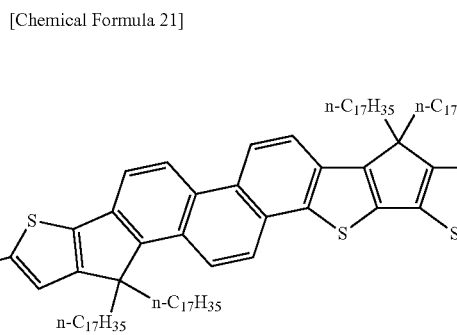

-continued

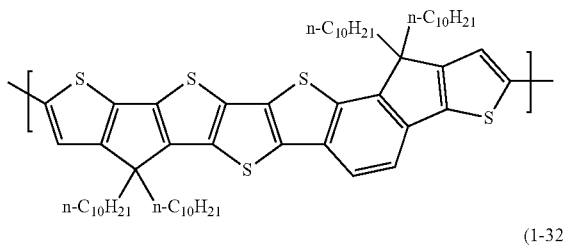
(1-31)

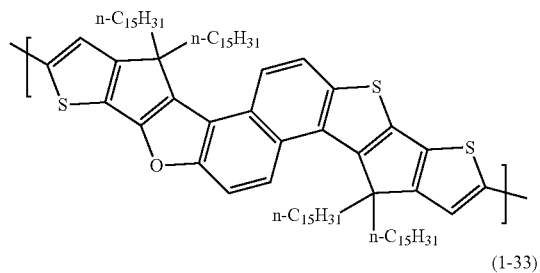
(1-32)

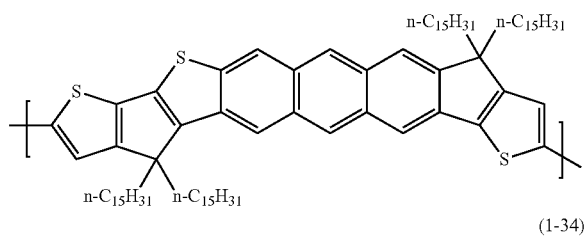
(1-33)

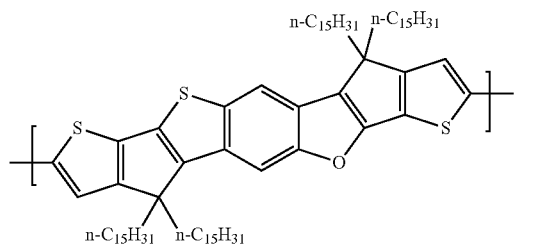
(1-34)

(1-35)

(Second Structural Unit)

It is preferable that the polymer compound of the present invention further contains a structural unit represented by the formula (5) (different from the structural unit represented by the formula (1) described above) (hereinafter, referred to as "second structural unit" in some cases) in addition to the structural unit represented by the formula (1). The second structural units may be contained each singly or two or more of them may be contained in the polymer compound.

When the polymer compound of the present invention contains a second structural unit, the mole fraction of the second structural unit is preferably 20 to 80 mol %, more preferably 40 to 60 mol % with respect to the total amount of the first structural unit and the second structural unit.

[Chemical Formula 22]

$$-\!\!\!+\!\!Ar\!\!+\!\!-$$ (5)

In the formula (5), Ar represents an arylene group or a divalent heterocyclic group, and these groups optionally have a substituent.

When the polymer compound of the present invention contains a second structural unit, it is preferable that a structural unit represented by the formula (1) and a structural unit represented by the formula (5) are conjugated.

The arylene group is an atomic group remaining after removing from an aromatic hydrocarbon two hydrogen atoms bonding directly to carbon atoms constituting the ring and includes a group having a condensed ring, a group obtained by directly bonding two or more groups selected from the group consisting of an independent benzene ring and a condensed ring and a group obtained by bonding two or more groups selected from the group consisting of an independent benzene ring and a condensed ring via vinylene and the like. The arylene group has a number of carbon atoms of usually 6 to 60, preferably 6 to 20. The number of carbon atoms does not include the number of carbon atoms of the substituent which the arylene group described later optionally has.

The arylene group optionally has a substituent, and the substituent includes, for example, an alkyl group, a cycloalkyl group, an alkoxy group, a cycloalkoxy group, an alkylthio group, a cycloalkylthio group, a monovalent heterocyclic group and a halogen atom. The definition and specific examples of these substituents are the same as the definition and specific examples of the alkyl group, the cycloalkyl group, the alkoxy group, the cycloalkoxy group, the alkylthio group, the cycloalkylthio group, the monovalent heterocyclic group and the halogen atom as the substituent which the heterocyclic ring represented by a ring A and a ring B optionally has.

The arylene group includes, for example, arylene groups represented by the following formulae 1 to 12.

[Chemical Formula 23]

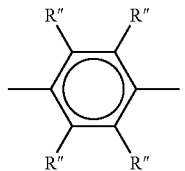 1

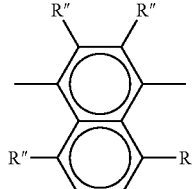 2

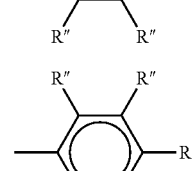 3

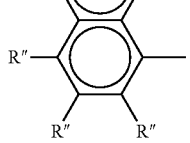

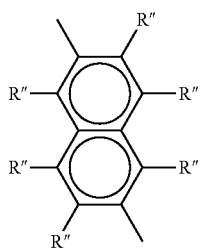
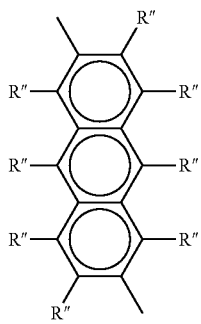
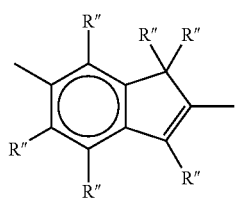

[Chemical Formula 24]

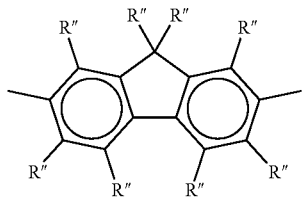
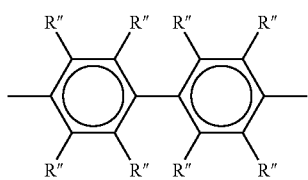
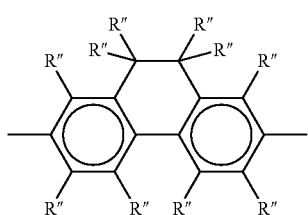
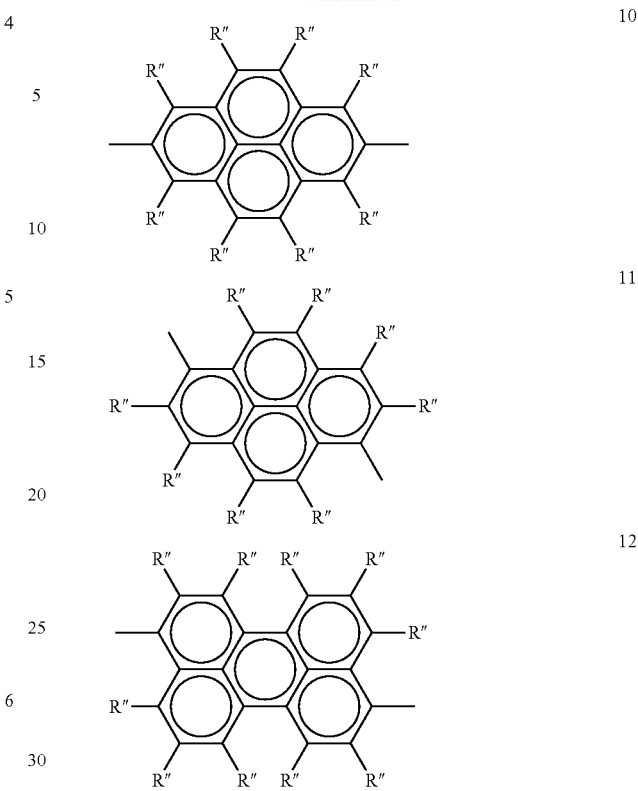

In the formulae 1 to 12, R″ represents a hydrogen atom, an alkyl group, a cycloalkyl group, an alkoxy group, a cycloalkoxy group, an alkylthio group, a cycloalkylthio group, an aryl group, a monovalent heterocyclic group or a halogen atom. A plurality of R″ may be the same or different.

The definition and specific examples of the alkyl group, the cycloalkyl group, the alkoxy group, the cycloalkoxy group, the alkylthio group, the cycloalkylthio group, the aryl group, the monovalent heterocyclic group and the halogen atom represented by R″ are the same as the definition and specific examples of the alkyl group, the cycloalkyl group, the alkoxy group, the cycloalkoxy group, the alkylthio group, the cycloalkylthio group, the aryl group, the monovalent heterocyclic group and the halogen atom as the substituent which the heterocyclic ring represented by a ring A and a ring B optionally has.

The divalent heterocyclic group is an atomic group remaining after removing from a heterocyclic compound two hydrogen atoms bonding directly to carbon atoms or hetero atoms constituting the ring, and includes a group having a condensed ring and a group obtained by directly bonding two or more groups selected from the group consisting of an independent heterocyclic group and a condensed ring. The divalent heterocyclic group has a number of carbon atoms of usually 2 to 30, preferably 3 to 20. The number of carbon atoms does not include the number of carbon atoms of the substituent which the divalent heterocyclic group described later optionally has. The divalent heterocyclic group is preferably a divalent aromatic heterocyclic group.

The divalent heterocyclic group optionally has a substituent, and the substituent includes, for example, an alkyl group, a cycloalkyl group, an alkoxy group, a cycloalkoxy group, an alkylthio group, a cycloalkylthio group, an aryl group and a halogen atom. The definition and specific examples of these substituents are the same as the definition and specific examples of the alkyl group, the cycloalkyl group, the alkoxy group, the cycloalkoxy group, the alkylthio group, the cycloalkylthio group, the aryl group and the halogen atom as the substituent which the heterocyclic ring represented by a ring A and a ring B optionally has.

The divalent heterocyclic group includes, for example, divalent heterocyclic groups represented by the following formulae 13 to 66.

[Chemical Formula 25]

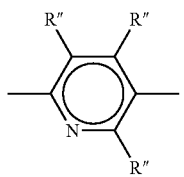
13

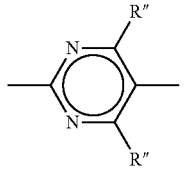
14

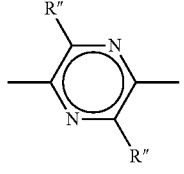
15

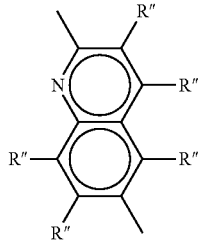
16

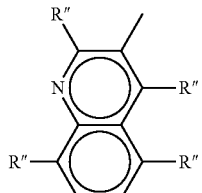
17

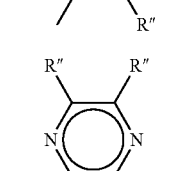
18

[Chemical Formula 26]

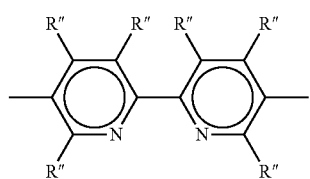
19

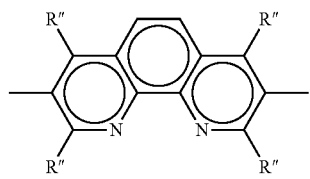
20

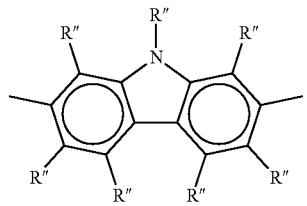
21

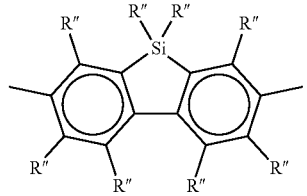
22

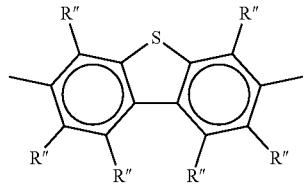
23

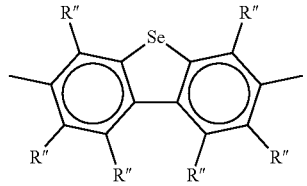
24

[Chemical Formula 27]

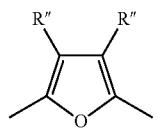
25

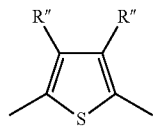
26

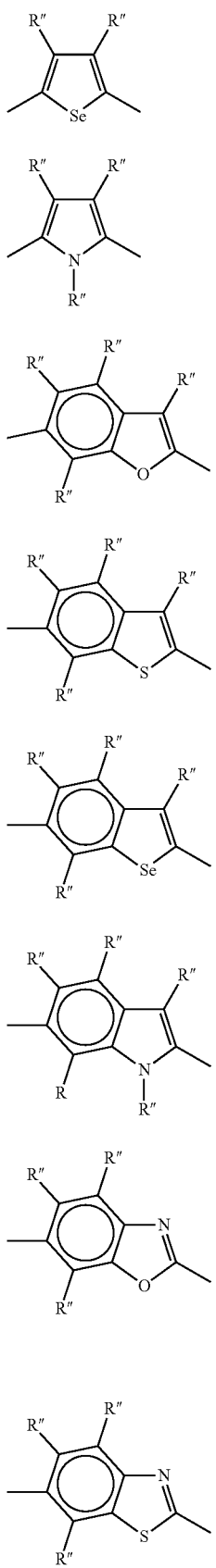
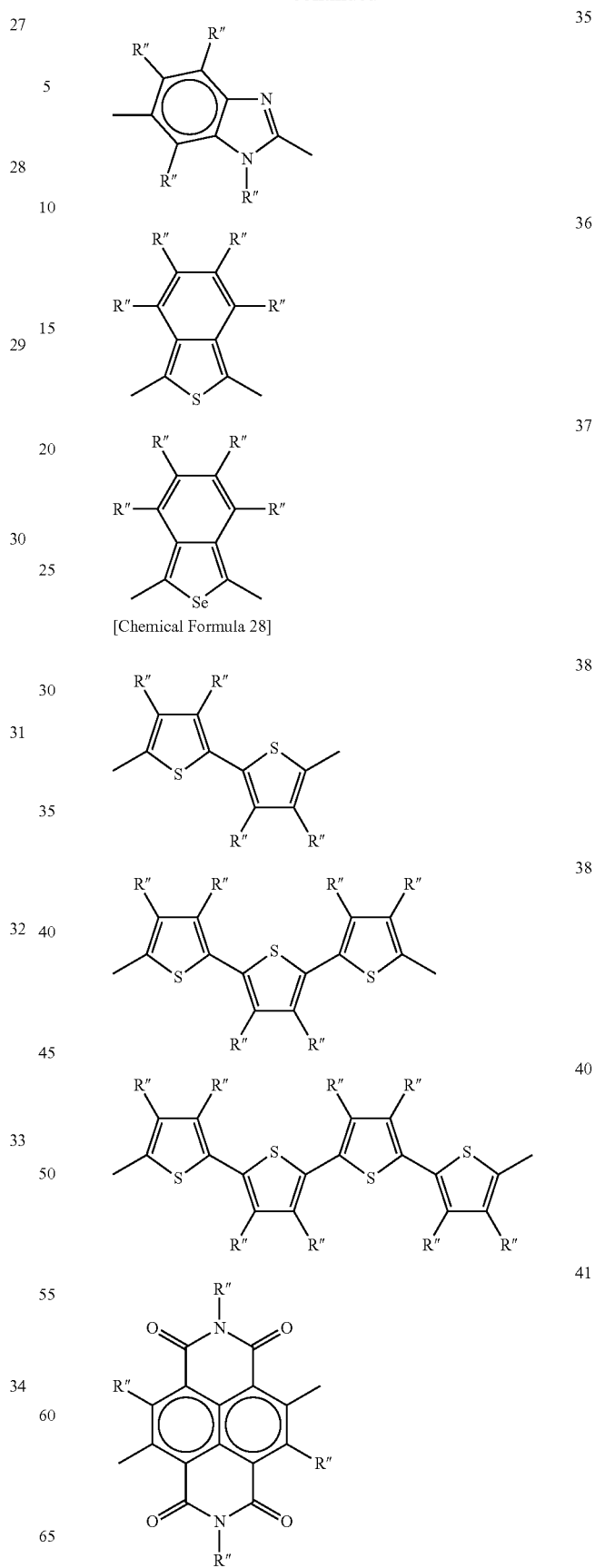
[Chemical Formula 28]

-continued
[Chemical Formula 29]
42
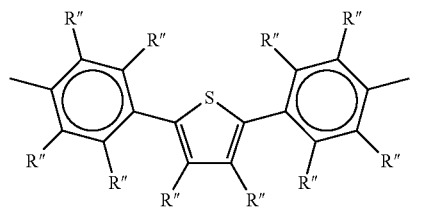
43
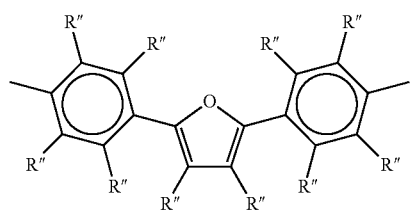
44
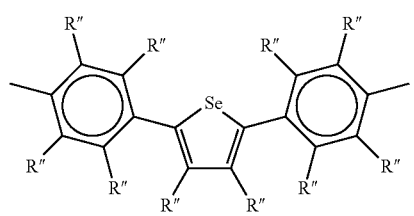
45
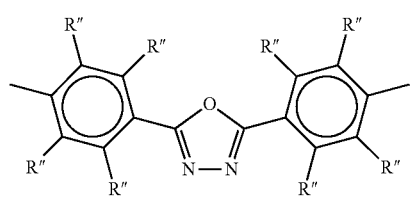
46
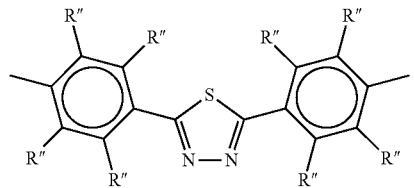
47
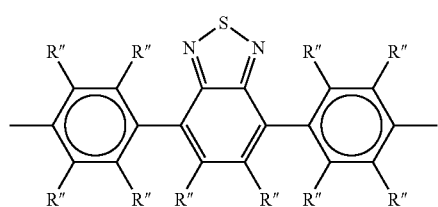
48
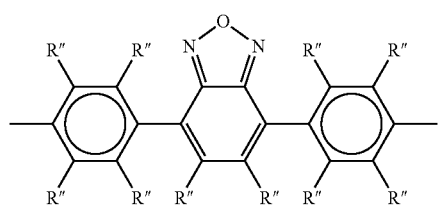
-continued
[Chemical Formula 30]
49
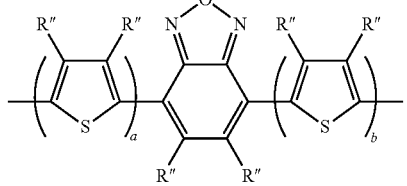
50
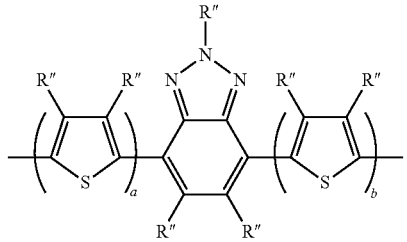
51
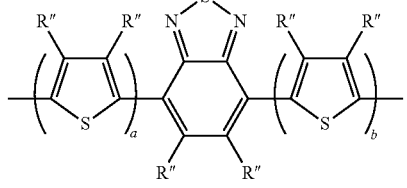
52
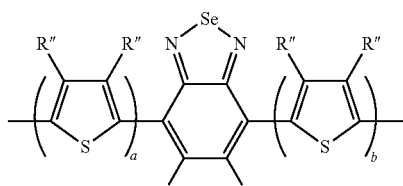
53
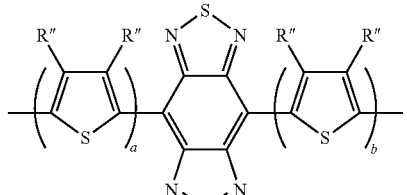
[Chemical Formula 31]
54
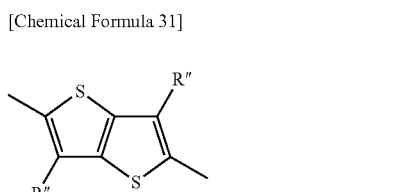
55
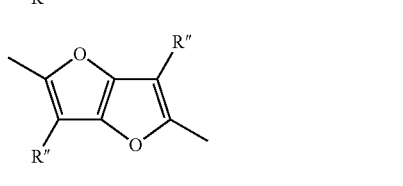
56
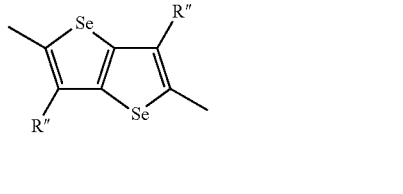

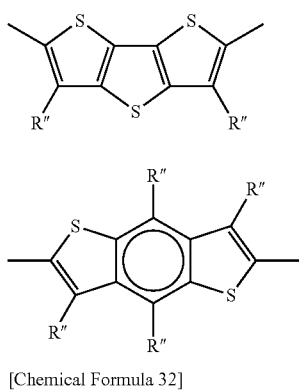

[Chemical Formula 32]

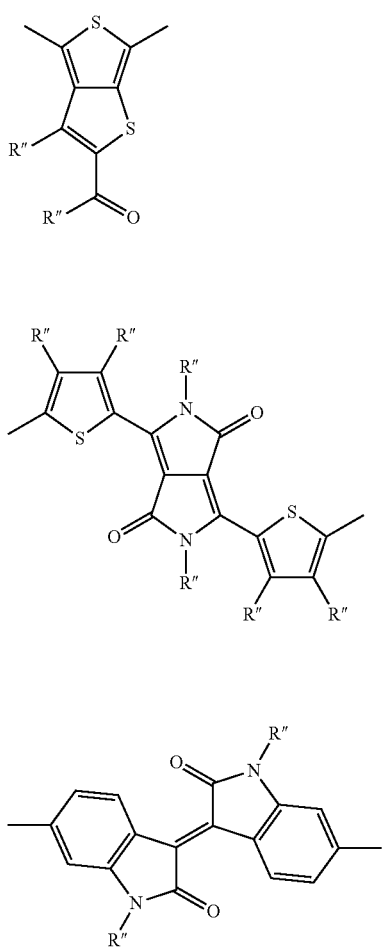

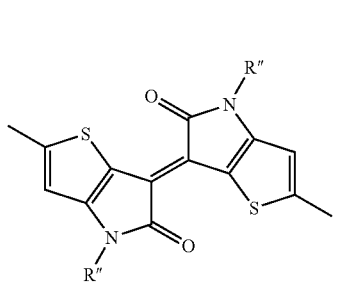

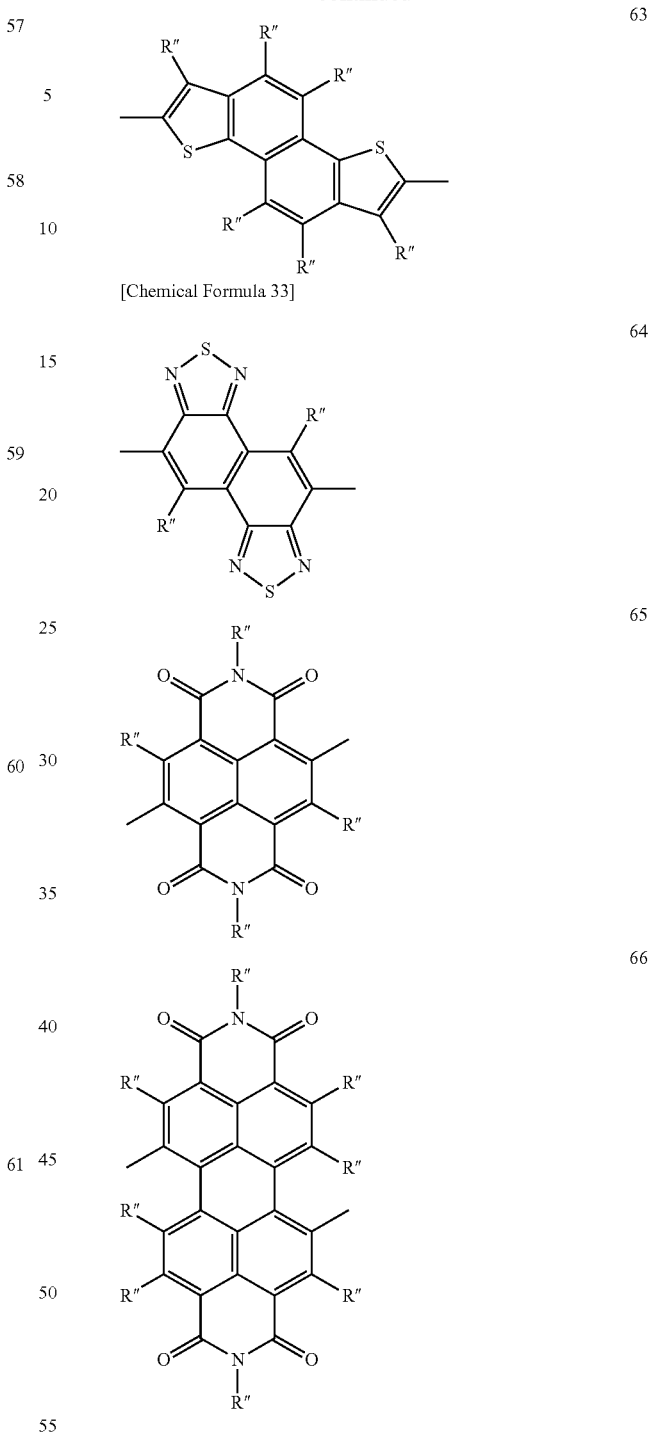

[Chemical Formula 33]

In the formulae 13 to 66, R" represents the same meaning as described above. a and b each independently represent the number of repetition, and usually an integer of 0 to 5, preferably an integer of 0 to 3, more preferably an integer of 0 to 1.

The second structural unit is preferably a divalent heterocyclic group, more preferably a divalent heterocyclic group selected from the formula 49 to the formula 53, the formulae 59 to 62 and the formulae 64 to 66, further preferably a divalent heterocyclic group represented by the formula 51 and/or the formula 64, since an organic transistor produced by using the polymer compound of the present invention is more excellent in carrier mobility.

(Other Structural Unit)

The polymer compound of the present invention may contain other structural units than the first structural unit and the second structural unit described above (hereinafter, referred to as "other structural unit" in some cases). The other structural units may be contained each singly or two or more of them may be contained in the polymer compound.

The other structural unit includes, for example, a group represented by —$CR^c$=$CR^d$—, —C≡C—, a group represented by the formula: —$CR^g{}_2$—, a group represented by the formula: —C(=O)— and a group represented by the formula: —C(=O)O—.

In the group represented by —$CR^c$=$CR^d$—, $R^c$, $R^d$ and $R^g$ each independently represent a hydrogen atom, an alkyl group, a cycloalkyl group, an aryl group, a monovalent aromatic heterocyclic group, a halogen atom or a cyano group, and of these groups, an alkyl group, a cycloalkyl group, an aryl group and a monovalent aromatic heterocyclic group each optionally have a substituent.

The substituent which $R^c$, $R^d$ and $R^g$ optionally have includes an alkyl group, a cycloalkyl group, an alkoxy group, a cycloalkoxy group, an alkylthio group, a cycloalkylthio group, an aryl group, a monovalent aromatic heterocyclic group, a halogen atom and the like, and of them, an alkyl group is preferable.

(Polymer Compound)

The polymer compound of the present invention is preferably a conjugated polymer compound, since more excellent carrier mobility is obtained.

In the polymer compound of the present invention, it is recommendable that at least one first structural unit (a structural unit represented by the formula (1)) is contained in the polymer compound, and it is preferable that three or more first structural units are contained in the polymer compound, it is more preferable that five or more first structural units are contained in the polymer compound.

In the polymer compound of the present invention, the total mole fraction of a first structural unit and a second structural unit with respect to all structural units constituting the polymer compound is preferably 50 mol % or more, more preferably 70 mol % or more, since more excellent carrier mobility is obtained. The upper limit of the total mole fraction of a first structural unit and a second structural unit with respect to all structural units constituting the polymer compound is 100 mol %.

When a group showing activity on the polymerization reaction remains at the end of the molecular chain of the polymer compound of the present invention, there is a possibility of lowering of carrier mobility. Therefore, it is preferable that the end of the molecular chain is composed of a stable group such as an aryl group, a monovalent aromatic heterocyclic group and the like.

The polymer compound of the present invention has a polystyrene-equivalent number-average molecular weight (Mn) of usually $1×10^3$ to $1×10^8$ and a polystyrene-equivalent weight-average molecular weight (Mw) of usually $1×10^3$ to $2×10^8$, each measured by gel permeation chromatography (hereinafter, referred to as "GPC"). The number-average molecular weight is preferably $1×10^3$ or more and the weight-average molecular weight is preferably $1×10^3$ or more, from the standpoint of forming a good film in film fabrication. The number-average molecular weight is preferably $1×10^6$ or less and the weight-average molecular weight is preferably $1×10^6$ or less, from the standpoint of solubility and film formability.

The polymer compound of the present invention is one having high solubility in a solvent (preferably, an organic solvent), and specifically, it is preferable that it has solubility by which a solution containing the polymer compound of the present invention in an amount of 0.1 wt % or more can be prepared, it is more preferable that it has solubility by which a solution containing the polymer compound of the present invention in an amount of 0.4 wt % or more can be prepared.

The polymer compound of the present invention may be a homopolymer or a copolymer.

The polymer compound of the present invention may be any kind of copolymer, and for example, may be any of a block copolymer, a random copolymer, an alternate copolymer and a graft copolymer. The polymer compound of the present invention is preferably a copolymer of a structural unit represented by the formula (1) and a structural unit represented by the formula (5), more preferably an alternate copolymer of a structural unit represented by the formula (1) and a structural unit represented by the formula (5), since an organic transistor produced by using the polymer compound of the present invention is more excellent in carrier mobility. When a plurality of structural units represented by the formula (1) are present in the copolymer, they may be the same or different, and when a plurality of structural units represented by the formula (5) are present in the copolymer, they may be the same or different.

Specific examples of the alternate copolymer of a structural unit represented by the formula (1) and a structural unit represented by the formula (5) of the present invention include polymer compounds represented by the formula (P-1) to the formula (P-13). m represents an integer of 2 or more. Of them, polymer compounds represented by the formula (P-1) to the formula (P-9) are preferable, polymer compounds represented by the formula (P-1) to the formulae (P-5) and (P-8) are more preferable, since more excellent carrier mobility is obtained.

[Chemical Formula 34]

(P-1)

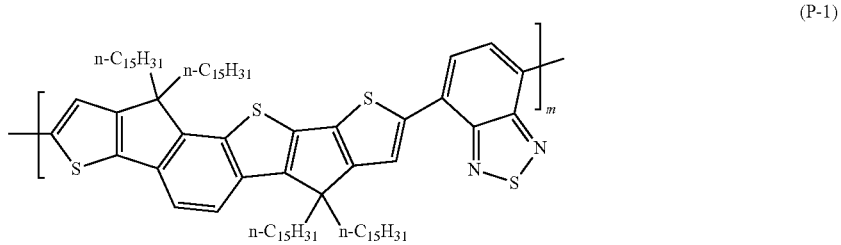

(P-2)
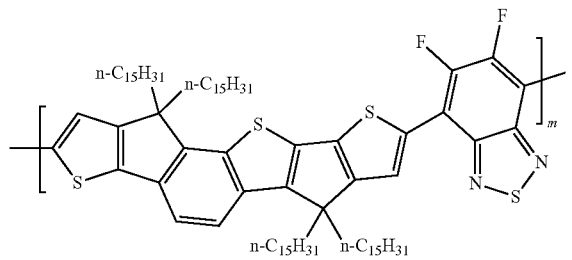
(P-3)
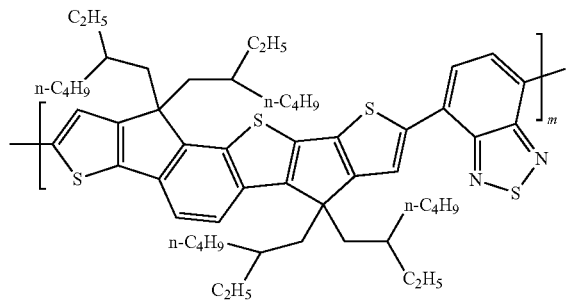
(P-4)
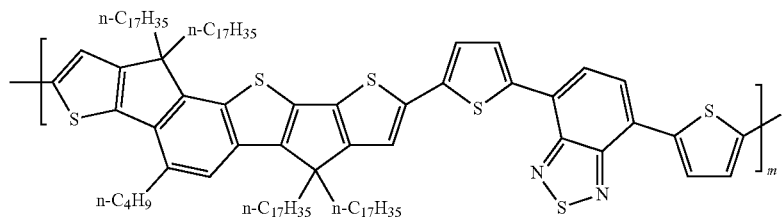
(P-5)
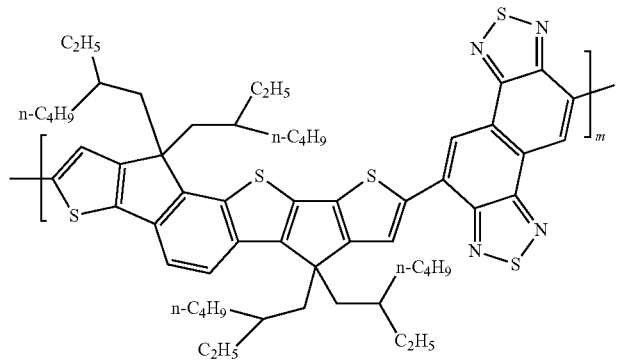
[Chemical Formula 35]
(P-6)
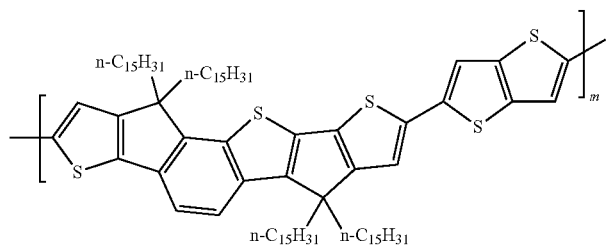

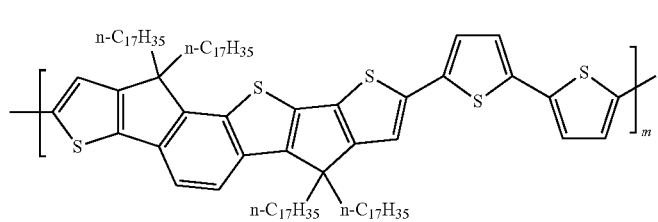
(P-7)
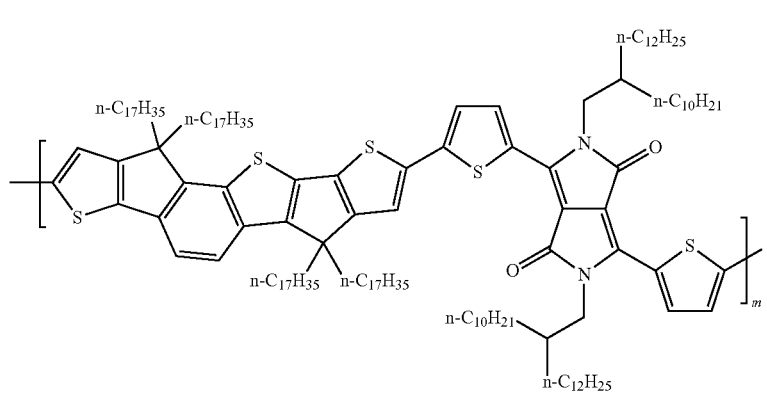
(P-8)
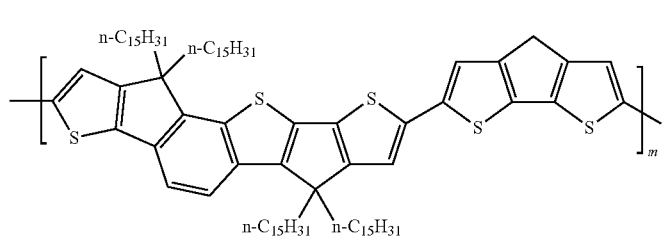
(P-9)
[Chemical Formula 36]
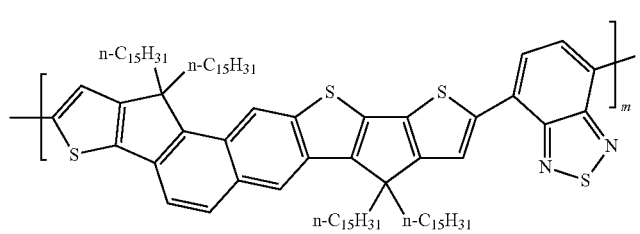
(P-10)
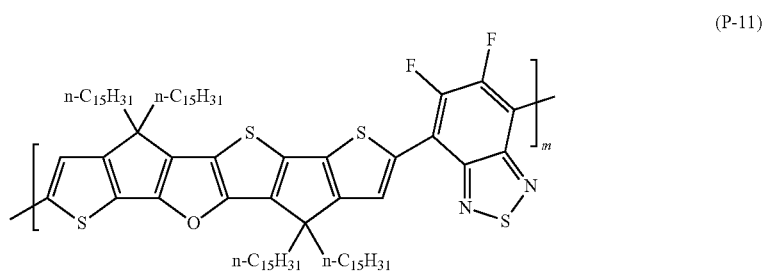
(P-11)
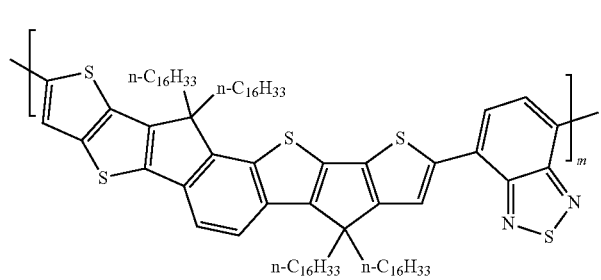
(P-12)

-continued

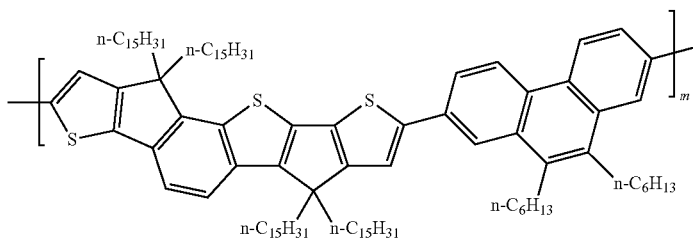
(P-13)

<Production Method of Polymer Compound>

Next, a method of producing the polymer compound of the present invention will be illustrated.

The polymer compound of the present invention may be produced by any method, and for example, a compound represented by the formula: $X^{11}$-$A^{11}$-$X^{12}$ and a compound represented by the formula: $X^{13}$-$A^{12}$-$X^{14}$ are, if necessary, dissolved in an organic solvent, with addition of a base as needed, subjected to known polymerization methods such as aryl coupling and the like using a suitable catalyst, thus, the polymer compound can be synthesized.

$A^{11}$ represents a structural unit represented by the formula (1), and $A^{12}$ represents a structural unit represented by the formula (5). $X^{11}$, $X^{12}$, $X^{13}$ and $X^{14}$ each independently represent a polymerization reactive group.

The polymerization reactive group includes, for example, a halogen atom, a borate residue, a boric acid residue, and an organotin residue substituted with three alkyl groups. The boric acid residue denotes a group represented by —$B(OH)_2$.

The halogen atom as the polymerization reactive group includes, for example, a fluorine atom, a chlorine atom, a bromine atom and an iodine atom.

The borate residue as the polymerizable functional group denotes an atomic group obtained by removing from an ester of boronic acid ($HB(OH)_2$) a hydrogen atom bonded to its boron. The borate residue has a number of carbon atoms of usually 2 to 40. The borate residue includes, for example, groups represented by the following formulae.

[Chemical Formula 37]

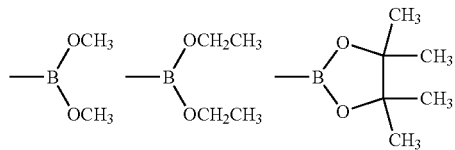

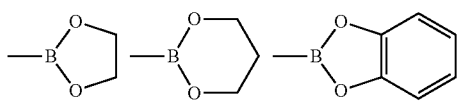

[Chemical Formula 38]

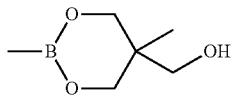

The organotin residue substituted with three alkyl groups (trialkyl stannyl group) as the polymerization reactive group includes, for example, an organotin residue substituted with three methyl groups and an organotin residue substituted with three butyl groups. The organotin residue has a number of carbon atoms of usually 3 to 60.

The polymerization method such as aryl coupling and the like includes, for example, a method of polymerization by the Suzuki coupling reaction (Chemical Review, 1995, vol. 95, pp. 2457-2483) and a method of polymerization by the Stille coupling reaction (European Polymer Journal, 2005, vol. 41, pp. 2923-2933).

In the case of use of a nickel catalyst or a palladium catalyst such as in the Suzuki coupling reaction and the like, the polymerization reactive group is preferably a halogen atom, a borate residue or a boric acid residue, it is more preferably a bromine atom, an iodine atom or a borate residue since the polymerization reaction is simplified.

When the polymer compound of the present invention is polymerized by the Suzuki coupling reaction, the ratio of the total molar number of a bromine atom and an iodine atom as the polymerization reactive group to the total molar number of a borate residue as the polymerization reaction group is preferably 0.7 to 1.3, more preferably 0.8 to 1.2.

In the case of use of a palladium catalyst such as in the Stille coupling reaction and the like, the polymerization reactive group is preferably a halogen atom or an organotin residue substituted with three alkyl groups, and it is preferably a bromine atom, an iodine atom or an organotin residue substituted with three alkyl groups, since the polymerization reaction is simplified.

When the polymer compound of the present invention is polymerized by the Stille coupling reaction, the ratio of the total molar number of a bromine atom and an iodine atom as the polymerization reactive group to the total molar number of an organotin residue substituted with three alkyl groups as the polymerization reactive group is preferably 0.7 to 1.3, more preferably 0.8 to 1.2.

The organic solvent used in polymerization includes, for example, benzene, toluene, xylene, chlorobenzene, dichlorobenzene, tetrahydrofuran and dioxane. These organic solvents may be used each singly or two or more of them may be used in combination.

The base used in polymerization includes, for example, inorganic bases such as sodium carbonate, potassium carbonate, cesium carbonate, potassium fluoride, cesium fluoride, tripotassium phosphate and the like, and organic bases such as tetrabutylammonium fluoride, tetrabutylammonium chloride, tetrabutylammonium bromide, tetraethylammonium hydroxide, tetrabutylammonium hydroxide and the like.

The catalyst used in polymerization is preferably a catalyst composed of a transition metal complex such as a palladium complex such as tetrakis(triphenylphosphine)palladium, tris(dibenzylideneacetone)dipalladium, palladium acetate, dichlorobistriphenylphosphinepalladium and the like, and if necessary, a ligand such as triphenylphosphine, tri-tert-butylphosphine, tricyclohexylphosphine and the like. As these catalysts, those previously synthesized may be used, or those prepared in the reaction system may be used as they are. These catalysts may be used each singly or two or more of them may be used in combination.

The reaction temperature of polymerization is preferably 0 to 200° C., more preferably 0 to 150° C., further preferably 0 to 120° C.

The reaction time of polymerization is usually 1 hour or more, preferably 2 to 500 hours.

The post treatment of polymerization can be conducted by a known method, and there is, for example, a method in which the reaction liquid obtained in the polymerization is added to a lower alcohol such as methanol and the like to cause deposition of a precipitate which is then filtrated and dried.

When the purity of the polymer compound of the present invention is low, it is preferable to purify the polymer compound by a method such as recrystallization, continuous extraction with a Soxhlet extractor, column chromatography and the like.

<Compound>

The compound of the present invention is a compound represented by the formula (6) and can be suitably used as a raw material of the polymer compound of the present invention in the above-described polymer compound production method.

[Chemical Formula 39]

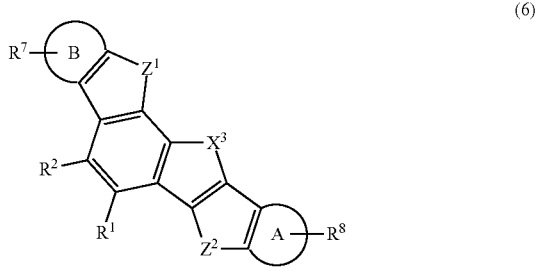

(6)

In the formula (6), $R^1$, $R^2$, $X^3$, $Z^1$, $Z^2$, a ring A and a ring B represent the same meaning as described above. A ring A and a ring B each optionally have a substituent in addition to $R^7$ and $R^8$, and the substituent is the same as the substituent which a ring A and a ring B optionally have explained above.

In the formula (6), $R^7$ and $R^8$ each independently represent a hydrogen atom, an alkyl group, a cycloalkyl group, an alkoxy group, a cycloalkoxy group, an alkylthio group, a cycloalkylthio group, an aryl group, a monovalent heterocyclic group, a halogen atom, a silyl group, an amino group, an alkenyl group, a cycloalkenyl group, an alkynyl group, a hydroxyl group, a nitro group, a cyano group, a carboxyl group, an alkylcarbonyl group, a cycloalkylcarbonyl group, an alkoxycarbonyl group, a cycloalkoxycarbonyl group, a borate residue, a boric acid residue or an organotin residue, and of these groups, an alkyl group, a cycloalkyl group, an alkoxy group, a cycloalkoxy group, an alkylthio group, a cycloalkylthio group, an aryl group, a monovalent heterocyclic group, a silyl group, an amino group, an alkenyl group, a cycloalkenyl group, an alkynyl group, an alkylcarbonyl group, a cycloalkylcarbonyl group, an alkoxycarbonyl group and a cycloalkoxycarbonyl group each optionally have a substituent.

The definition and specific examples of the alkyl group, the cycloalkyl group, the alkoxy group, the cycloalkoxy group, the alkylthio group, the cycloalkylthio group, the aryl group, the monovalent heterocyclic group, the halogen atom, the silyl group, the amino group, the alkenyl group, the cycloalkenyl group, the alkynyl group, the alkylcarbonyl group, the cycloalkylcarbonyl group, the alkoxycarbonyl group and the cycloalkoxycarbonyl group represented by $R^7$ and $R^8$ are the same as the definition and specific examples of the alkyl group, the cycloalkyl group, the alkoxy group, the cycloalkoxy group, the alkylthio group, the cycloalkylthio group, the aryl group, the monovalent heterocyclic group, the halogen atom, the silyl group, the amino group, the alkenyl group, the cycloalkenyl group, the alkynyl group, the alkylcarbonyl group, the cycloalkylcarbonyl group, the alkoxycarbonyl group and the cycloalkoxycarbonyl group as the substituent which the above-described heterocyclic ring optionally has. The definition and specific examples of the borate residue, the boric acid residue or the organotin residue are the same as the definition and specific examples of the borate residue, the boric acid residue or the organotin residue as the above-described polymerization reactive group.

It is preferable that $R^7$ and $R^8$ each independently represent a hydrogen atom, a halogen atom, a silyl group (a silyl group optionally having a substituent), a hydroxyl group, a carboxyl group, a borate residue, a boric acid residue or an organotin residue, from the standpoint of synthesizing the polymer compound of the present invention. The compound of the present invention includes (i) compounds in which $R^7$ and $R^8$ each independently represent a halogen atom, a silyl group optionally having a substituent, a hydroxyl group, a carboxyl group, a borate residue, a boric acid residue or an organotin residue, (ii) compounds in which one of $R^7$ and $R^8$ represents a halogen atom, a silyl group optionally having a substituent, a hydroxyl group, a carboxyl group, a borate residue, a boric acid residue or an organotin residue and the other represents a hydrogen atom and (iii) compounds in which both $R^7$ and $R^8$ represent a hydrogen atom.

The compound represented by the formula (6) is preferably a compound represented by the formula (7), since synthesis of the compound of the present invention is easy.

[Chemical Formula 40]

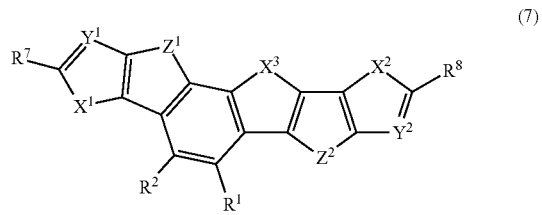

(7)

In the formula (7), $R^1$, $R^2$, $R^7$, $R^3$, $X^1$, $X^2$, $X^3$, $Y^1$, $Y^2$, $Z^1$ and $Z^2$ represent the same meaning as described above.

The compound of the present invention includes compounds represented by the formula (6-1) to the formula (6-20) described below. When the polymer compound of the present invention described above is produced using the compound of the present invention, the compound represented by the formula (6) is preferably a compound represented by the formula (6-1) to the formula (6-10), more preferably a compound represented by the formula (6-1) to the formula (6-8), since an organic transistor produced by using the polymer compound is more excellent in carrier mobility.

[Chemical Formula 41]
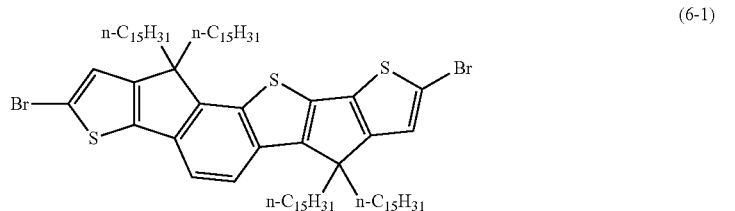
(6-1)
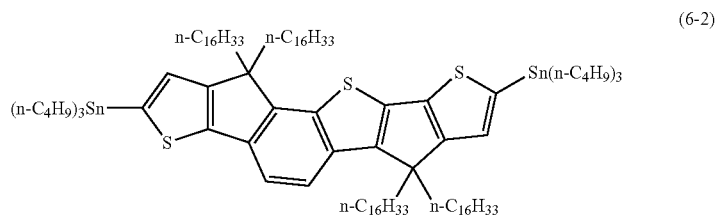
(6-2)
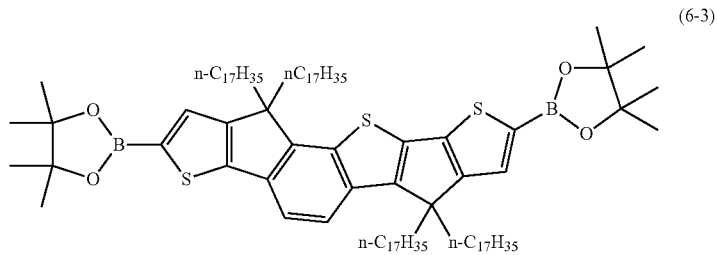
(6-3)
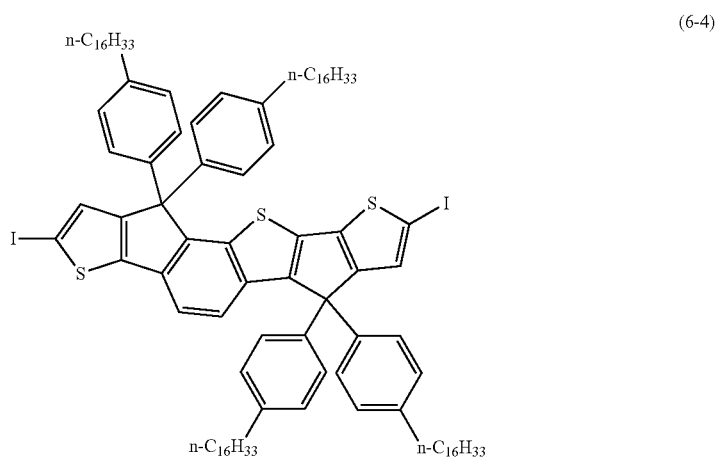
(6-4)
[Chemical Formula 42]
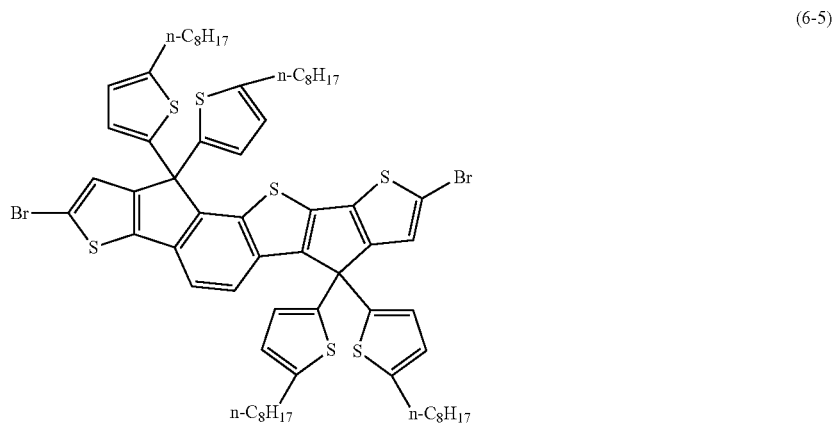
(6-5)

(6-6)
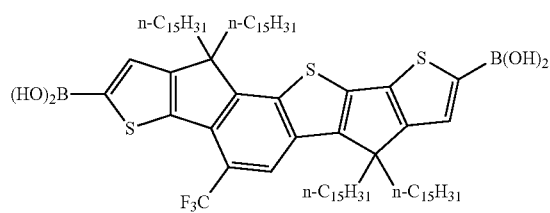
(6-7)
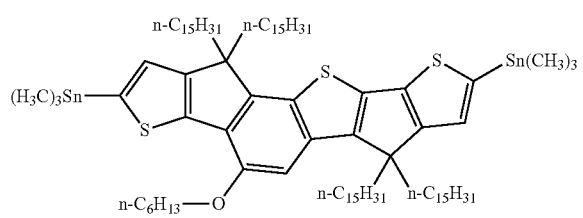
(6-8)
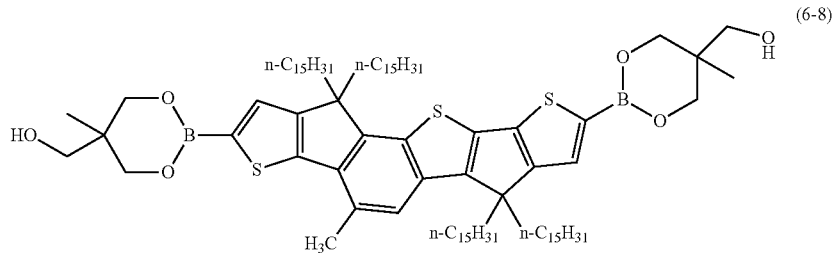
(6-9)
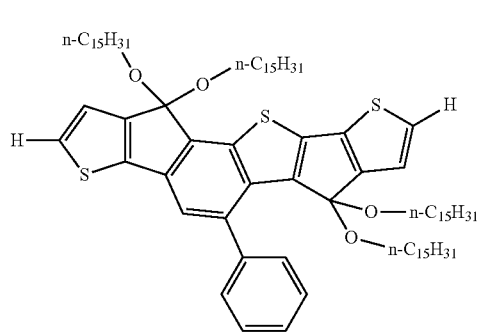
(6-10)
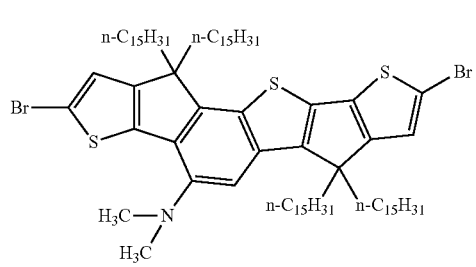
[Chemical Formula 43]
(6-11)
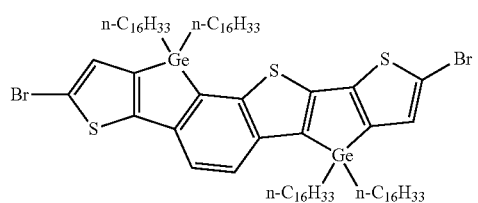

-continued
(6-12)
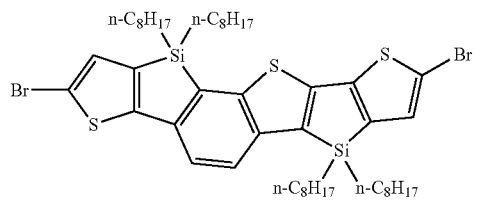
(6-13)
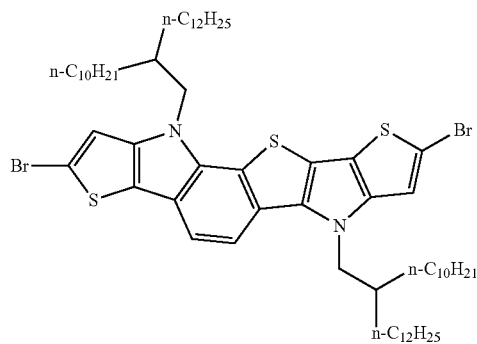
(6-14)
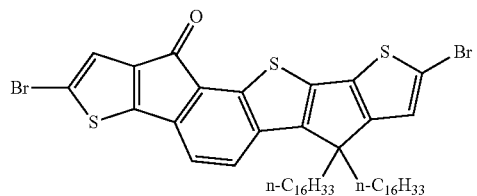
(6-15)
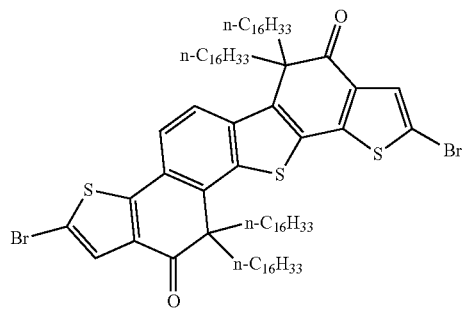
(6-16)
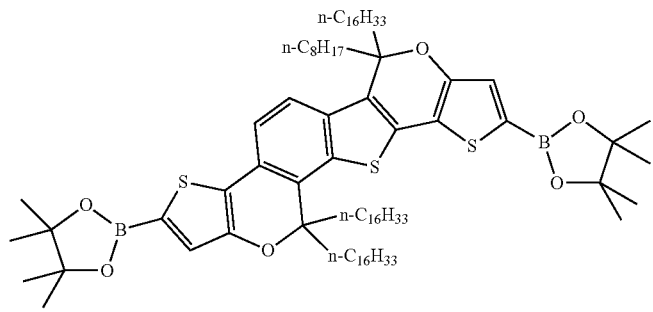
[Chemical Formula 44]
(6-17)
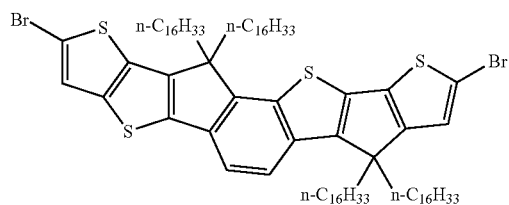

(6-18)
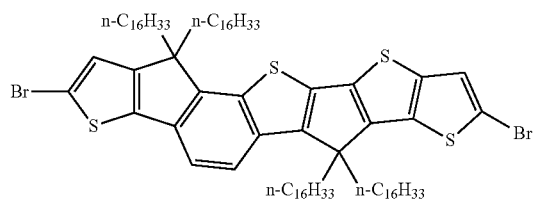

(6-19)
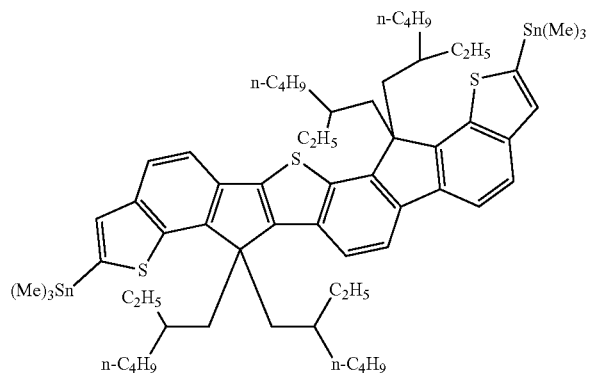

(6-20)
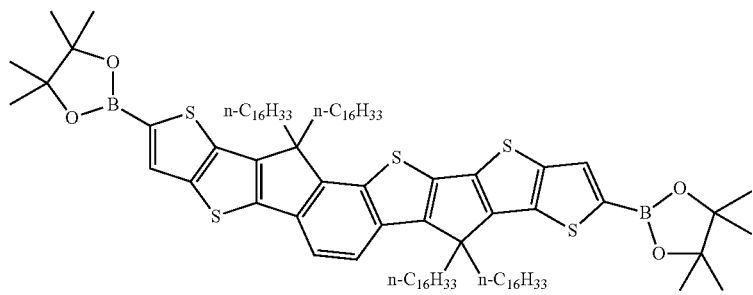

<Production Method of Compound>

Next, a method of producing the compound of the present invention will be explained.

The compound represented by the formula (6) may be produced by any method, and can be produced, for example, by a bromination reaction, the Suzuki coupling reaction, the Wolff-Kishner reduction reaction, the Buchwald-Hartwig amination reaction or an oxidative reduction reaction, as explained below.

When $Z^1$ is a group represented by the formula (Z-5), the compound can be produced, for example, by a first step of reacting a compound represented by the formula (S1), a compound represented by the formula (S2) and a compound represented by the formula (S3) by the Suzuki coupling reaction, and a second step of intramolecularly cyclizing the compound represented by the formula (S4) obtained in the first step.

The compound obtained in this case is a compound represented by the formula (S5). Then, the compound represented by the formula (S5) is (I) reacted with a halogenating agent such as N-bromosuccinimide and the like, (II) subjected to a coupling reaction using a palladium catalyst and the like, or (III) reacted with an alkyllithium to cause lithiation, and further, reacted with tributylbutyltin chloride and the like; thereby a compound represented by the formula (6) can be produced.

[Chemical Formula 45]

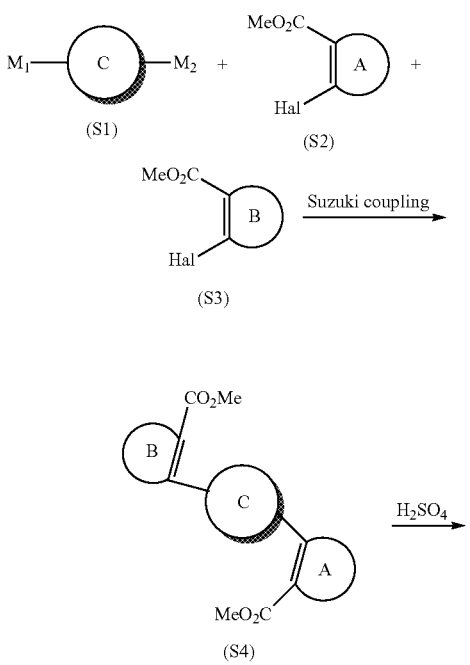

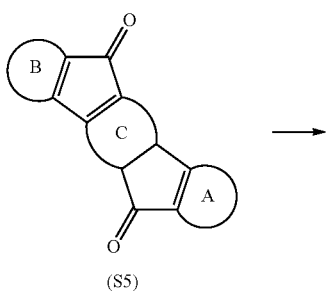

(S5)

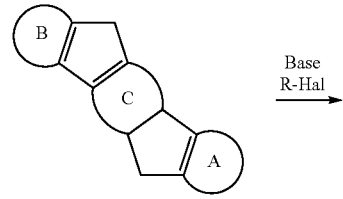

(S6)

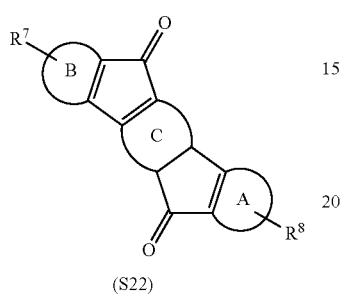

(S22)

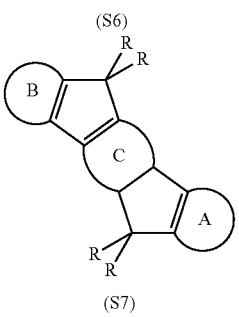

(S7)

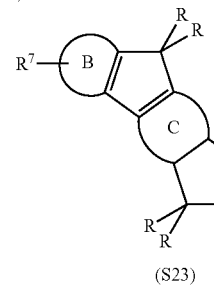

(S23)

In the formulae (S1) to (S5), a ring A, a ring B and a ring C represent the same meaning as described above. $M_1$ and $M_2$ each independently represent a borate residue or a boric acid residue (a group represented by —$B(OH)_2$). Hal represents an iodine atom, a bromine atom or a chlorine atom. Hal in the formula (S2) and Hal in the formula (S3) may be the same or different.

When $Z^1$ is a group represented by the formula (Z-1), the compound can be produced, for example, by a first step of reacting the above-described compound represented by the formula (S5) by the Wolff-Kishner reduction reaction, and a second step of reacting the compound represented by the formula (S6) obtained in the first step, a base such as a sodium alkoxide and the like and an alkyl halide.

The compound obtained in this case is a compound represented by the formula (S7). Then, the compound represented by the formula (S7) is (I) reacted with a halogenating agent such as N-bromosuccinimide and the like, (II) subjected to a coupling reaction using a palladium catalyst and the like, or (III) reacted with an alkyllithium to cause lithiation, and further, reacted with tributylbutyltin chloride and the like; thereby a compound represented by the formula (6) can be produced.

[Chemical Formula 46]

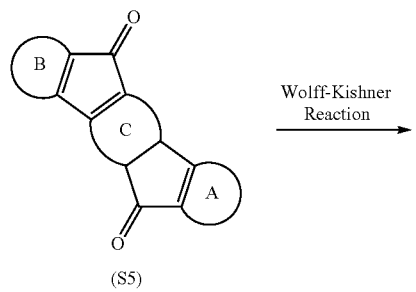

Wolff-Kishner Reaction (S5)

In the formulae (S5) to (S7), R, a ring A, a ring B, a ring C and Hal represent the same meaning as described above.

When $Z^1$ and $Z^2$ represent a group represented by the formula (Z-1), the compound can be produced, alternatively, by a first step of reacting a compound represented by the formula (S1), a compound represented by the formula (S8) and a compound represented by the formula (S9) by the Suzuki coupling reaction, a second step of reacting the compound represented by the formula (S10) obtained in the first step and butyllithium to cause lithiation, and further, reacting with a ketone, and a third step of reacting the compound represented by the formula (S11) obtained in the second step and an acid such as trifluoroboric acid, sulfuric acid and the like to cause cyclization.

The compound obtained in this case is a compound represented by the formula (S7). Then, the compound represented by the formula (S7) is (I) reacted with a halogenating agent such as N-bromosuccinimide and the like, (II) subjected to a coupling reaction using a palladium catalyst and the like, or (III) reacted with an alkyllithium to cause lithiation, and further, reacted with tributylbutyltin chloride and the like; thereby a compound represented by the formula (6) can be produced.

[Chemical Formula 47]

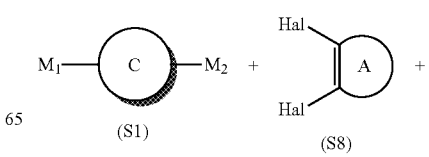

(S1)           (S8)

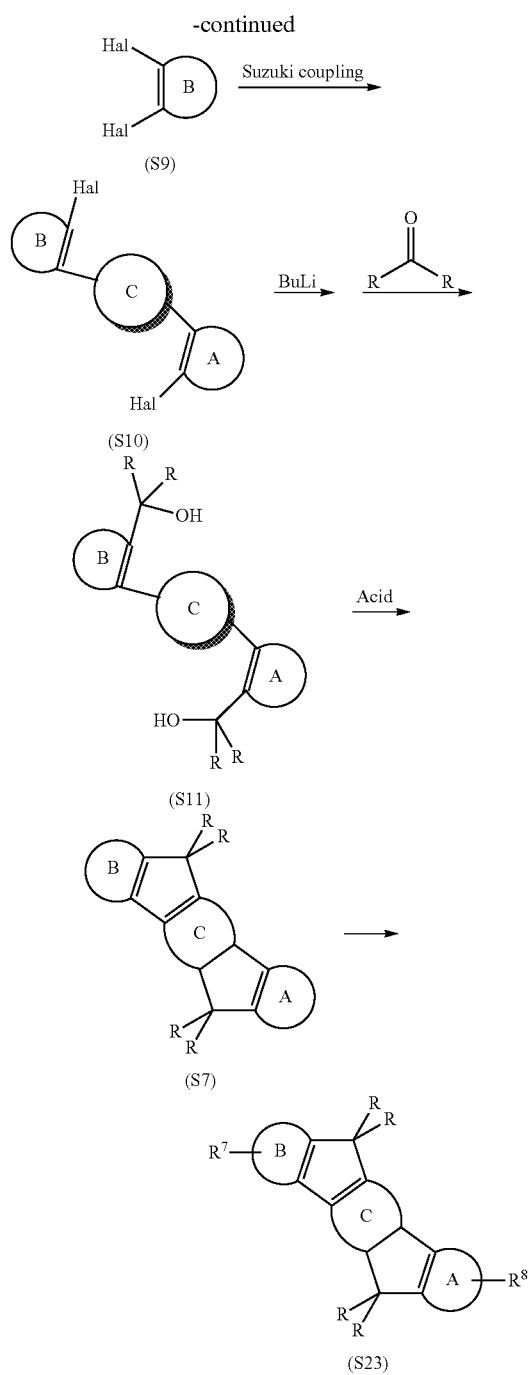

(S9)
(S10)
(S11)
(S7)
(S23)

a second step of reacting the compound represented by the formula (S12) obtained in the first step and butyllithium to cause lithiation, and further, reacting with a compound represented by the formula: $R_2ECl_2$, and the like.

The compound obtained in this case is a compound represented by the formula (S13). Then, the compound represented by the formula (S13) is (I) reacted with a halogenating agent such as N-bromosuccinimide and the like, (II) subjected to a coupling reaction using a palladium catalyst and the like, or (III) reacted with an alkyllithium to cause lithiation, and further, reacted with tributylbutyltin chloride and the like; thereby a compound represented by the formula (6) can be produced.

[Chemical Formula 48]

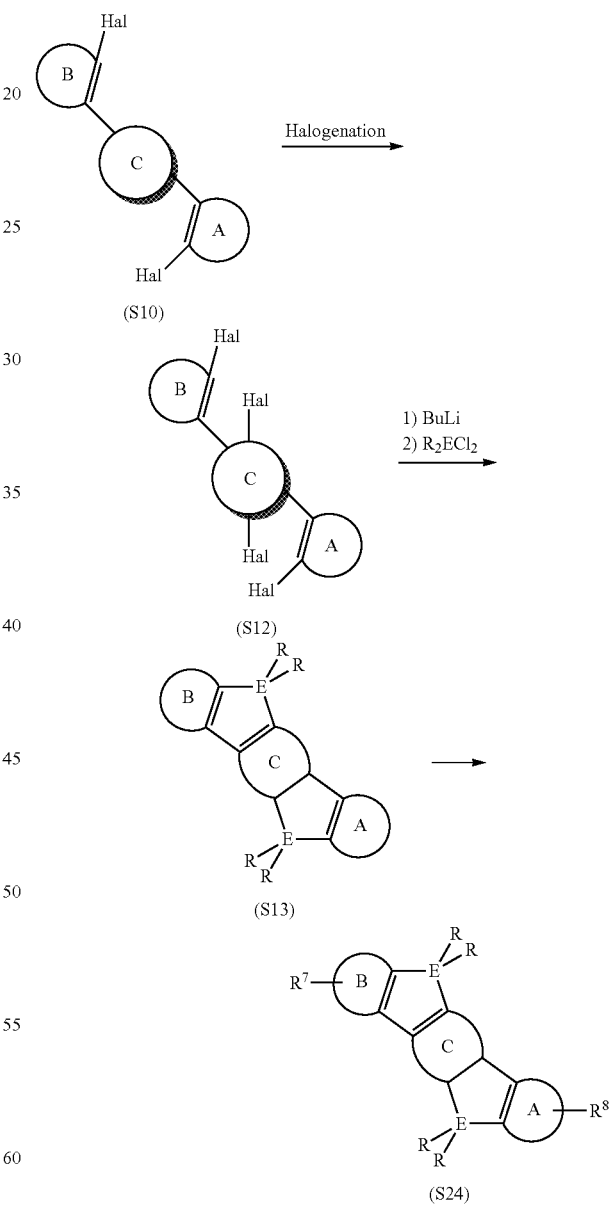

(S10)
(S12)
(S13)
(S24)

In the formulae (S1) and (S7) to (S11), R, $M_1$, $M_2$, a ring A, a ring B, a ring C and Hal represent the same meaning as described above. A plurality of Hal present in the formula (S8) may be the same or different, a plurality of Hal present in the formula (S9) may be the same or different, and Hal in the formula (S8) and Hal in the formula (S9) may be the same or different.

When $Z^1$ is a group represented by the formula (Z-2) or the formula (Z-3), the compound can be produced, for example, by a first step of reacting the above-described compound represented by the formula (S10) and a halogenating agent such as N-bromosuccinimide and the like, and In the formulae (S10), (S12) and (S13), R, a ring A, a ring B, a ring C and Hal represent the same meaning as described above. E represents a silicon atom or a germanium atom. A plurality of Hal present in the formula (S10) may be the same or different, and a plurality of Hal present in the formula (S12) may be the same or different.

When $Z^1$ is a group represented by the formula (Z-4), the compound can be produced, for example, by reacting the above-described compound represented by the formula (S12) and a compound represented by the formula (S14) by the Buchwald-Hartwig amination reaction.

The compound obtained in this case is a compound represented by the formula (S15). Then, the compound represented by the formula (S15) is (I) reacted with a halogenating agent such as N-bromosuccinimide and the like, (II) subjected to a coupling reaction using a palladium catalyst and the like, or (III) reacted with an alkyllithium to cause lithiation, and further, reacted with tributylbutyltin chloride and the like; thereby a compound represented by the formula (6) can be produced.

[Chemical Formula 49]

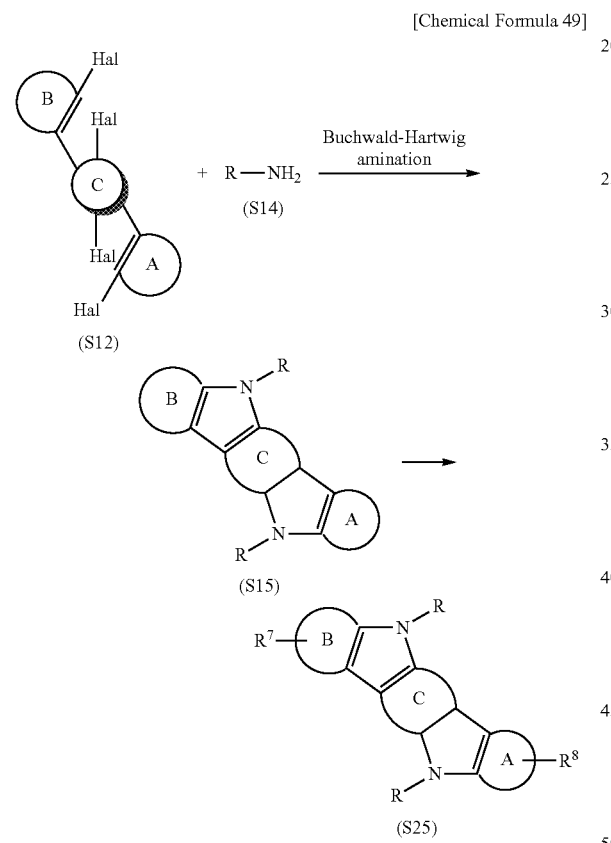

In the formulae (512), (S14) and (S15), R, a ring A, a ring B, a ring C and Hal represent the same meaning as described above. A plurality of Hal present in the formula (S12) may be the same or different.

When $Z^1$ is a group represented by the formula (Z-1), the compound can be produced, alternatively, by a first step of reacting a compound represented by the formula (S16), a compound represented by the formula (S19) and a compound represented by the formula (S20) by the Suzuki coupling reaction, and a second step of intramolecularly cyclizing the compound represented by the formula (S21) obtained in the first step.

The compound obtained in this case is a compound represented by the formula (S7). Then, the compound represented by the formula (S7) is (I) reacted with a halogenating agent such as N-bromosuccinimide and the like, (II) subjected to a coupling reaction using a palladium catalyst and the like, or (III) reacted with an alkyllithium to cause lithiation, and further, reacted with tributylbutyltin chloride and the like; thereby a compound represented by the formula (6) can be produced.

[Chemical Formula 50]

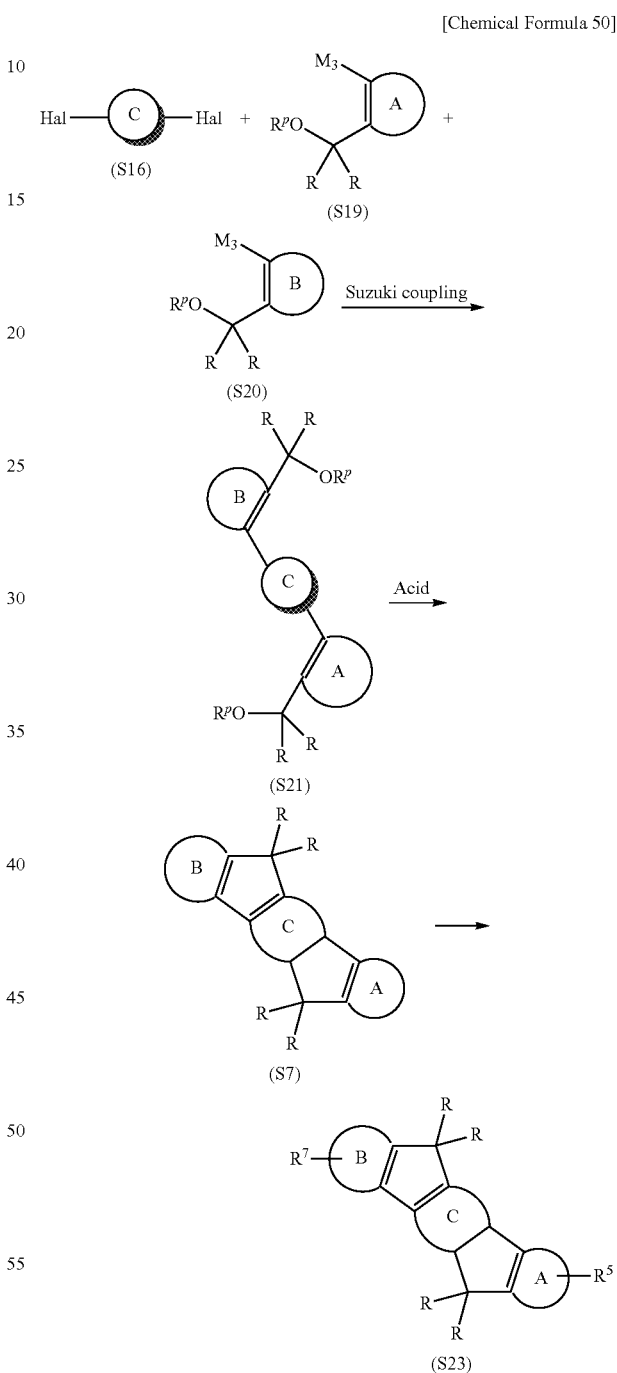

In the formulae (S7), (S16), (S19), (S20) and (S21), R, a ring A, a ring B, a ring C and Hal represent the same meaning as described above. $M_3$ and $M_4$ each independently represent a borate residue or a boric acid residue (a group represented by —B(OH)$_2$). $R^p$ represents an alkyl group, a silyl group or an acetyl group. A plurality of Hal present in the formula (S24) may be the same or different. $R^p$ in the formula (S19) and $R^p$ in the formula (S20) may be the same or different.

<Organic Semiconductor Composition>

The organic semiconductor composition of the present invention may be one containing the polymer compound of the present invention singly or one containing two or more kinds of the polymer compounds of the present invention in combination. The organic semiconductor composition of this embodiment may further contain a compound having carrier transportability or a polymer compound, in addition to the polymer compound of the present invention. When the organic semiconductor composition of this embodiment contains a component other than the polymer compound of the present invention, the polymer compound of the present invention is contained in an amount of preferably 30 wt % or more, more preferably 50 wt % or more, further preferably 70 wt % or more. The organic semiconductor composition of the present invention can be suitably used as an organic semiconductor layer of an organic semiconductor device.

The compound having carrier transportability includes low molecular weight compounds such as arylamine derivatives, stilbene derivatives, oligothiophene and derivatives thereof, oxadiazole derivatives, fullerenes and derivatives thereof, and the like; and, polyvinylcarbazole and derivatives thereof, polyaniline and derivatives thereof, polythiophene and derivatives thereof, polypyrrole and derivatives thereof, polyphenylenevinylene and derivatives thereof, polythienylenevinylene and derivatives thereof, polyfluorene and derivatives thereof, and the like.

The organic semiconductor composition may contain a polymer compound other than the polymer compound of the present invention as a polymer binder for improving its property. The polymer binder is preferably one which does not excessively lower carrier transportability.

Examples of the polymer binder include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride and polysiloxane.

<Organic Semiconductor Device>

The organic semiconductor device of the present invention is an organic semiconductor device having a first electrode, a second electrode and an organic semiconductor layer wherein the organic semiconductor layer contains the polymer compound of the present invention. The organic semiconductor device of the present invention may further contain an electrode in addition to the first electrode and the second electrode. One embodiment of the organic semiconductor device of the present invention is an organic semiconductor device having a first electrode and a second electrode and having an organic semiconductor layer between the first electrode and the second electrode wherein the organic semiconductor layer contains the polymer compound of the present invention. When an organic semiconductor layer containing the polymer compound of the present invention is used in an organic semiconductor device, the polymer compound of the present invention can transport electrons and holes injected from an electrode or charges generated by light absorption, since the polymer compound of the present invention has high carrier mobility. The polymer compound of the present invention can be suitably used in various organic semiconductor devices such as a photoelectric conversion device, an organic transistor, an organic electroluminescent device, an organic field effect type transistor (OFET) sensor, an organic conductivity modulation type sensor and the like by utilizing such characteristics. These devices will be individually explained below.

(Photoelectric Conversion Device)

A photoelectric conversion device containing the polymer compound of the present invention has one or more active layers containing the polymer compound of the present invention between a pair of electrodes at least one of which is transparent or semi-transparent.

A preferable form of a photoelectric conversion device containing the polymer compound of the present invention has a pair of electrodes at least one of which is transparent or semi-transparent, and an active layer formed from a composition of a p-type organic semiconductor and an n-type organic semiconductor. The polymer compound of the present invention is preferably used as a p-type organic semiconductor. The action mechanism of this form of photoelectric conversion device is explained. Incident light energy from a transparent or semi-transparent electrode is absorbed in an electron accepting compound (n-type organic semiconductor) such as a fullerene derivative and the like and/or an electron donating compound (p-type organic semiconductor) such as the compound of the present invention and the like, thereby generating an exciton composed of an electron and a hole bound mutually. When the generated exciton moves and reaches the heterojunction interface at which an electron accepting compound and an electron donating compound are adjacent, an electron and a hole separate due to a difference of respective HOMO energies and LUMO energies at the interface, to generate independently movable charges (electron and hole). The generated charges move to respective electrodes and can be taken out to the outside as an electric energy (electric current).

A photoelectric conversion device produced by using the polymer compound of the present invention is usually formed on a substrate. This substrate is advantageously one which does not chemically change in forming an electrode and forming a layer of an organic substance. The material of the substrate includes, for example, glass, plastic, polymer film and silicon. In the case of an opaque substrate, it is preferable that the opposite electrode (namely, an electrode far from the substrate) is transparent or semi-transparent.

Another form of a photoelectric conversion device having the polymer compound of the present invention is a photoelectric conversion device having a first active layer containing the polymer compound of the present invention and a second active layer containing an electron accepting compound such as a fullerene derivative and the like adjacent to the first active layer, between a pair of electrodes at least one of which is transparent or semi-transparent.

The above-described transparent or semi-transparent electrode material includes electrically conductive metal oxide films, semi-transparent metal films and the like. Specifically, use is made of films fabricated by using an electrically conductive material composed of indium oxide, zinc oxide, tin oxide, and composites thereof: indium•tin•oxide (hereinafter, referred to as "ITO" in some cases), indium•zinc•oxide and the like, NESA and, gold, platinum, silver, copper and the like, and preferable are ITO, indium•zinc•oxide and tin oxide. The electrode fabrication method includes a vacuum vapor deposition method, a sputtering method, an ion plating method, a plating method and the like. As the electrode material, an organic transparent conductive film composed of polyaniline and derivatives thereof, polythiophene and derivatives thereof and the like may be used.

One electrode may not be transparent, and metals, conductive polymers and the like can be used as the electrode material of the electrode. Specific examples of the electrode material include metals such as lithium, sodium, potassium, rubidium, cesium, magnesium, calcium, strontium, barium, aluminum, scandium, vanadium, zinc, yttrium, indium, cerium, samarium, europium, terbium, ytterbium and the like, and alloys composed of two or more of them, or alloys composed of one or more of the above-described metals and one or more metals selected from the group consisting of gold, silver, platinum, copper, manganese, titanium, cobalt, nickel, tungsten and tin, graphite, graphite intercalation compounds, polyaniline and derivatives thereof and polythiophene and derivatives thereof. The alloy includes a magnesium-silver alloy, a magnesium-indium alloy, a magnesium-aluminum alloy, an indium-silver alloy, a lithium-aluminum alloy, a lithium-magnesium alloy, a lithium-indium alloy, a calcium-aluminum alloy and the like.

As a means for improving photoelectric conversion efficiency, an additional intermediate layer other than the active layer may be used. The material used as the intermediate layer includes halides of alkali metals and alkaline earth metals such as lithium fluoride and the like, oxides such as titanium oxide and the like, PEDOT (poly-3,4-ethylenedioxythiophene) and the like.

The active layer may contain the polymer compound of the present invention singly or two or more of the polymer compounds of the present invention in combination. A compound other than the polymer compound of the present invention can also be mixed and used as an electron donating compound and/or an electron accepting compound in the active layer. The electron donating compound and the electron accepting compound are determined relatively based on the energy levels of these compounds.

The above-described electron donating compound includes, for example, pyrazoline derivatives, arylamine derivatives, stilbene derivatives, triphenyldiamine derivatives, oligothiophene and derivatives thereof, polyvinylcarbazole and derivatives thereof, polysilane and derivatives thereof, polysiloxane derivatives having an aromatic amine residue in the side chain or the main chain, polyaniline and derivatives thereof, polythiophene and derivatives thereof, polypyrrole and derivatives thereof, polyphenylenevinylene and derivatives thereof and polythienylenevinylene and derivatives thereof, in addition to the polymer compound of the present invention.

The above-described electron accepting compound includes, for example, carbon materials, metal oxides such as titanium oxide and the like, oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, polyquinoline and derivatives thereof, polyquinoxaline and derivatives thereof, polyfluorene and derivatives thereof, phenanthrene derivatives such as 2,9-dimethyl-4,7-diphenyl-1,10-phenanthroline (Bathocuproine) and the like, fullerenes and fullerene derivatives, in addition to the polymer compound of the present invention, and titanium oxide, carbon nanotubes, fullerenes and fullerene derivatives are preferable, fullerenes and fullerene derivatives are particularly preferable.

The fullerenes and fullerene derivatives include $C_{60}$, $C_{70}$, $C_{76}$, $C_{78}$, $C_{84}$ and derivatives thereof. The specific structure of the fullerene derivative includes those as shown below.

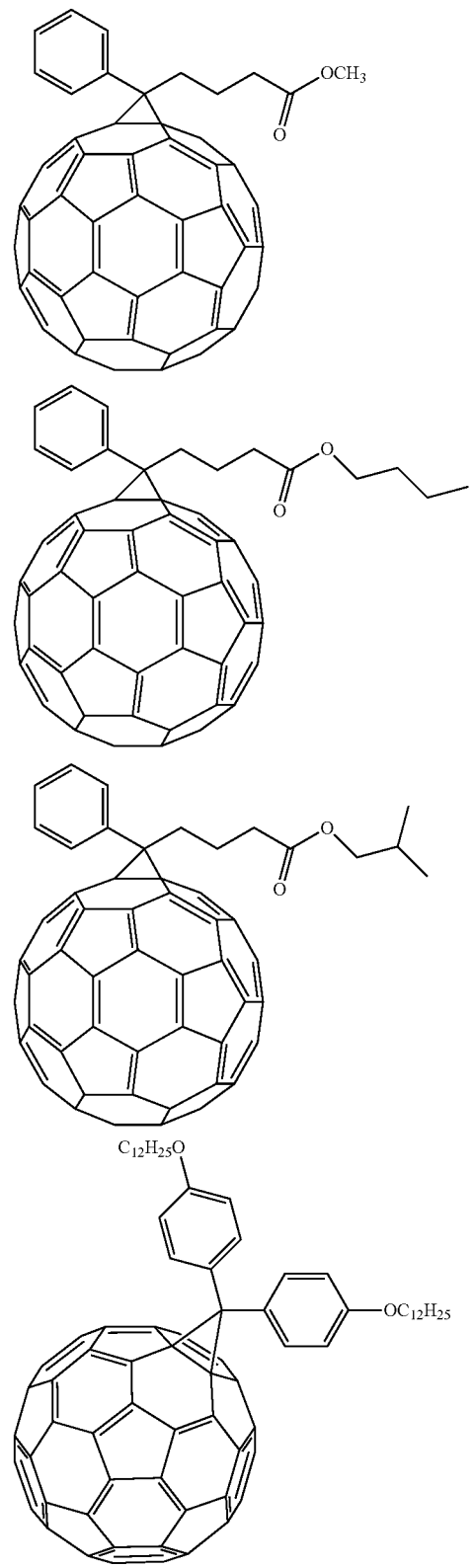

-continued

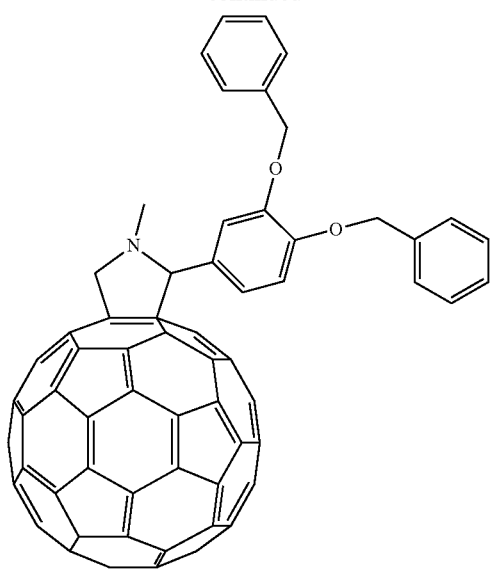

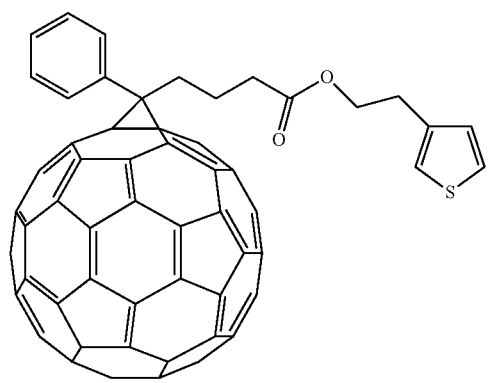

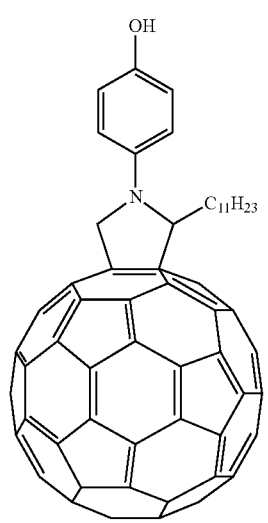

-continued

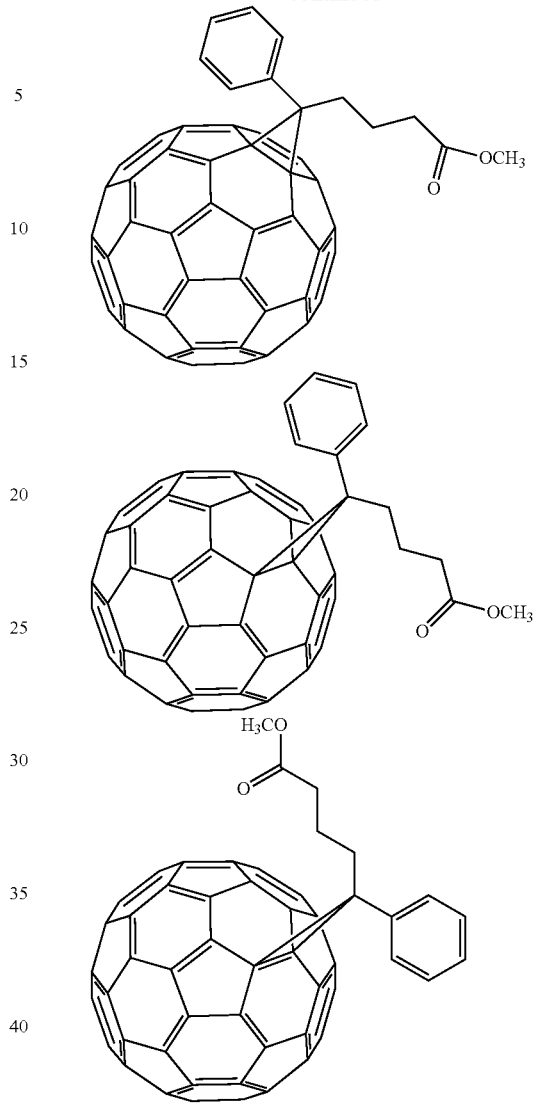

Examples of the fullerene derivative include [6,6]phenyl-C61 butyric acid methyl ester (C60PCBM, [6,6]-Phenyl C61 butyric acid methyl ester), [6,6]phenyl-C70 butyric acid methyl ester (C70PCBM, [6,6]-Phenyl C70 butyric acid methyl ester), [6,6]phenyl-C84 butyric acid methyl ester (C84PCBM, [6,6]-Phenyl C84 butyric acid methyl ester), [6,6]thienyl-C60 butyric acid methyl ester ([6,6]-Thienyl C60 butyric acid methyl ester) and the like.

When the polymer compound of the present invention and a fullerene derivative are contained in the active layer, the proportion of the fullerene derivative is preferably 10 to 1000 parts by weight, more preferably 20 to 500 parts by weight with respect to 100 parts by weight the polymer compound of the present invention.

The thickness of the active layer is usually preferably 1 nm to 100 μm, more preferably 2 nm to 1000 nm, further preferably 5 nm to 500 nm, still more preferably 20 nm to 200 nm.

The active layer may be produced by any method and the production method includes, for example, film formation from a solution containing the polymer compound of the present invention and film formation by a vacuum vapor deposition method.

A preferable method of producing a photoelectric conversion device is a production method of a photoelectric conversion device having a first electrode and a second electrode and having an active layer between the first electrode and the second electrode, comprising a step of applying a solution (ink) containing the polymer compound of the present invention and a solvent by an application method on the first electrode to form an active layer and a step of forming a second electrode on the active layer.

The solvent used for film formation from a solution is advantageously one which dissolves the polymer compound of the present invention. The solvent includes, for example, unsaturated hydrocarbon solvents such as toluene, xylene, mesitylene, tetralin, decalin, bicyclohexyl, n-butylbenzene, sec-butylbenzene, tert-butylbenzene and the like, halogenated saturated hydrocarbon solvents such as carbon tetrachloride, chloroform, dichloromethane, dichloroethane, chlorobutane, bromobutane, chloropentane, bromopentane, chlorohexane, bromohexane, chlorocyclohexane, bromocyclohexane and the like, halogenated unsaturated hydrocarbon solvents such as chlorobenzene, dichlorobenzene, trichlorobenzene and the like, and ether solvents such as tetrahydrofuran, tetrahydropyran and the like. The polymer compound of the present invention can be dissolved usually in an amount of 0.1 wt % or more in the above-described solvent.

In the case of film formation using a solvent, application methods such as a slit coat method, a knife coat method, a spin coat method, a casting method, a micro gravure coat method, a gravure coat method, a bar coat method, a roll coat method, a wire bar coat method, a dip coat method, a spray coat method, a screen printing method, a gravure printing method, a flexo printing method, an offset printing method, an inkjet printing method, a dispenser printing method, a nozzle coat method, a capillary coat method and the like can be used, and preferable are a slit coat method, a capillary coat method, a gravure coat method, a micro gravure coat method, a bar coat method, a knife coat method, a nozzle coat method, an inkjet printing method and a spin coat method.

From the standpoint of film formability, the surface tension of a solvent at 25° C. is preferably larger than 15 mN/m, more preferably larger than 15 mN/m and smaller than 100 mN/m, further preferably larger than 25 mN/m and smaller than 60 mN/m.

(Organic Film Solar Battery)

In a photoelectric conversion device using the polymer compound of the present invention, when light such as solar light and the like is applied from a transparent or semi-transparent electrode, photovoltaic power is generated between electrodes, thus, the photoelectric conversion device can be operated as an organic film solar battery. By integrating a plurality of organic film solar batteries, they can also be used as an organic film solar battery module.

By applying light from a transparent or semi-transparent electrode under condition of application of voltage between electrodes or no application of voltage, photocurrent flows, thus the photoelectric conversion device can be operated as an organic optical sensor. By integrating a plurality of organic optical sensors, they can also be used as an organic image sensor.

The organic film solar battery can take basically the same module structure as that of a conventional solar battery module. A solar battery module generally takes a structure in which a cell is constituted on a supporting substrate made of a metal, ceramic or the like, its upper side is covered with a filling resin, protective glass or the like and light is incorporated from the opposite side of the supporting substrate, however, it is also possible to provide a structure in which a transparent material such as reinforced glass and the like is used as a supporting substrate, a cell is constituted on this and light is incorporated from the side of the transparent supporting substrate. Specifically, module structures called super straight type, sub straight type or potting type, substrate integrated module structures used in amorphous silicon solar batteries, and the like, are known. Also an organic film solar battery produced by using the polymer compound of the present invention can appropriately adopt these module structures depending on the use object, the use place and environments.

A typical super straight type or sub straight type module has a structure in which cells are placed at regular intervals between supporting substrates one or both of which are transparent and having undergone an antireflection treatment, mutually adjacent cells are connected via a metal lead, flexible wiring or the like, a collecting electrode is placed at the exterior edge, and generated electric power is taken out to the outside. Between a substrate and a cell, various kinds of plastic materials such as ethylene vinyl acetate (EVA) and the like depending on the object may be used in the form of a film or a filling resin, for protection of the cell and improvement of power collecting efficiency. In the case of use at a place where the surface is not required to be covered with a hard material such as a place receiving little impact from the outside, it is possible that the surface protective layer is constituted of a transparent plastic film or the above-described filling resin is hardened to impart a protective function, and a supporting substrate on one side is deleted. The circumference of the supporting substrate is fixed in the form of sandwich by a metal frame and the aperture between the supporting substrate and the frame is sealed with a sealing material, for ensuring internal sealing and module stiffness. When a flexible material is used as a cell itself or a supporting substrate, a filling material and a sealing material, it is also possible to constitute a solar battery on a curved surface.

In the case of a solar battery using a flexible supporting body such as a polymer film and the like, it is possible that cells are formed in series while feeding a supporting body in the form of a roll, cut into desired size, then, the periphery is sealed with a flexible and moisture-proof material, thus, a battery body is fabricated. Also, a module structure called "SCAF" described in Solar Energy Materials and Solar Cells, 48, pp. 383-391 can be adopted. Further, a solar battery using a flexible supporting body can also be adhered and fixed to curved glass or the like and used.

(Organic Electroluminescent Device)

The polymer compound of the present invention can also be used in an organic electroluminescent device (hereinafter, referred to as "organic EL device" in some cases). The organic EL device has a light emitting layer between a pair of electrodes at least one of which is transparent or semi-transparent. The organic EL device may contain a hole transporting layer and an electron transporting layer in addition to the light emitting layer. The polymer compound of the present invention is contained in any of the light emitting layer, the hole transporting layer and the electron transporting layer. Charge transporting materials (denoting a generic term of an electron transporting material and a hole transporting material) may be contained, in addition to the polymer compound of the present invention, in the light emitting layer. The organic EL device includes a device having an anode, a light emitting layer and a cathode, a device having an anode, a light emitting layer, an electron transporting layer and a cathode and further having an electron transporting layer containing an electron transporting material between the cathode and the light emitting layer and adjacent to the light emitting layer, a device having an anode, a hole transporting layer, a light emitting layer and a cathode and further having a hole transporting layer containing a hole transporting material between the anode and the light emitting layer and adjacent to the light emitting layer, a device having an anode, a hole transporting layer, a light emitting layer, an electron transporting layer and a cathode, and the like.

(Organic Transistor)

The organic transistor includes those having a constitution having a source electrode and a drain electrode, an active layer working as a current pathway between these electrodes and containing the polymer compound of the present invention, and a gate electrode controlling the amount of current passing through the current pathway. The organic transistor having such a constitution includes an organic field effect type transistor, an organic electrostatic induction type transistor and the like.

The organic field effect type transistor is usually an organic transistor having a source electrode and a drain electrode, an active layer working as a current pathway between these electrodes and containing the polymer compound of the present invention, a gate electrode controlling the amount of current passing through the current pathway, and an insulating layer disposed between the active layer and the gate electrode. Particularly, preferable is an organic transistor in which a source electrode and a drain electrode are provided in contact with an active layer and further, a gate electrode is provided sandwiching an insulating layer in contact with an active layer.

The organic electrostatic induction type transistor is usually an organic transistor having a source electrode and a drain electrode, an active layer working as a current pathway between these electrodes and containing the polymer compound of the present invention, and a gate electrode controlling the amount of current passing through the current pathway wherein the gate electrode is provided in the active layer. Particularly, preferable is an organic transistor in which a source electrode, a drain electrode and the above-described gate electrode are provided in contact with the above-described active layer.

The gate electrode advantageously has a structure by which a current pathway flowing from a source electrode to a drain electrode can be formed and the amount of current passing through the current pathway can be controlled by the voltage applied to the gate electrode, and is, for example, a comb-shaped electrode.

FIG. 1 is a schematic cross-sectional view showing an example of the TGBC device structure of the organic transistor of the present invention (organic field effect type transistor). An organic transistor 100 shown in FIG. 1 has a substrate 1, a source electrode 5 and a drain electrode 6 formed at a prescribed interval on the substrate 1, an active layer 2 formed on the substrate 1 so as to cover the source electrode 5 and the drain electrode 6, an insulating layer 3 formed on the active layer 2, and a gate electrode 4 formed on the insulating layer 3 so as to cover the insulating layer 3 on a region between the source electrode 5 and the drain electrode 6.

FIG. 2 is a schematic cross-sectional view showing another example of the organic transistor of the present invention (organic field effect type transistor). An organic transistor 110 shown in FIG. 2 has a substrate 1, a source electrode 5 formed on the substrate 1, an active layer 2 formed on the substrate 1 so as to cover the source electrode 5, a drain electrode 6 formed at a prescribed interval from the source electrode 5 on the active layer 2, an insulating layer 3 formed on the active layer 2 and the drain electrode 6, and a gate electrode 4 formed on the insulating layer 3 so as to cover the insulating layer 3 on a region between the source electrode 5 and the drain electrode 6.

FIG. 3 is a schematic cross-sectional view showing an example of the BGBC device structure of the organic transistor of the present invention (organic field effect type transistor). An organic transistor 120 shown in FIG. 3 has a substrate 1, a gate electrode 4 formed on the substrate 1, an insulating layer 3 formed on the substrate 1 so as to cover the gate electrode 4, a source electrode 5 and a drain electrode 6 formed at a prescribed interval on the insulating layer 3 so as to cover parts of a region of the insulating layer 3 where the gate electrode 4 is formed below, and an active layer 2 formed on the insulating layer 3 so as to cover parts of the source electrode 5 and the drain electrode 6.

FIG. 4 is a schematic cross-sectional view showing another example of the organic transistor of the present invention (organic field effect type transistor). An organic transistor 130 shown in FIG. 4 has a substrate 1, a gate electrode 4 formed on the substrate 1, an insulating layer 3 formed on the substrate 1 so as to cover the gate electrode 4, a source electrode 5 formed on the insulating layer 3 so as to cover a part of a region of the insulating layer 3 where the gate electrode 4 is formed below, an active layer 2 formed on the insulating layer 3 so as to cover a part of the source electrode 5, and a drain electrode 6 formed at a prescribed interval from the source electrode 5 on the insulating layer 3 so as to cover a part of the active layer 2.

FIG. 5 is a schematic cross-sectional view showing another example of the organic transistor of the present invention (organic electrostatic induction type transistor) An organic transistor 140 shown in FIG. 5 has a substrate 1, a source electrode 5 formed on the substrate 1, an active layer 2 formed on the source electrode 5, a plurality of gate electrodes 4 formed at prescribed intervals on the active layer 2, an active layer 2a formed on the active layer 2 so as to cover all the gate electrodes 4 (the material constituting the active layer 2a may be the same as or different from the material of the active layer 2), and a drain electrode 6 formed on the active layer 2a.

FIG. 6 is a schematic cross-sectional view showing another example of the organic transistor of the present invention (organic field effect type transistor). An organic transistor 150 shown in FIG. 6 has a substrate 1, an active layer 2 formed on the substrate 1, a source electrode 5 and a drain electrode 6 formed at a prescribed interval on the active layer 2, an insulating layer 3 formed on the active layer 2 so as to cover parts of the source electrode 5 and the drain electrode 6, and a gate electrode 4 formed on the insulating layer 3 so as to cover respective parts of a region of the insulating layer 3 where the source electrode 5 is formed below and a region of the insulating layer 3 wherein the drain electrode 6 is formed below.

FIG. 7 is a schematic cross-sectional view showing another example of the organic transistor of the present invention (organic field effect type transistor). An organic transistor 160 shown in FIG. 7 has a substrate 1, a gate electrode 4 formed on the substrate 1, an insulating layer 3 formed on the substrate 1 so as to cover the gate electrode 4, an active layer 2 formed so as to cover a region of the insulating layer 3 where the gate electrode 4 is formed below, a source electrode 5 formed on the active layer 2 so as to cover a part of the active layer 2, and a drain electrode 6 formed at a prescribed interval from the source electrode 5 on the active layer 2 so as to cover a part of the active layer 2.

FIG. 8 is a schematic cross-sectional view showing another example of the organic transistor of the present invention (organic field effect type transistor). An organic transistor 170 shown in FIG. 8 has a gate electrode 4, an insulating layer 3 formed on the gate electrode 4, an active layer 2 formed on the insulating layer 3, and a source electrode 5 and a drain electrode 6 formed at a prescribed interval on the active layer 2. In this constitution, the gate electrode 4 works also as a substrate 1.

FIG. 9 is a schematic cross-sectional view showing another example of the BGBC device structure of the organic transistor of the present invention (organic field effect type transistor). An organic transistor 180 shown in FIG. 9 has a gate electrode 4, an insulating layer 3 formed on the gate electrode 4, a source electrode 5 and a drain electrode 6 formed at a prescribed interval on the insulating layer 3, and an active layer 2 formed on the insulating layer 3 so as to cover parts of the source electrode 5 and the drain electrode 6.

In the organic transistor of the present invention described above, the active layer 2 and/or the active layer 2a is constituted of a film containing the polymer compound of the present invention, and provides a current pathway (channel) between the source electrode 5 and the drain electrode. The gate electrode 4 controls the amount of current passing through the current pathway (channel) by applying voltage.

Such an organic field effect type transistor can be produced by known methods, for example, a method described in JP-A No. Hei 5-110069. The electrostatic induction type organic transistor can be produced by known methods such as a method described in JP-A No. 2004-006476 and the like.

The material of the substrate 1 is advantageously a material which does not disturb the characteristic of an organic transistor. As the substrate, a glass substrate, a flexible film substrate and a plastic substrate can be used.

The material of the insulating layer 3 is advantageously a material having a high electrical insulating property, and $SiO_x$, $SiN_x$, $Ta_2O_5$, polyimide, polyvinyl alcohol, polyvinylphenol, organic glass, photoresist and the like can be used, and from the standpoint of lowering of voltage, it is preferable to use a material having high permittivity.

When the active layer 2 is formed on the insulating layer 3, it is also possible to form the active layer 2 after surface-modifying the insulating layer 3 by treating the surface of the insulating layer 3 with a surface treatment agent such as a silane coupling agent and the like, for improving the interfacial characteristic of the insulating layer 3 and the active layer 2.

In the case of a field effect type transistor, charges such as an electron and a hole generally pass around the interface of an insulating layer and an active layer. Therefore, the condition of this interface exerts a great influence on the carrier mobility of a transistor. Accordingly, as the method for improving the interfacial condition to enhance a characteristic, there is a suggestion on control of the interface by a silane coupling agent (for example, Surface Chemistry, 2007, vol. 28, no. 5, pp. 242-248).

Examples of the silane coupling agent include alkylchlorosilanes (octyltrichlorosilane (OTS), octadecyltrichlorosilane (ODTS), phenylethyltrichlorosilane and the like), alkylalkoxysilanes, fluorinated alkylchlorosilanes, fluorinated alkylalkoxysilanes; silylamine compounds such as hexamethyldisilazane (HMDS) and the like. Before treating with a surface treatment agent, the surface of an insulating layer may be subjected to an ozone UV treatment or an $O_2$ plasma treatment.

By such a treatment, the surface energy of a silicon oxide film or the like used as the insulating layer can be controlled. By the surface treatment, the orientation of a film constituting an active layer on an insulating layer improves and higher carrier mobility is obtained.

In the gate electrode 4, metals such as gold, platinum, silver, copper, chromium, palladium, aluminum, indium, molybdenum, low-resistance polysilicon, low-resistance amorphous silicon and the like and materials such as tin oxide, indium oxide, indium•tin oxide (ITO) and the like can be used.

These materials may be used each singly or two or more of them may be used in combination. As the gate electrode 4, a silicon substrate doped at high concentration can also be used. The silicon substrate doped at high concentration has a performance as a gate electrode and simultaneously has also a performance as a substrate. When such a gate electrode 4 having also a performance as a substrate is used, a substrate 1 may be omitted in an organic transistor in which a substrate 1 and a gate electrode 4 are in contact.

The source electrode 5 and the drain electrode 6 are preferably constituted of a low-resistance material, particularly preferably constituted of gold, platinum, silver, copper, chromium, palladium, aluminum, indium, molybdenum or the like. These materials may be used each singly or two or more of them may be used in combination.

In the above-described organic transistor, a layer constituted of the other compound may further intervene between the active layer 2, and the source electrode 5 and the drain electrode 6. Such a layer includes layers composed of a low molecular weight compound having electron transportability, a low molecular weight compound having hole transportability, an alkali metal, an alkaline earth metal, a rare earth metal, a complex of these metals with an organic compound, a halogen such as iodine, bromine, chlorine, iodine chloride and the like, a sulfur oxide compound such as sulfuric acid, anhydrous sulfuric acid, sulfur dioxide, sulfate and the like, a nitrogen oxide compound such as nitric acid, nitrogen dioxide, nitrate and the like, a halogenated compound such as perchloric acid, hypochlorous acid and the like, an alkylthiol compound, an aromatic thiol compound such as aromatic thiols, fluorinated alkylaromatic thiols and the like, etc.

After fabrication of an organic transistor as described above, it is preferable to form a protective film on the organic transistor for protecting the device. By this, an organic transistor is blocked from atmospheric air and lowering of the characteristic of an organic transistor can be suppressed. When a driving display device is formed on an organic transistor, an influence on an organic transistor in its formation step can be lowered by the protective film.

The method of forming the protective film includes methods in which an organic transistor is covered with an UV hardening resin, a thermosetting resin or an inorganic $SiON_x$ film and the like. For effectively blocking from atmospheric air, it is preferable to form a protective film without exposing an organic transistor to atmospheric air (for example, in a dried nitrogen atmosphere, in vacuum, and the like) after fabrication of the organic transistor.

An organic field effect type transistor which is a kind of organic transistor constituted as described above can be applied as an active matrix driving mode liquid crystal display, a pixel driving switching device of an organic electroluminescent display, and the like. The organic field effect type transistor according to the present embodiment described above contains the polymer compound of the present invention as an active layer, thus has an active layer excellent in carrier mobility, and obtains high carrier mobility. Therefore, the present transistor is useful for production of a display having sufficient response speed.

The organic film transistor of the present invention can be suitably used in an organic electroluminescent device, an electronic tag and a liquid crystal display device.

The composition or polymer compound of the present invention can also be used for production of an OFET sensor. The OFET sensor of the present invention uses an organic field effect type transistor as a signal conversion device outputting an input signal as an electric signal in which any structure of a metal, an insulating film and an organic semiconductor layer is endowed with a sensitive function or a selective function. The OFET sensor of the present invention includes, for example, a bio sensor, a gas sensor, an ion sensor and a humidity sensor.

The bio sensor has a substrate and an organic film transistor provided on the substrate. The organic film transistor has an organic semiconductor layer, a source region and a drain region provided in contact with an organic semiconductor, a channel region in the organic semiconductor layer provided between the source region and the drain region, a gate electrode which can apply electric field on the channel region, and a gate insulating film provided between the channel region and the gate electrode. The organic film transistor has a probe (sensitive region) mutually acting specifically with a standard substance in the channel region and/or the gate insulating film, and when the concentration of the standard substance changes, a characteristic change of the probe occurs, thus, the present transistor functions as a bio sensor.

The means for detecting a standard substance in a test sample includes, for example, a bio sensor in which a biological molecule such as a nucleic acid, a protein and the like or an artificially synthesized functional group is fixed as a probe to the surface of a solid phase carrier.

In this method, a standard substance is captured to the surface of a solid phase carrier by utilizing specific affinity of a biological molecule such as a mutual action of complementary nucleic acid chains, a mutual action of an antigen-antibody reaction, a mutual action of an enzyme-substrate reaction, a mutual action of receptor-ligand, and the like. Therefore, a substance showing specific affinity to a standard substance is selected as a probe.

The probe is fixed to the surface of a solid phase carrier by a method according to the kind of the probe and the kind of the solid phase carrier. It is also possible to synthesize a probe on the surface of a solid phase carrier (for example, a method of synthesizing a probe by a nucleic acid elongation reaction). In any case, a solid phase carrier surface to which a probe has been fixed and a test sample are mutually brought into contact and cultured under suitable conditions, resultantly, a probe-standard substance complex is formed on the solid phase carrier surface. A channel region and/or a gate insulating film itself contained in an organic film transistor may function as a probe.

The gas sensor has a substrate and an organic film transistor provided on the substrate. The organic film transistor has an organic semiconductor layer, a source region and a drain region provided in contact with an organic semiconductor, a channel region in the semiconductor layer provided between the source region and the drain region, a gate electrode which can apply electric field on the channel region, and a gate insulating film provided between the channel region and the gate electrode. In the organic film transistor, the channel region and/or the gate insulating film functions as a gas sensitive part. When a detection gas is adsorbed to or released from a gas sensitive part, a change of characteristics (electric conductivity, permittivity and the like) of the gas sensitive part occurs, thus, the present transistor functions as a gas sensor.

The gas to be detected includes, for example, an electron accepting gas and an electron donating gas. The electron accepting gas includes, for example, a halogen gas such as $F_2$, $Cl_2$ and the like; a nitrogen oxide gas; a sulfur oxide gas; and a gas of an organic acid such as acetic acid and the like. The electron donating gas includes, for example, an ammonia gas; a gas of amines such as aniline and the like; a carbon monoxide gas; and a hydrogen gas.

The composition or polymer compound of the present invention can also be used for production of a pressure sensor. The pressure sensor of the present invention has a substrate and an organic film transistor provided on the substrate. The organic film transistor has an organic semiconductor layer, a source region and a drain region provided in contact with an organic semiconductor, a channel region in the organic semiconductor layer provided between the source region and the drain region, a gate electrode which can apply electric field on the channel region, and a gate insulating film provided between the channel region and the gate electrode. In the organic film transistor, the channel region and/or the gate insulating film functions as a pressure sensitive part. When the pressure sensitive part senses pressure, a characteristic change of the pressure sensitive part occurs, thus, the present transistor functions as a pressure sensitive sensor.

When the gate insulating film functions as a pressure sensitive part, it is preferable that the gate insulating film contains an organic material since an organic material is excellent in flexibility and stretchability as compared with an inorganic material.

When the channel region functions as a pressure sensitive part, the organic film transistor may further have an orientation layer, for further enhancing crystallinity of an organic semiconductor contained in the channel region. The orientation layer includes, for example, a monomolecular film formed on a gate insulating film by using a silane coupling agent such as hexamethyldisilazane and the like.

Further, the composition or polymer compound of the present invention can also be used for production of a conductivity modulation type sensor. The conductivity modulation type sensor of the present invention uses a conductivity measuring device as a signal conversion device outputting an input signal as an electric signal, and it is a film containing the composition or polymer compound of the present invention or one obtained by imparting a sensitive function or a selective function against input of the sensor target to a coating of a film containing the composition or polymer compound of the present invention. The conductivity modulation type sensor of the present invention detects input of the sensor target as a change of conductivity of the composition or polymer compound of the present invention. The conductivity modulation type sensor of the present invention includes, for example, a bio sensor, a gas sensor, an ion sensor and a humidity sensor.

Still further, the composition or polymer compound of the present invention can also be used for production of an amplifying circuit containing an organic field effect type transistor as an amplifying circuit for amplifying an output signal from various sensors such as a bio sensor, a gas sensor, an ion sensor, a humidity sensor, a pressure sensor and the like formed separately.

Moreover, the composition or polymer compound of the present invention can also be used for production of a sensor array containing a plurality of various sensors such as a bio sensor, a gas sensor, an ion sensor, a humidity sensor, a pressure sensor and the like.

Still moreover, the composition or polymer compound of the present invention can also be used for production of an amplifying circuit-equipped sensor array containing a plurality of various sensors such as a bio sensor, a gas sensor, an ion sensor, a humidity sensor, a pressure sensor and the like formed separately and having an organic field effect type transistor as an amplifying circuit for separately amplifying output signals from various sensors.

EXAMPLES

Examples are shown below for illustrating the present invention further in detail, but the present invention is not limited to them.

(NMR Analysis)

A compound was dissolved in deuterated chloroform, and its NMR was measured using an NMR apparatus (manufactured by Varian Inc., INOVA300).

(Molecular Weight Analysis)

The number-average molecular weight and the weight-average molecular weight of a polymer compound were determined by using gel permeation chromatography (GPC, manufactured by Waters Corporation, trade name: Alliance GPC 2000). The polymer compound to be measured was dissolved in orthodichlorobenzene, and the solution was injected into GPC.

Orthodichlorobenzene was used as the mobile phase of GPC. TSKgel GMHHR-H(S)HT (two columns are connected, manufactured by Tosoh Corp.) was used as the column. An UV detector was used as the detector.

Synthesis Example 1

(Synthesis of Compound 2)

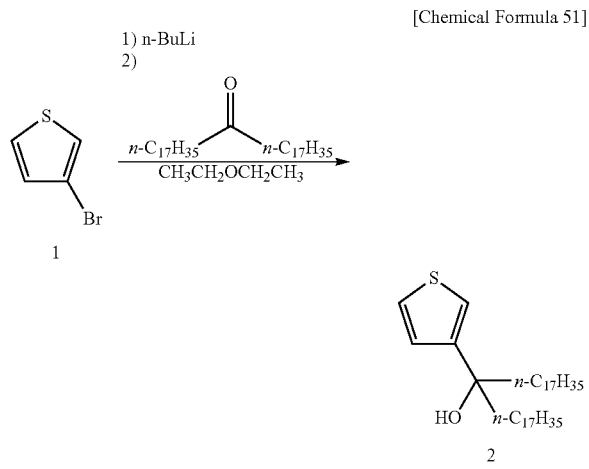

A nitrogen gas atmosphere was prepared in a reaction vessel, then, a compound 1 (32 g, 0.20 mol) and dehydrated diethyl ether (470 mL) were added, and a uniform solution was prepared. While keeping the resultant solution at −68° C., a 1.60 M n-butyllithium hexane solution (135 mL, 0.22 mol) was dropped over a period of 30 minutes. Thereafter, the mixture was stirred at −68° C. for 2 hours. Thereafter, to this was added 18-pentatriacontanone (69.7 g, 0.14 mol), and the mixture was stirred at −78° C. for 10 minutes, then, stirred at room temperature (25° C.) for 5 hours. Thereafter, to this was added water (200 mL) to stop the reaction, and a 10 wt-% acetic acid aqueous solution was added to make the reaction solution acidic. Thereafter, the reaction product was extracted using hexane. The resultant organic layer was washed with water, dried over anhydrous magnesium sulfate, and filtrated. The resultant filtrate was concentrated by an evaporator, then, the solvent was distilled off, to obtain 125 g of a compound 2. The yield was 100%.

$^1$H-NMR (300 MHz, CDCl$_3$): δ (ppm)=0.88 (t, 6H), 1.25 (m, 60H), 1.75 (m, 4H), 6.96 (d, 1H), 7.27 (d, 1H).

Synthesis Example 2

(Synthesis of Compound 3)

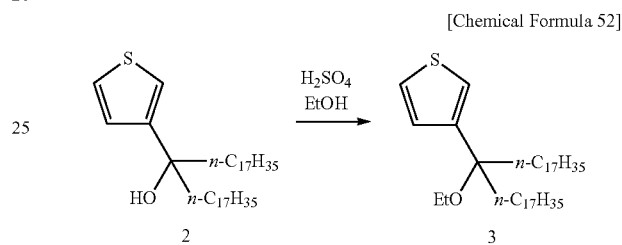

A nitrogen gas atmosphere was prepared in a reaction vessel, then, the compound 2 (232 g, 0.39 mol) and dehydrated ethanol (880 mL) and hexane (350 mL) were added, and a suspension was prepared. To the resultant suspension was added 96 wt % concentrated sulfuric acid (31 mL, 0.59 mol), then, the mixture was stirred at room temperature for 6 hours. Thereafter, to this was added water (200 mL) to stop the reaction, and the reaction product was extracted using hexane. The resultant organic layer was washed with water, dried over anhydrous magnesium sulfate, and filtrated. The resultant filtrate was concentrated by an evaporator, then, the solvent was distilled off. The resultant residue was purified by silica gel column chromatography using hexane as a moving bed, to obtain 104 g of a compound 3. The yield was 43%.

$^1$H-NMR (300 MHz, CDCl$_3$): δ (ppm)=0.88 (t, 6H), 1.13 (t, 3H), 1.24 (m, 60H), 1.77 (m, 4H), 3.15 (q, 2H), 7.05 (m, 2H), 7.24 (d, 1H).

Synthesis Example 3

(Synthesis of Compound 4)

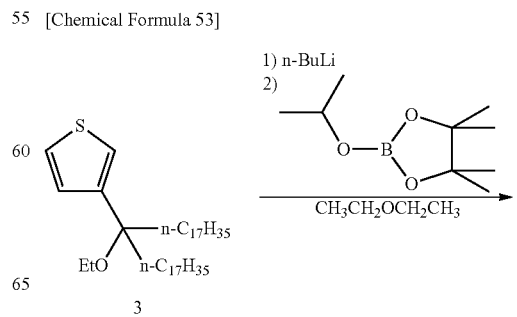

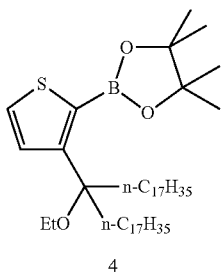

A nitrogen gas atmosphere was prepared in a reaction vessel, then, the compound 3 (104 g, 0.17 mol) and dehydrated diethyl ether (1020 mL) were added, and a uniform solution was prepared. While keeping the resultant solution at −68° C., a 1.60 M n-butyllithium hexane solution (136 mL, 0.22 mol) was dropped over a period of 10 minutes. Thereafter, the mixture was stirred at −68° C. for 10 minutes, then, stirred at room temperature (25° C.) for 1.5 hours. Thereafter, while keeping the resultant solution at −68° C., 2-isopropoxy-4,4,5,5-tetramethyl-1,3,2-dioxaborolana (62.5 g, 0.34 mmol) was added. Thereafter, the mixture was stirred at −68° C. for 10 minutes, then, stirred at room temperature (25° C.) for 2 hours. Thereafter, to this was added water (100 mL) to stop the reaction, and the reaction product was extracted using diethyl ether. The resultant organic layer was washed with water, dried over anhydrous magnesium sulfate, and filtrated. The resultant filtrate was concentrated by an evaporator, then, the solvent was distilled off, to obtain 117 g of a compound 4. The yield was 93%.

1H-NMR (300 MHz, CDCl$_3$): δ (ppm)=0.88 (t, 6H), 1.24 (m, 75H), 1.99 (m, 4H), 3.22 (q, 2H), 7.26 (d, 1H), 7.42 (d, 1H).

Synthesis Example 4

(Synthesis of Compound 5)

[Chemical Formula 54]

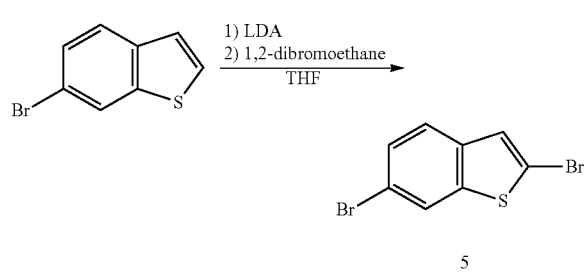

A nitrogen gas atmosphere was prepared in a reaction vessel, then, diisopropylamine (13.3 mL, 93.9 mmol) and dehydrated THF (196 mL) were added, and a uniform solution was prepared. Thereafter, into this was dropped a 1.65 M n-butyllithium hexane solution (58.9 mL, 93.9 mmol) over a period of 10 minutes, and the mixture was stirred at −50° C. for 0.5 hours, then, 6-bromobenzothiophene (10.0 g, 46.9 mmol) was added, and the mixture was stirred at −50° C. for 3 hours. To this was added 1,2-dibromoethane (17.6 g, 93.9 mmol), and the mixture was heated up to room temperature. After stirring for 2 hours, water (20 mL) was added to stop the reaction, and the reaction product was extracted using toluene. The resultant organic layer was washed with water, dried over anhydrous magnesium sulfate, and filtrated. The resultant filtrate was concentrated by an evaporator, then, the solvent was distilled off. The resultant residue was recrystallized using a mixed solvent of chloroform and methanol, to obtain 8.5 g of a compound 5. The yield was 62%.

$^1$H-NMR (300 MHz, CDCl$_3$): δ (ppm)=7.28 (s, 1H), 7.43 (dd, 1H), 7.54 (d, 1H), 7.87 (d, 1H).

Synthesis Example 5

(Synthesis of Compound 6)

[Chemical Formula 55]

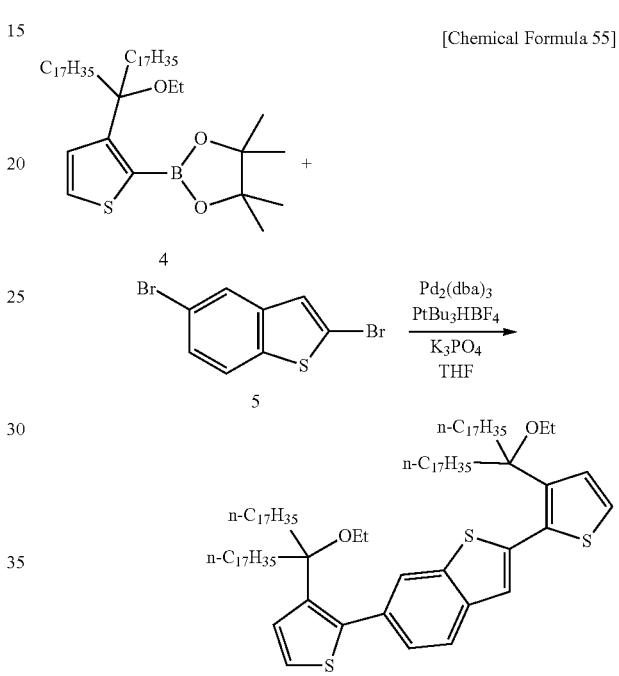

A nitrogen gas atmosphere was prepared in a reaction vessel equipped with a reflux tube, then, a compound 5 (3.5 g, 12.0 mmol) and dry THF (100 mL) were added, and the mixture was deaerated for 30 minutes by bubbling with an argon gas. Thereafter, to this were added tris(dibenzylideneacetone)dipalladium(0) (0.11 g, 0.12 mmol), tri-tert-butylphosphonium tetrafluoroborate (0.14 g, 0.48 mmol) and a 3M potassium phosphate aqueous solution (44 mL), and the mixture was heated at 80° C. Thereafter, a dry THF (3 mL) solution of a compound 4 (22.8 g, 30.0 mmol) which had been deaerated for 30 minutes by bubbling with an argon gas was dropped into this at 80° C. over a period of 2 minutes, and the mixture was heated at the same temperature for 2.5 hours. Thereafter, the reaction product was extracted using hexane. The resultant organic layer was washed with saturated saline, dried over anhydrous magnesium sulfate, and filtrated. The resultant filtrate was concentrated by an evaporator, then, the solvent was distilled off. The resultant residue was purified by silica gel column chromatography using a mixed solvent of hexane and chloroform as a moving bed, to obtain 9 g of a compound 6. The yield was 22%.

1H-NMR (300 MHz, CDCl$_3$): δ (ppm)=0.89 (t, 12H), 1.05 (m, 126H), 1.55 (m, 4H), 1.85 (m, 4H), 3.23 (m, 4H), 7.05 (d, 2H), 7.20 (d, 1H), 7.27 (d, 1H), 7.37 (dd, 1H), 7.41 (s, 1H), 7.67 (d, 1H), 7.78 (s, 1H).

Example 1

(Synthesis of Compound 7)

[Chemical Formula 56]

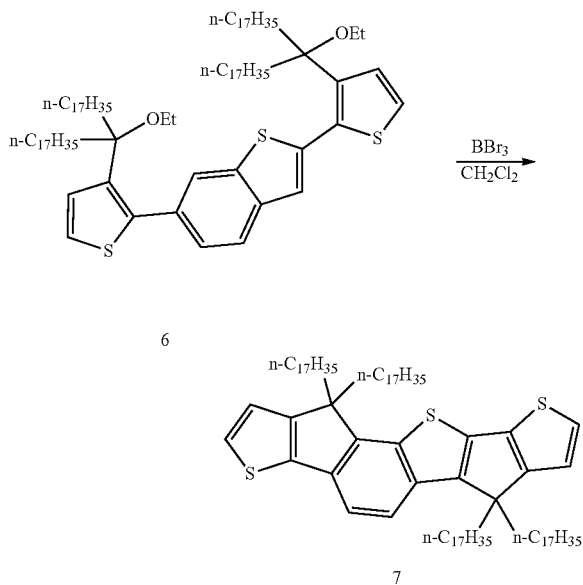

A nitrogen gas atmosphere was prepared in a reaction vessel, then, a compound 6 (7.61 g, 5.56 mmol) and dry methylene chloride (129 mL) were added. Thereafter, to this was added a 1 M boron tribromide methylene chloride solution (22.2 mL, 22.2 mmol) at 0° C., and the mixture was stirred at room temperature (25° C.) for 24 hours. Thereafter, to this was added water, and the reaction product was extracted using chloroform. The resultant organic layer was washed with water, dried over anhydrous magnesium sulfate, and filtrated. The resultant filtrate was concentrated by an evaporator, then, the solvent was distilled off. The resultant residue was purified by silica gel column chromatography using hexane as a moving bed, to obtain 4.5 g of a compound 7. The yield was 53%.

1H-NMR (300 MHz, CDCl$_3$): δ (ppm)=0.89 (t, 12H), 1.23 (m, 120H), 2.11 (m, 8H), 7.03 (m, 2H), 7.23 (d, 1H), 7.28 (d, 1H), 7.47 (d, 1H), 7.65 (d, 1H).

Example 2

(Synthesis of Compound 8)

[Chemical Formula 57]

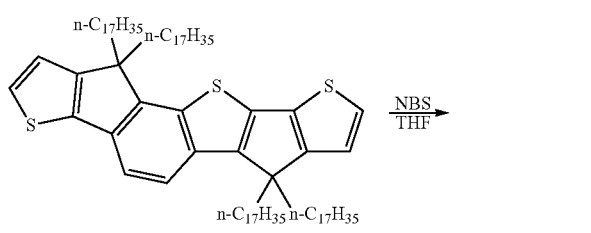

A nitrogen gas atmosphere was prepared in a reaction vessel, then, the compound 7 (7.6 g, 5.56 mmol) and dry THF (130 mL) were added. Thereafter, to this was added N-bromosuccinic imide (5.57 g, 22.2 mmol) at room temperature, and the mixture was stirred at room temperature for 3 hours. Thereafter, to this were added a saturated sodium thiosulfate aqueous solution (2 mL) and water (100 mL), and the mixture was stirred at room temperature for 5 minutes, then, the reaction product was extracted using hexane. The resultant organic layer was washed with water, dried over anhydrous magnesium sulfate, and filtrated. The resultant filtrate was concentrated by an evaporator, then, the solvent was distilled off. The resultant residue was purified by silica gel column chromatography using hexane as a moving bed, and recrystallized using hexane, to obtain 4.5 g of a compound 8. The yield was 53%.

1H-NMR (300 MHz, CDCl$_3$): δ (ppm)=0.85 (t, 12H), 1.05 (m, 120H), 2.06 (m, 8H), 7.03 (s, 1H), 7.04 (s, 1H), 7.40 (d, 1H), 7.62 (d, 1H).

Example 3

(Synthesis of Polymer Compound A)

[Chemical Formula 58]

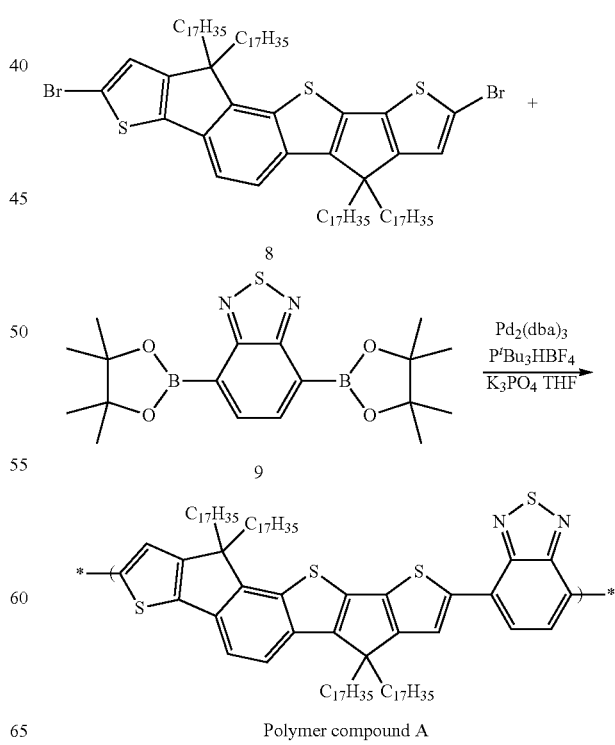

Polymer compound A

A gas in a reaction vessel was purged with a nitrogen gas, then, the compound 8 (286.8 mg, 0.200 mmol), a compound 9 (77.6 mg, 0.200 mmol), 19 mL of tetrahydrofuran, 7.3 mg of tris(dibenzylideneacetone)dipalladium and 9.3 mg of tri-tert-butylphosphonium tetrafluoroborate were added, and the mixture was stirred. Into the resultant reaction solution was dropped 1.0 mL of a 3 mol/L potassium phosphate aqueous solution, and the mixture was refluxed for 3 hours. To the resultant reaction solution was added 24.4 mg of phenylboronic acid, and the mixture was refluxed for 1 hour. To the resultant reaction solution was added 0.1 g of sodium N,N-diethyldithiocarbamate trihydrate, and the mixture was refluxed for 3 hours. The resultant reaction solution was poured into water, toluene was added, and the toluene layer was extracted. The resultant toluene solution was washed with an acetic acid aqueous solution and water, then, purified using a silica gel column. The resultant toluene solution was dropped into acetone, to obtain a deposit. The resultant deposit was washed in a Soxhlet extractor using acetone as a solvent, to obtain a polymer compound A. The amount gained was 244 mg, and the polystyrene-equivalent number-average molecular weight was $3.1 \times 10^4$ and the weight-average molecular weight was $6.5 \times 10^4$.

Comparative Example 1

(Synthesis of Polymer Compound X1)

[Chemical Formula 59]

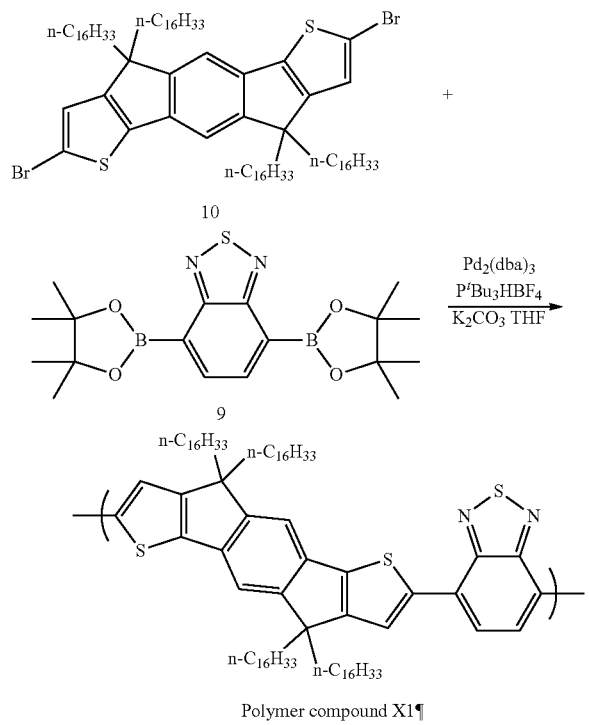

Polymer compound X1

A nitrogen gas atmosphere was prepared in a reaction vessel, then, a compound 10 (0.300 g, 0.227 mmol), a compound 9 (0.0881 g, 0.227 mmol) synthesized according to a method described in "J. Am. Chem. Soc., 2010, 132, 11437-11439", tetrahydrofuran (30 mL), tris(dibenzylideneacetone)dipalladium (4.2 mg) and tri-tert-butylphosphonium tetrafluoroborate (5.3 mg) were added, and the mixture was stirred. Thereafter, into this was dropped a 2 mol/L potassium carbonate aqueous solution (1.13 mL), and the mixture was refluxed for 5 hours. Thereafter, to this was added phenylboronic acid (10.0 mg), and the mixture was refluxed for 1 hour. Thereafter, to this was added sodium N,N-diethyldithiocarbamate trihydrate (0.1 g), and the mixture was refluxed for 3 hours. The resultant the reaction liquid was poured into water, toluene was added, and the toluene layer was extracted. The resultant toluene solution was washed with an acetic acid aqueous solution and water, then, purified using a silica gel column. The resultant toluene solution was dropped into acetone, to obtain a deposit. The resultant deposit was washed in a Soxhlet extractor using acetone as a solvent, to obtain a polymer compound X1. The amount gained was 270 mg, and the polystyrene-equivalent number-average molecular weight was $3.0 \times 10^4$ and the weight-average molecular weight was $1.1 \times 10^5$.

Example 4

(Fabrication and Evaluation of Organic Transistor 1)

An organic transistor 1 having the BGBC device structure shown in FIG. 3 was fabricated by using a solution containing the polymer compound A.

The surface of an n-type silicon substrate doped at high concentration as a gate electrode was thermally oxidized, to form a silicon oxide film (hereinafter, referred to as "thermally oxidized film"). Thermally oxidized film functions as an insulating layer.

Next, a source electrode and a drain electrode were fabricated on the thermally oxidized film by a photo lithography step. The source electrode and the drain electrode had a chromium (Cr) layer and a gold (Au) layer in this order from the side of the thermally oxidized film, and the channel length thereof was 20 µm and the channel width thereof was 2 mm.

Thus resultant substrate carrying the thermally oxidized film, the source electrode and the drain electrode formed thereon was ultrasonically cleaned with acetone, and subjected to an UV ozone treatment by an ozone UV cleaner. Thereafter, the surface of the thermally oxidized film was modified with β-phenethyltrichlorosilane.

Next, on the thermally oxidized film, the source electrode and the drain electrode surface-treated as described above, a 0.5 wt % orthodichlorobenzene solution of the polymer compound A as spin-coated at a revolution of 1000 rpm, to form an organic semiconductor layer (active layer). Thereafter, the organic semiconductor layer was heated at 150° C. for 30 minutes, to produce an organic transistor 1.

The gate voltage Vg and the source-drain voltage Vsd of the resultant organic transistor 1 were changed, and the transistor properties were measured. The on/off ratio was $10^6$ and the carrier mobility was 0.15 cm$^2$/Vs. The results are shown in Table 1.

Comparative Example 2

(Fabrication and Evaluation of Organic Transistor 2)

An organic transistor 2 was fabricated in the same manner as in Example 4, excepting that the polymer compound X1 was used instead of the polymer compound A in Example 4.

The gate voltage Vg and the source-drain voltage Vsd of the resultant organic transistor 2 were changed, and the transistor properties were measured. The on/off ratio was 10' and the carrier mobility was 0.048. The results are shown in Table 1.

Example 5

(Fabrication and Evaluation of Organic Transistor 3)

An organic transistor 3 having the TGBC device structure shown in FIG. 1 was fabricated by using a solution containing the polymer compound A.

A glass substrate (substrate 1) was ultrasonically cleaned with acetone for 10 minutes, then, irradiated with ozone UV for 20 minutes. Thereafter, a source electrode 5 and a drain electrode 6 were formed on the substrate 1 by a vapor deposition method. The source electrode 5 and the drain electrode 6 were composed of gold, and the channel length thereof was 20 μm and the channel width thereof was 2 mm. Thereafter, the surface of the substrate was silane-treated by immersing the substrate in a toluene-diluted solution of phenylethyltrichlorosilane for 2 minutes. Thereafter, the substrate was immersed in an isopropyl alcohol-diluted solution of pentafluorobenzenethiol for 2 minutes, to modify the surface of the electrode formed on the substrate.

Thereafter, a 0.5 wt % tetralin solution of the polymer compound A was applied on the surface-treated substrate described above by a spin coat method, and dried on a hot plate at 150° C. for 30 minutes under an air atmosphere, to form an organic semiconductor layer 2. The organic semiconductor layer 2 had a thickness of about 30 nm.

Thereafter, an insulating film made of Teflon (registered trademark) was applied on the organic semiconductor layer 2 by a spin coat method, and dried on a hot plate at 80° C. for 10 minutes under an air atmosphere, to form an insulating layer 3. The insulating layer 3 had a thickness of about 500 nm.

Thereafter, a film of aluminum was formed on the insulating film 3 by a vapor deposition method, to form a gate electrode 4.

The gate voltage Vg and the source-drain voltage Vsd of the resultant organic transistor 3 were changed, and the transistor properties were measured. The on/off ratio was $10^6$ and the carrier mobility was 0.99 cm$^2$/Vs. The results are shown in Table 1.

Comparative Example 3

(Fabrication and Evaluation of Organic Transistor 4)

An organic transistor 4 was fabricated in the same manner as in Example 5, excepting that the polymer compound X1 was used instead of the polymer compound A in Example 5.

The gate voltage Vg and the source-drain voltage Vsd of the resultant organic transistor 2 were changed, and the transistor properties were measured. The on/off ratio was $10^6$ and the carrier mobility was 0.85. The results are shown in Table 1.

Example 6

(Fabrication and Evaluation of Organic Transistor 5)

An organic transistor 5 was fabricated in the same manner as in Example 5, excepting that the channel length was changed to 5 μm in Example 5.

The gate voltage Vg and the source-drain voltage Vsd of the resultant organic transistor 5 were changed, and the transistor properties were measured. The on/off ratio was $10^6$ and the carrier mobility was 1.62. The results are shown in Table 1.

Comparative Example 4

(Fabrication and Evaluation of Organic Transistor 6)

An organic transistor 5 was fabricated in the same manner as in Example 5, excepting that the channel length was changed to 5 μm in Example 5.

The gate voltage Vg and the source-drain voltage Vsd of the resultant organic transistor 6 were changed, and the transistor properties were measured. The on/off ratio was $10^5$ and the carrier mobility was 0.45. The results are shown in Table 1.

Example 7

(Synthesis of Polymer Compound B)

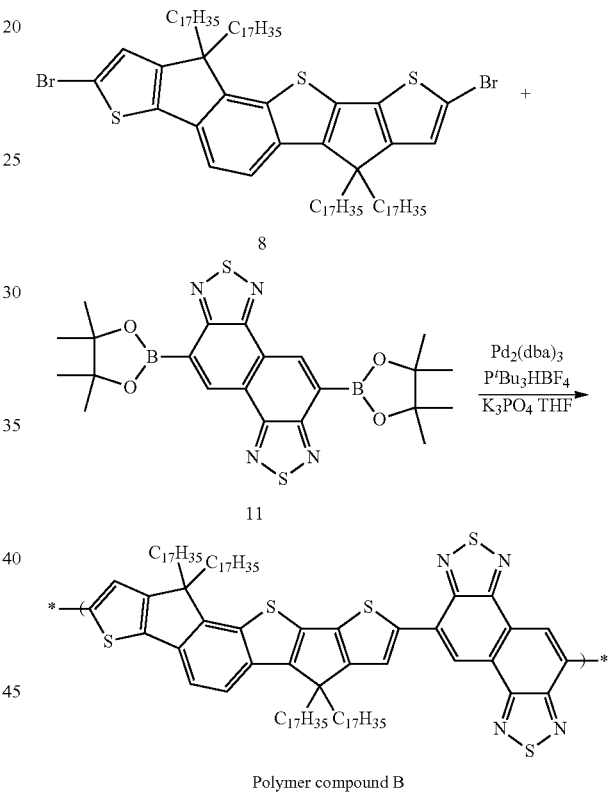

Polymer compound B

A gas in a reaction vessel was purged with a nitrogen gas, then, the compound 8 (296.78 mg, 0.200 mmol), a compound 11 (99.24 mg, 0.200 mmol) synthesized by a method described in WO2013-161377, 19 mL of tetrahydrofuran, 7.3 mg of tris(dibenzylideneacetone)dipalladium and 9.3 mg of tri-tert-butylphosphonium tetrafluoroborate were added, and the mixture was stirred. Into the resultant reaction solution, 1.0 mL of a 3 mol/L potassium phosphate aqueous solution was dropped, and the mixture was refluxed for 3 hours. To the resultant reaction solution was added 24.4 mg of phenylboronic acid, and the mixture was refluxed for 1 hour. To the resultant reaction solution was added 0.1 g of sodium N,N-diethyldithiocarbamate trihydrate, and the mixture was refluxed for 3 hours. The resultant reaction solution was poured into water, toluene was added, and the toluene layer was extracted. The resultant toluene solution was washed with an acetic acid aqueous solution and water, then, purified using a silica gel column. The resultant toluene solution was dropped into acetone, to obtain a deposit. The resultant deposit was washed in a Soxhlet extractor using acetone as a solvent, to obtain a polymer compound B. The amount gained was 280 mg, and the polystyrene-equivalent number-average molecular weight was $4.7 \times 10^4$ and the weight-average molecular weight was $1.1 \times 10^5$.

Example 8

(Fabrication and Evaluation of Organic Transistor 7)

An organic transistor 7 was fabricated in the same manner as in Example 4, excepting that the polymer compound B was used instead of the polymer compound A in Example 4.

The gate voltage Vg and the source-drain voltage Vsd of the resultant organic transistor 7 were changed, and the transistor properties were measured. The on/off ratio was $10^5$ and the carrier mobility was 0.2. The results are shown in Table 1.

Example 9

(Fabrication and Evaluation of Organic Transistor 8)

An organic transistor 8 was fabricated in the same manner as in Example 5, excepting that the polymer compound B was used instead of the polymer compound A in Example 5.

The gate voltage Vg and the source-drain voltage Vsd of the resultant organic transistor 8 were changed, and the transistor properties were measured. The on/off ratio was $10^6$ and the carrier mobility was 0.90. The results are shown in Table 1.

Example 10

(Fabrication and Evaluation of Organic Transistor 9)

An organic transistor 9 was fabricated in the same manner as in Example 6, excepting that the polymer compound B was used instead of the polymer compound A in Example 6.

The gate voltage Vg and the source-drain voltage Vsd of the resultant organic transistor 9 were changed, and the transistor properties were measured. The on/off ratio was $10^6$ and the carrier mobility was 2.50. The results are shown in Table 1.

TABLE 1

| polymer compound used in organic transistor | carrier mobility (cm²/Vs) | | |
|---|---|---|---|
| | BGBC device structure (channel length: 20 μm) | TGBC device structure (channel length: 20 μm) | TGBC device structure (channel length: 5 μm) |
| Examples 4, 5, 6 | polymer compound A | 0.15 | 0.29 | 1.62 |
| Examples 8, 9, 10 | polymer compound B | 0.20 | 0.90 | 2.50 |
| Comparative Examples 2, 3, 4 | polymer compound X1 | 0.048 | 0.85 | 0.45 |

It is understood from the results of Table 1 that the organic transistor produced by using the polymer compound of the present invention shows high carrier mobility in any of the BGBC device structure and the TGBC device structure.

INDUSTRIAL APPLICABILITY

According to the present invention, a polymer compound which is useful for production of an organic transistor more excellent in carrier mobility in any of the BGBC device structure and the TGBC device structure can be provided.

EXPLANATION OF NUMERALS

1: substrate
2, 2a: active layer
3: insulating layer
4: gate electrode
5: source electrode
6: drain electrode
100, 110, 120, 130, 140, 150, 160, 170, 180: organic transistor

The invention claimed is:

1. A polymer compound comprising a structural unit represented by the formula (1):

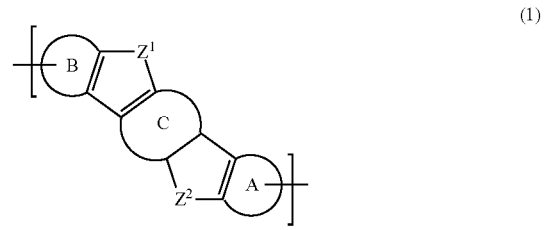

(1)

wherein
a ring A and a ring B each independently represent a heterocyclic ring, and the heterocyclic ring optionally has a substituent;
a ring C represents a condensed aromatic heterocyclic ring not having a line-symmetric axis and a rotational axis, and the aromatic heterocyclic ring optionally has a substituent;
$Z^1$ and $Z^2$ each independently represent a group represented by the formula (Z-1), a group represented by the formula (Z-2), a group represented by the formula (Z-3), a group represented by the formula (Z-4), a group represented by the formula (Z-5), a group represented by the formula (Z-6) or a group represented by the formula (Z-7);

(Z-1)

(Z-2)

(Z-3)

(Z-4)

(Z-5)

-continued

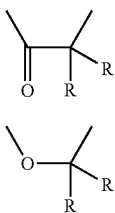

(Z-6)

(Z-7)

wherein

R represents an alkyl group, a cycloalkyl group, an alkoxy group, a cycloalkoxy group, an alkylthio group, a cycloalkylthio group, an aryl group or a monovalent heterocyclic group, and these groups optionally have a substituent; and when a plurality of R are present, they may be the same or different.

2. The polymer compound according to claim 1, wherein the structural unit represented by the formula (1) is a structural unit represented by the formula (2):

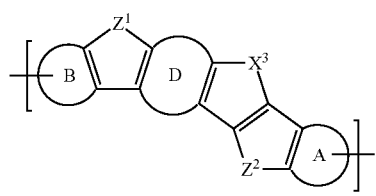

(2)

wherein a ring A, a ring B, $Z^1$ and $Z^2$ represent the same meaning as described above;

$X^3$ represents an oxygen atom, a sulfur atom or a selenium atom; and a ring D represents an aromatic hydrocarbon ring selected from the group consisting of a benzene ring and a condensed ring obtained by condensation of 2 to 4 benzene rings, and the aromatic hydrocarbon ring optionally has a substituent.

3. The polymer compound according to claim 2, wherein the structural unit represented by the formula (2) is a structural unit represented by the formula (3):

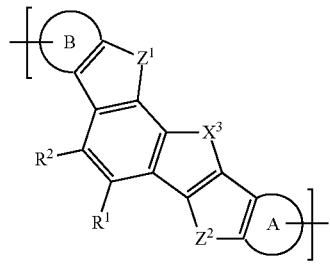

(3)

wherein a ring A, a ring B, $X^3$, $Z^1$ and $Z^2$ represent the same meaning as described above;

$R^1$ and $R^2$ each independently represent a hydrogen atom, an alkyl group, a cycloalkyl group, an alkoxy group, a cycloalkoxy group, an alkylthio group, a cycloalkylthio group, an aryl group, a monovalent heterocyclic group, a halogen atom, a silyl group, an amino group, an alkenyl group, a cycloalkenyl group, an alkynyl group, a hydroxyl group, a nitro group, a cyano group, a carboxyl group, an alkylcarbonyl group, a cycloalkylcarbonyl group, an alkoxycarbonyl group or a cycloalkoxycarbonyl group, and of these groups, an alkyl group, a cycloalkyl group, an alkoxy group, a cycloalkoxy group, an alkylthio group, a cycloalkylthio group, an aryl group, a monovalent heterocyclic group, a silyl group, an amino group, an alkenyl group, a cycloalkenyl group, an alkynyl group, an alkylcarbonyl group, a cycloalkylcarbonyl group, an alkoxycarbonyl group and a cycloalkoxycarbonyl group each optionally have a substituent.

4. The polymer compound according to claim 3, wherein the structural unit represented by the formula (3) is a structural unit represented by the formula (4):

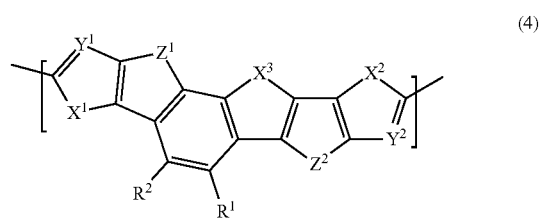

(4)

wherein $R^1$, $R^2$, $X^3$, $Z^1$ and $Z^2$ represent the same meaning as described above;

$X^1$ and $X^2$ each independently represent an oxygen atom, a sulfur atom or a selenium atom; and $Y^1$ represents a nitrogen atom or a group represented by $—CR^5=$, and $Y^2$ represents a nitrogen atom or a group represented by $—CR^6=$, $R^5$ and $R^6$ each independently represent a hydrogen atom, an alkyl group, a cycloalkyl group, an alkoxy group, a cycloalkoxy group, an alkylthio group, a cycloalkylthio group, an aryl group, a monovalent heterocyclic group or a halogen atom, and of these groups, an alkyl group, a cycloalkyl group, an alkoxy group, a cycloalkoxy group, an alkylthio group, a cycloalkylthio group, an aryl group and a monovalent heterocyclic group each optionally have a substituent.

5. The polymer compound according to claim 4, wherein $X^1$, $X^2$ and $X^3$ each represent a sulfur atom.

6. The polymer compound according to claim 4, wherein $Y^1$ and $Y^2$ represent a group represented by $—CH=$.

7. The polymer compound according to claim 1, wherein $Z^1$ and $Z^2$ represent a group represented by formula (Z-1).

8. The polymer compound according to claim 1, further comprising a structural unit represented by the formula (5):

(5)

wherein

Ar represents an arylene group or a divalent heterocyclic group, and these groups optionally have a substituent.

9. The polymer compound according to claim 8, wherein the polymer compound is an alternate copolymer of the structural unit represented by the formula (1) and the structural unit represented by the formula (5).

10. A compound represented by the formula (6):

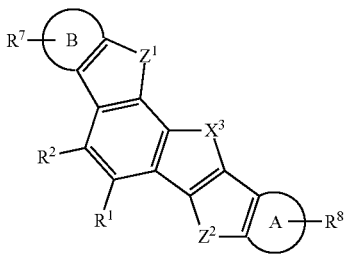 (6)

wherein
a ring A and a ring B each independently represent a heterocyclic ring, and the heterocyclic ring optionally has a substituent other than $R^7$ and $R^8$;
$X^3$ represents an oxygen atom, a sulfur atom or a selenium atom;
$Z^1$ and $Z^2$ each independently represent a group represented by the formula (Z-1), a group represented by the formula (Z-2), a group represented by the formula (Z-3), a group represented by the formula (Z-4), a group represented by the formula (Z-5), a group represented by the formula (Z-6) or a group represented by the formula (Z-7);
$R^1$ and $R^2$ each independently represent a hydrogen atom, an alkyl group, a cycloalkyl group, an alkoxy group, a cycloalkoxy group, an alkylthio group, a cycloalkylthio group, an aryl group, a monovalent heterocyclic group, a halogen atom, a silyl group, an amino group, an alkenyl group, a cycloalkenyl group, an alkynyl group, a hydroxyl group, a nitro group, a cyano group, a carboxyl group, an alkylcarbonyl group, a cycloalkylcarbonyl group, an alkoxycarbonyl group or a cycloalkoxycarbonyl group, and of these groups, an alkyl group, a cycloalkyl group, an alkoxy group, a cycloalkoxy group, an alkylthio group, a cycloalkylthio group, an aryl group, a monovalent heterocyclic group, a silyl group, an amino group, an alkenyl group, a cycloalkenyl group, an alkynyl group, an alkylcarbonyl group, a cycloalkylcarbonyl group, an alkoxycarbonyl group and a cycloalkoxycarbonyl group each optionally have a substituent; $R^7$ and $R^8$ each independently represent a hydrogen atom, a halogen atom, a silyl group, a hydroxyl group, a carboxyl group, a borate residue, a boric acid residue or an organotin residue, and of these groups, a silyl group optionally has a substituent;

 (Z-1)

 (Z-2)

 (Z-3)

 (Z-4)

 (Z-5)

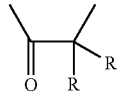 (Z-6)

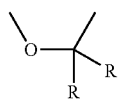 (Z-7)

wherein
R represents an alkyl group, a cycloalkyl group, an alkoxy group, a cycloalkoxy group, an alkylthio group, a cycloalkylthio group, an aryl group or a monovalent heterocyclic group, and these groups optionally have a substituent; and when a plurality of R are present, they may be the same or different.

11. The compound according to claim 10, wherein the compound represented by the formula (6) is a compound represented by the formula (7):

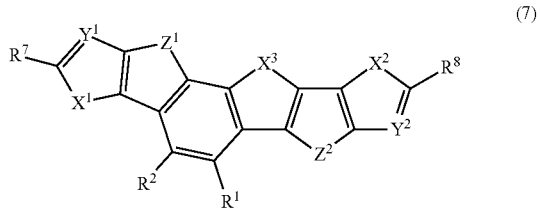 (7)

wherein
$R^1$, $R^2$, $R^7$, $R^8$, $X^3$, $Z^1$ and $Z^2$ represent the same meaning as described above;
$X^1$ and $X^2$ each independently represent an oxygen atom, a sulfur atom or a selenium atom;
$Y^1$ represents a nitrogen atom or a group represented by —$CR^5$=, and $Y^2$ represents a nitrogen atom or a group represented by —$CR^6$=, $R^5$ and $R^6$ each independently represent a hydrogen atom, an alkyl group, a cycloalkyl group, an alkoxy group, a cycloalkoxy group, an alkylthio group, a cycloalkylthio group, an aryl group, a monovalent heterocyclic group or a halogen atom, and of these groups, an alkyl group, a cycloalkyl group, an alkoxy group, a cycloalkoxy group, an alkylthio group, a cycloalkylthio group, an aryl group and a monovalent heterocyclic group each optionally have a substituent.

12. An organic semiconductor composition comprising the polymer compound according to claim 1.

13. An organic semiconductor device having a first electrode, a second electrode and an organic semiconductor layer, wherein the organic semiconductor layer contains the polymer compound according to claim 1.

14. The organic semiconductor device according to claim 13, wherein the device is any of an organic transistor, a photoelectric conversion device, an organic electroluminescent device, an organic field effect type transistor sensor and an organic conductivity modulation type sensor.

15. The organic semiconductor device according to claim 14, wherein the device is an organic transistor.

\* \* \* \* \*